(12) United States Patent
Smith et al.

(10) Patent No.: US 8,846,906 B2
(45) Date of Patent: Sep. 30, 2014

(54) 5HT$_{2C}$ RECEPTOR MODULATORS

(75) Inventors: Jeffrey Smith, San Diego, CA (US); Brian Smith, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/616,981

(22) Filed: Sep. 14, 2012

(65) Prior Publication Data
US 2013/0217676 A1  Aug. 22, 2013

Related U.S. Application Data

(63) Continuation of application No. 13/523,805, filed on Jun. 14, 2012, now Pat. No. 8,273,734, which is a continuation of application No. 13/118,126, filed on May 27, 2011, now Pat. No. 8,207,158, which is a continuation of application No. 11/599,050, filed on Nov. 14, 2006, now Pat. No. 7,977,329, which is a continuation of application No. 10/917,979, filed on Aug. 13, 2004, now Pat. No. 7,514,422, which is a continuation of application No. 10/410,991, filed on Apr. 10, 2003, now Pat. No. 6,953,787.

(60) Provisional application No. 60/372,058, filed on Apr. 12, 2002, provisional application No. 60/405,495, filed on Aug. 23, 2002, provisional application No. 60/434,607, filed on Dec. 18, 2002.

(51) Int. Cl.
| | |
|---|---|
| *C07D 223/14* | (2006.01) |
| *C07D 223/16* | (2006.01) |
| *C07D 487/00* | (2006.01) |
| *C07D 491/00* | (2006.01) |
| *C07D 403/04* | (2006.01) |
| *C07D 409/04* | (2006.01) |
| *C07D 491/04* | (2006.01) |

(52) U.S. Cl.
CPC ............ *C07D 223/16* (2013.01); *C07D 403/04* (2013.01); *C07D 409/04* (2013.01); *C07D 491/04* (2013.01)
USPC ........................................................ 540/494

(58) Field of Classification Search
USPC ........................................................ 540/594
See application file for complete search history.

(56) References Cited

U.S. PATENT DOCUMENTS

| | | | |
|---|---|---|---|
| 3,652,543 A | 3/1972 | Hoegerle | |
| 3,716,639 A | 2/1973 | Hoegerle et al. | |
| 3,795,683 A | 3/1974 | Brossi et al. | |
| 4,108,989 A | 8/1978 | Holden | |
| 4,111,957 A | 9/1978 | Holden et al. | |
| 4,210,729 A | 7/1980 | Hermans et al. | |
| 4,210,749 A | 7/1980 | Shetty | |
| 4,233,217 A | 11/1980 | Shetty | |
| 4,762,845 A | 8/1988 | Chu et al. | |
| 4,988,690 A | 1/1991 | Effland et al. | |
| 5,015,639 A | 5/1991 | Berger et al. | |
| 5,178,786 A | 1/1993 | Jahnke et al. | |
| 5,247,080 A | 9/1993 | Berger et al. | |
| 5,275,915 A | 1/1994 | Kojima et al. | |
| 5,387,685 A | 2/1995 | Powell et al. | |
| 5,412,119 A | 5/1995 | Brussee et al. | |
| 5,422,355 A | 6/1995 | White et al. | |
| 5,691,362 A | 11/1997 | McCormick et al. | |
| 5,750,520 A | 5/1998 | Danilewicz et al. | |
| 5,856,503 A | 1/1999 | Aebi et al. | |
| 5,861,393 A | 1/1999 | Danilewicz et al. | |
| 5,925,651 A | 7/1999 | Hutchinson | |
| 5,939,415 A | 8/1999 | Laufer et al. | |
| 5,942,535 A | 8/1999 | Laufer et al. | |
| 5,958,943 A | 9/1999 | Laufer et al. | |
| 6,087,346 A | 7/2000 | Glennon et al. | |
| 6,218,385 B1 | 4/2001 | Adam et al. | |
| 6,900,313 B2 | 5/2005 | Wasserscheid et al. | |
| 6,953,787 B2 | 10/2005 | Smith et al. | |
| 6,972,295 B2 | 12/2005 | Hagmann et al. | |
| 7,514,422 B2 | 4/2009 | Smith et al. | |
| 7,977,329 B2 | 7/2011 | Smith et al. | |

FOREIGN PATENT DOCUMENTS

| | | |
|---|---|---|
| CA | 1090797 | 12/1980 |
| CA | 2197789 | 8/1995 |
| CH | 500194 | 1/1971 |
| DE | 1944121 | 3/1970 |
| DE | 3315106 A1 | 11/1983 |

(Continued)

OTHER PUBLICATIONS

Barnes, "Pharmacological Strategies for Relapse Prevention in Schizophrenia," Psychiatry 3(10): 37-40 (2004).
Bickerdike, "5-HT$_{2C}$ Receptor Agonists as Potential Drugs for the Treatment of Obesity," Current Topics in Medicinal Chemistry, vol. 3, pp. 885-897 (2003).
Chahal et al., IDdb Meeting Report 2000, May 17-18.
Chang et al., "Dopamine Receptor Binding Properties of Some 2,3,4,5-tetrahydro-1*H*-3-benzazepine-7-OLS with Non-Aromatic Substituents in the 5-Position," Bioorganic & Medicinal Chemistry Letters, 2(5):399-402 (1992).

(Continued)

Primary Examiner — Bruck Kifle

(57) ABSTRACT

The present invention relates to novel compounds of Formula (I):

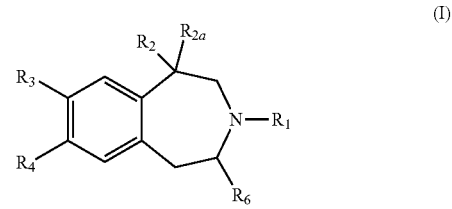

which act as 5HT$_{2C}$ receptor modulators. These compounds are useful in pharmaceutical compositions whose use includes the treatment of obesity.

2 Claims, 7 Drawing Sheets

(56) References Cited

FOREIGN PATENT DOCUMENTS

| | | |
|---|---|---|
| EP | 0007070 B1 | 1/1983 |
| EP | 0161350 A1 | 11/1985 |
| EP | 0174118 A2 | 3/1986 |
| EP | 0080779 B1 | 7/1986 |
| EP | 0096838 B1 | 4/1987 |
| EP | 0285287 A3 | 10/1988 |
| EP | 0285919 A1 | 10/1988 |
| EP | 0987235 B1 | 3/2003 |
| EP | 1074549 B1 | 11/2003 |
| GB | 1221324 | 2/1971 |
| GB | 1225053 | 3/1971 |
| GB | 1268243 | 3/1972 |
| GB | 1599705 | 10/1981 |
| JP | 05-339263 | 12/1993 |
| JP | 06-298746 | 10/1994 |
| JP | 08-134048 | 5/1996 |
| JP | 09-030960 | 2/1997 |
| JP | 90-987258 | 3/1997 |
| NL | 7807819 | 1/1980 |
| WO | WO 88/07858 A1 | 10/1988 |
| WO | WO 91/19698 A1 | 12/1991 |
| WO | WO 93/00094 A2 | 1/1993 |
| WO | WO 95/13274 A1 | 5/1995 |
| WO | WO 96/04271 A1 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/062392 A2 | 7/2003 |
| WO | WO 03/086306 A2 | 10/2003 |
| WO | WO 2004/037788 A1 | 5/2004 |
| WO | WO 2005/003096 A1 | 1/2005 |
| WO | WO 2005/019179 A2 | 3/2005 |
| WO | WO 2005/042490 A1 | 5/2005 |
| WO | WO 2005/042491 A1 | 5/2005 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2007/120517 A2 | 10/2007 |

OTHER PUBLICATIONS

Deady et al., "Synthesis of Some Tetrahydro-2- and 3-benzazepines, and of Hexahydro-3-benzazocine," JCS Perkins I, 782-3 (1973).

Di Chiara, "Nucleus Accumbens Shell and Core Dopamine: Differential Role in Behavior and Addiction," Behavioural Brain Research, 137: 75-114 (2002).

Di Chiara et al, "Reward System and Addiction: What Dopamine Does and Doesn't Do," Current Opinion in Pharmacology 7:69-76 (2007).

Di Giovanni et al., "Serotonin/dopamine Interaction—Focus on 5-HT$_{2C}$ Receptor, A New Target of Psychotropic Drugs," Indian Journal of Experimental Biology, vol. 40, pp. 1344-1352 (2002).

Di Matteo et al., "Role of 5-HT$_{2C}$ Receptors in the Control of Central Dopamine Function," Trends in Pharmacological Sciences 22(5):229-232 (2001).

Diagnostic and Statistical Manual of Mental Disorders, 4th edition, Text Revision, Washington, DC, American Psychiatric Association, 2000.

Enza Lacivita et al., "Selective Agents for Serotonin$_{2C}$ (5-HTC$_{2C}$) Receptor," Current Topics in Medicinal Chemistry, vol. 6, pp. 1927-1970 (2006).

Flannery-Schroeder, "Reducing Anxiety to Prevent Depression," Am. J. Prev. Med. 31 (6S1):S136-S142 (2006).

Fuchs et al., "Total Synthesis of (+/−)-Lennoxamine and (+/−)-Aphanorphine by Intramolecular Electrophilic Aromatic Substitution Reactions of 2-Amidoacroleins," Organic Letters, 2001, pp. 3923-3925, 3(24).

Gallant et al., "U-22,394A: A Controlled Evaluation in Chronic Schizophrenic Patients," Current Therapy Research 9(11):579-81(1967).

Gardent et al., "Sur Quelques Propriétés de l'Amino-2 Bromo-4 1H Benzazépine-3 et de ses dérivés," Bulletin de La Société Chimique de France, 2:600-5 (1968).

Gerace et al., "Predictors of Weight Increases over 7 Years in Fire Fighters and Paramedics," Preventive Medicine 25:593-600 (1996).

Gobert et al., "Serotonin$_{2C}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).

Gombar et al., "Pharmacokinetics of a series of 6-chloro-2, 3, 4, 5-tetrahydro-3-substituted-1H-3-benzazepines in rats," Drug Metab. Disposition 16:367-372 (1988).

Greene et al., Protective Groups in Organic Syntheses, 2nd Ed., Wiley and Sons, NY (1991).

Griesser, "Polymorphism in the Pharmaceutical Industry," ed. Rolf Hilfiker, Wiley-VCH Verlag GmbH & Co.: pp. 211-233 (2006).

Guillory, "Polymorphism in Pharmaceutical Solids," ed. Harry G. Brittain, Marcel Dekker, Inc., vol. 95: pp. 202-209 (1999).

Halford et al, "Serotonergic Drugs: Effects on Appetite Expression and Use for the Treatment of Obesity," Drugs 67(1):27-55 (2007).

Halford, "Obesity Drugs in Clinical Development," Current Opinion in Investigational Drugs 7(4):312-318 (2006).

Hassine-Coniac et al., "Preparation et propriétés d'aldéhydes dans la série de la benzazépine-3," Bulletin de La Société Chimique de France, 11:3985-92 (1971).

Hazebroucq, "Accès A Des I-H, Tétrahydro-2, 3, 4, 5 Benzazèpines-3 one-1 et a Des Hexahydro Imidazo Isoquinoléines," Ann. Chim., pp. 221-254 (1966).

Hester et al., "Azepinoindoles. I. Hexahydroazepino[4,5-b]indoles," J. Med. Chem. 11(1): 101-106 (1968).

Higgins et al, "Serotonin and drug reward: focus on 5-HT$_{2C}$ receptors," European Journal of Pharmacology, 480:151-162 (2003).

Hitzig, "Combined Serotonin and Dopamine Indirect Agonists Correctalcohol Craving and Alcohol-Associated Neuroses," Journal of Substance Abuse Treatment, 11(5):489-90 (1994).

Im et al., "Positive Allosteric Modulator of the Human 5-HT$_{2C}$ Receptor," Molecular Pharmacology, 64: 78-84 (2003).

Jandacek, "APD-356 (Arena)," Current Opinion in Investigational Drugs 6(10):1051-1056 (2005).

Jenck et al., "Antiaversive effects of 5HT$_{2C}$ receptor agonists and fluoxetine in a model of panic-like anxiety in rats," European Neuropsychopharmacology 8:161 (1998).

Jensen, "Potential Role of New Therapies in Modifying Cardiovascular Risk in Overweight Patients with Metabolic Risk Facts," Obesity 14 (Suppl. 3):143S-149S (2006).

Karasu et al., (2000) Practice Guideline for the Treatment of Patients with Major Depressive Disorder.

Koplan et al., "Preventing Childhood Obesity: Health in the Balance, Executive summary," (2005).

Ladd et al., "Synthesis of a Dopaminergic Binding of 2-Aryldopamine Analogues: Phenethylamines, 3-Benzazepines, and 9-(Aminomethyl) Fluorenes," B209 J. Med. Chem., 29(10):1904-12 (1986).

Lam et al., (1999) (eds) Canadian Consensus Guidelines for the Treatment of Seasonal Affective Disorder, Clinical & Academic Publishing, Vancouver, BC, Canada.

Lennon et al., "Azabenzocycloheptenones. Part XVIII. Amines and Amino-ketones of the Tetrahydro-3-benzazepin-1-one Series," J.C. S. Perkin I,7:622-6 (1975).

Macdonald, et al., "Design and Synthesis of trans-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and Selective Dopamine D$_3$ Receptor Antagonist," J. Med. Chem., 46(23):4952-64 (2003).

(56) References Cited

OTHER PUBLICATIONS

Moline et al., "Postpartum Depression: A Guide for Patients and Families," Expert Consensus Guidelines Series—Treatment of Depression in Woman 2001, March: 112-113 (2001).

Muller et al., "Intracellular 5-$HT_{2C}$-receptor Dephosphorylation: A New Target for Treating Drug Addiction," Trends in Pharmacological Sciences, 27(9):455-58 (2006).

Nagase et al., "An anhydrous polymorphic form of trehalose," Carbohydrate Research 337(2),167-173 (2002).

Navarro-Vasquez et al., "A Study of Aryl Radical Cyclization in Enaminone Esters," J. Org. Chem. 67:3213-20 (2002).

Niendam et al, "Neurocognitive Performance and Functional Disability in the Psychosis Prodrome," Schizophrenia Research 84:100-111 (2006).

Orito et al., "Benzolactams-I: Alkylation of 1,2,4,5-tetrahydro-3-methyl-3H-3-benzazepin-2-one with sodium hydride and alkyl halide," Tetrahedron 36:1017-1021 (1980) Pergamon Press Ltd.

Orito et al. Hokkaido Daigaku Kogakubu Kenkyu Hokoku (1979),(96), 41-44.

Orito et al., "Total Synthesis of Pseudo Type of Protopine Alkaloids," Heterocycles 14(1), 11-14 (1980).

Pauvert et al., "Silver Nitrate-Promoted Ring Enlargement of 1-Tribromomethy1-1,2-dihydro- and 1-Tribromomethyl-1,2,3,4-tetrahydro-isoquinoline Derivatives: Application to the Synthesis of the Anti-anginal Zatebradine," Tetrahedron Letters, 44:4203-6 (2003), Pergamon Press Ltd.

Pawan et al, "Preliminary study on the effects of fenfluramine derivative, 'S992' in man," British Journal of Pharmacology, 41(2): 416P-417P (1971).

Pecherer et al., "The Synthesis of Some 7- and 7,8-substituted 2,3,4,5-tetrahydro-1H-3-benzazepines," J. Heterocyclic Chemistry 8(51:779-783 (1971).

Perry et al., "Prospective study of risk factors for development on non-insulin dependent diabetes in middle aged British men," BMJ (1995) 310:560-564.

Piesla et al., (2001) Schizophrenia Research 49:95.

Porras et al., "5-$HT_{2A}$ and 5-$HT_{2C/2B}$ Receptor Subtypes Modulate Dopamine Release Induced in Vivo by Amphetamine and Morphine in Both the Rat Nucleus Accumbens and Striatum," Neuropsychopharmacology 26: 311-324(2002).

Prous Science Integrity entry 156186, (2007).

Prous Science Integrity entry 354056, (2007).

Rothman, "Treatment of Alcohol and Cocaine Addiction by the Combination of Pemoline and Fenfluramine: A Preliminary Case Series," Journal of Substance Abuse Treatment, 12(6):449-53 (1995).

Schaffner et al., "Preventing Severe Mental Illnesses—New Prospects and Ethical Challenges," Schizophrenia Research 51:3-15 (2001).

Schlademan et al., "Synthesis of oxo- and 1-hydroxy-azobenzocycloalkanes," J. Chem. Soc. Perkin Transacts. (1972) 2:213-215.

Smith et al., "Discovery and Structure—Activity Relationship of (1R)-8-Chloro-2,3,4,5-tetrahydro-I-methyl-1H-3-benzazepine (Lorcaserin), a Selective Serotonin 5-$HT_{2C}$, Receptor Agonist for the Treatment of Obesity," [retrieved on Dec. 21, 2007]. Retrieved from the Internet.<Url:http://pubs.acs.orgijournals/jmcmar/index.html>.

Smith et al., "Discovery and SAR of New Benzazepines as Potent and Selective 5-HT2C Receptor Agonists for the Treatment of Obesity," Bioorganic & Medicinal Chemistry Letters 15(5):1467-1470 (2005).

Tietze et al., "Efficient synthesis of 2,3,4,5-tetrahydro-1H-3-benzazepines by intramolecular heck reaction," Institut fur Organische Chemie der Universitat Gottingen, Tammannstra e 2, D-3400 Gottingen, Germany.

Tsuang et al., "Towards the Prevention of Schizophrenia," B245 Biol. Psychiatry 48:349-356 (2000).

Van Oekelen et al., "5-$HT_{2A}$ and 5-$HT_{2C}$ Receptors and Their Atypical Regulation Properties," Life Sciences, vol. 72, pp. 2429-2449 (2003).

Vink et al., "Risk Factors for Anxiety and Depression in the Elderly: A Review," J. Affect. Disord., doi:10.1016/j.jad.2007.06.005, 16 pages (2007).

Williams, Chemistry Demystified 123 (2003).

Wise, "Addiction Becomes a Brain Disease," Neuron, 26: 27-33 (2000).

Wisner et al., "Postpartum Depression," N. Engl. J. Med., 347(3):194-199 (2002).

Woods et al., "Annual Report: Evaluation of New Compounds for Opioid Activity," National Institute on Drug Abuse, Proceedings of the 41st Annual Scientific Meeting (1979) pp. 356-401.

Yoshinaga et al., "Prevention of Mildly Overweight Children from Development of More Overweight Condition," *Prevention Medicine* 38:172-174 (2004).

5HT$_{2C}$ RECEPTOR MODULATORS

CROSS-REFERENCE TO RELATED APPLICATIONS

This application is a continuation of U.S. Ser. No. 13/523,805 filed Jun. 14, 2012, now U.S. Pat. No. 8,273,734 which is a continuation of U.S. Ser. No. 13/118,126 filed May 27, 2011, now U.S. Pat. No. 8,270,158 issued Jun. 26, 2012, which is a continuation of U.S. Ser. No. 11/599,050, filed Nov. 14, 2006, now U.S. Pat. No. 7,977,329 issued Jul. 12, 2011, which is a continuation of U.S. Ser. No. 10/917,979, filed Aug. 13, 2004, now U.S. Pat. No. 7,514,422 issued Apr. 7, 2009, which in turn is a continuation of U.S. Ser. No. 10/410,991, filed Apr. 10, 2003, now U.S. Pat. No. 6,953,787 issued Oct. 11, 2005, which in turn claims priority benefit of U.S. Provisional Application No. 60/372,058, filed Apr. 12, 2002; U.S. Provisional Patent Application No. 60/405,495, filed Aug. 23, 2002 and U.S. Provisional Patent Application No. 60/434,607, filed Dec. 18, 2002 which are hereby incorporated by reference in their entirety.

FIELD OF THE INVENTION

The present invention relates to compounds which act as modulators of 5HT$_{2C}$ receptors, compositions including the compounds, and methods of using the compounds.

BACKGROUND OF THE INVENTION

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also, and this can be a more important factor, the decrease in activity in most people's lives. In the last 10 years there has been a 30% increase in the incidence of obesity in the USA and that about 30% of the population of the USA is now considered obese.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$ (see TABLE below).

| CLASSIFICATION OF WEIGHT BY BODY MASS INDEX (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and 30% in females.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However many patients find this difficult and need additional help from drug therapy to maintain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have recently been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in health and in psychiatric disorders. 5-HT has been implicated in the regulation of feeding behavior for some time. 5-HT appears to work by inducing a feeling of fullness or satiety so eating stops earlier and fewer calories are consumed. It has been shown that a stimulatory action of 5-HT on the 5-HT$_{2C}$ receptor plays an important role in the control of eating and in the anti-obesity effect of d-fenfluramine. As the 5-$HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-$HT_{2C}$ receptor agonist can be a more effective and safe anti-obesity agent. Also, 5-$HT_{2C}$ knockout mice are overweight with cognitive impairment and susceptibility to seizure.

It is believed that $5HT_{2C}$ may play a role in obsessive compulsive disorder, some forms of depression, and epilepsy. Accordingly, agonists can have anti-panic properties, and properties useful for the treatment of sexual dysfunction.

In sum, the $5HT_{2C}$ receptor is a validated and well-accepted receptor target for the treatment of obesity and psychiatric disorders, and it can be seen that there is a need for selective $5HT_{2C}$ agonists which safely decrease food intake and body weight. The present invention is directed to these, as well as other, important ends.

SUMMARY OF THE INVENTION

The present invention, in one aspect, relates to compounds represented by Formula (I):

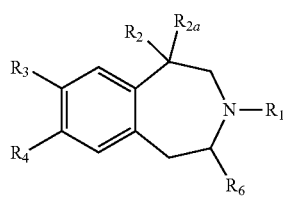

wherein:
$R_1$ is H or $C_{1-8}$ alkyl;
$R_2$ is $C_{1-8}$ alkyl, —$CH_2$—O—$C_{1-8}$ alkyl, —C(=O)—O—$C_{1-8}$ alkyl, —C(=O)—NH—$C_{1-8}$ alkyl, or $CH_2OH$;
$R_{2a}$ is H or $CH_3$;
or $R_2$ and $R_{2a}$ together form —$CH_2$—$CH_2$—;
$R_3$ and $R_4$ are each independently H, halogen, perhalo alkyl, (preferably $CF_3$), CN, $OR_5$, $SR_5$, $NHR_5$, $N(R_5)_2$, aryl, or heteroaryl, wherein said aryl can be optionally substituted with up to two substituents selected from $C_{1-8}$ alkyl, halogen and alkoxy, and said heteroaryl can be optionally substituted with up to two substituents selected from halogen and $C_{1-8}$ alkyl;
or $R_3$ and $R_4$ together with the atoms to which they are attached can form a 5- or 6-member heterocyclic ring having one O atom;
each $R_5$ is independently $C_{1-8}$ alkyl, $C_{1-8}$ alkenyl, aryl, heteroaryl, arylalkyl, heteroarylalkyl or perhaloalkyl; and
$R_6$ is H or $C_{1-8}$ alkyl; or a pharmaceutically acceptable salt, solvate or hydrate thereof
provided that:
(A) if $R_2$ is methyl and $R_1$ and $R_3$ are both H, then $R_4$ is not thiazole, substituted thiazole or a thiazole derivative:
(B) if $R_6$ is other than H, then neither $R_3$ nor $R_4$ can be H;
(C) if $R_1$ and $R_2$ are methyl, and $R_4$ is H, then $R_3$ cannot be $NHR_5$ or $N(R_5)_2$;
(D) if $R_1$ and $R_2$ are methyl, and $R_4$ is H, then $R_3$ cannot be imidazole, substituted imidazole, or an imidazole derivative; and
(E) if $R_3$ is OH, and $R_1$ is methyl then $R_2$ cannot be cyclopentyl, —$CH_2$-cyclohexyl, cyclopropylmethyl, or cyclohexyl.

In some embodiments of the compounds and methods of the invention, when $R_1$, $R_{2a}$, $R_3$ and $R_6$ are H and $R_2$ is methyl, then $R_4$ cannot be a chlorine atom.

In other embodiments of the compounds and methods of the invention, when $R_1$, $R_{2a}$, $R_3$ and $R_6$ are H and $R_2$ is methyl, then $R_4$ can be a chlorine atom.

In some alternate embodiments of the compounds of Formula (I), if $R_4$ is $OR_5$, then $R_2$ cannot be alkyl.

In some embodiments of the compounds of Formula (I), $R_1$ is H. In some embodiments of the compounds of Formula (I), $R_1$ is $C_{1-8}$ alkyl. In some embodiments of the compounds of Formula (I), $R_1$ is methyl. In some embodiments of the compounds of Formula (I), $R_1$ is n-propyl.

In some embodiments of the compounds of Formula (I), $R_2$ is $C_{1-8}$ alkyl. In some embodiments of the compounds of Formula (I), $R_2$ is methyl. In some embodiments of the compounds of Formula (I), $R_2$ is ethyl. In some embodiments of the compounds of Formula (I), $R_2$ is isopropyl. In some embodiments of the compounds of Formula (I), $R_2$ and $R_{2a}$ together form —$CH_2$—$CH_2$—.

In some embodiments of the compounds of Formula (I), $R_3$ is halogen. In some embodiments of the compounds of Formula (I), $R_3$ is chlorine. In some embodiments of the compounds of Formula (I), $R_3$ is bromine. In some embodiments of the compounds of Formula (I), $R_3$ is iodine. In some embodiments of the compounds of Formula (I), $R_3$ is perhaloalkyl. In some embodiments of the compounds of Formula (I), $R_3$ is $CF_3$. In some embodiments of the compounds of Formula (I), $R_3$ is a 5-membered heteroaryl ring having up to two heteroatoms selected from O, N and S. In some embodiments, $R_3$ is a radical derived from thiophenyl, furanyl, pyrrolyl, pyrazolyl or imidazolyl.

In some embodiments of the compounds of Formula (I), $R_4$ is perhaloalkyl. In some embodiments of the compounds of Formula (I), $R_4$ is $CF_3$. In some embodiments of the compounds of Formula (I), $R_4$ is —$OR_5$. In some embodiments $R_5$ is methyl, ethyl, n-propyl, isopropyl or allyl. In some embodiments of the compounds of Formula (I), $R_5$ is methyl or allyl. In some embodiments of the compounds of Formula (I), $R_4$ is a 5-membered heteroaryl ring having up to two heteroatoms selected from O, N and S, and up to two substituents selected from halogen and $C_{1-8}$ alkyl. In some embodiments, $R_4$ is a radical derived from thiophenyl, furanyl, pyrrolyl, pyrazolyl or imidazolyl, which can optionally be mono- or di-substituted selected from halogen or methyl. In some embodiments of the compounds of Formula (I), $R_4$ is phenyl optionally substituted with up to two substituents selected from $C_{1-8}$ alkyl, halogen, and alkoxy. In some embodiments of the compounds of Formula (I), $R_3$ and $R_4$ taken together form —O—CH=C($CH_3$)—.

In some embodiments of the compounds of Formula (I), $R_3$ is halogen and $R_4$ is —$OR_5$ wherein $R_5$ is $C_{1-8}$ alkyl. In some embodiments of the compounds of Formula (I), $R_3$ is chlorine and $R_4$ is —$OR_5$ wherein $R_5$ is $C_{1-8}$ alkyl. In some embodiments of the compounds of Formula (I), $R_3$ is bromine and $R_4$ is —$OR_5$ wherein $R_5$ is $C_{1-8}$ alkyl. In some embodiments of the compounds of Formula (I), $R_3$ is iodine and $R_4$ is —$OR_5$ wherein $R_5$ is $C_{1-8}$ alkyl. In some embodiments of the compounds of Formula (I), $R_3$ is halogen and $R_4$ is methoxy. In some embodiments of the compounds of Formula (I), $R_3$ is halogen and $R_4$ is allyloxy.

In some embodiments of the compounds of Formula (I), $R_3$ is H and $R_4$ is a 5-membered heteroaryl ring having up to two heteroatoms selected from O, N and S, and up to two substituents selected from halogen and $C_{1-8}$ alkyl, or $R_4$ is phenyl optionally substituted with up to two substituents selected from $C_{1-8}$ alkyl, halogen, and alkoxy.

In some embodiments of the compounds of Formula (I), $R_3$ is H and $R_4$ is a disubstituted pyrrazole or monohalo-substituted phenyl. In some such embodiments of the compounds of Formula (I), the substitutents of the pyrrazole are bromine and methyl.

In some embodiments of the compounds of Formula (I), $R_3$ is $OR_5$. In some embodiments of the compounds of Formula (I), $R_3$ is $OR_5$ wherein $R_5$ is $C_{1-8}$ alkyl. In some embodiments of the compounds of Formula (I), $R_3$ is $OR_5$ wherein $R_5$ is aryl. In some embodiments of the compounds of Formula (I), $R_3$ is $OR_5$ wherein $R_5$ is heteroaryl. In some embodiments of the compounds of Formula (I), $R_3$ is $OR_5$ wherein $R_5$ is arylalkyl. In some embodiments of the compounds of Formula (I), $R_3$ is $OR_5$ wherein $R_5$ is arylmethyl. In some embodiments of the compounds of Formula (I), $R_3$ is $OR_5$ wherein $R_5$ is heteroarylalkyl. In some embodiments of the compounds of Formula (I), $R_3$ is $OR_5$ wherein $R_5$ is heteroarylmethyl. In some embodiments of the compounds of Formula (I), $R_3$ is $OR_5$ wherein $R_5$ is perhaloalkyl. In some embodiments of the compounds of Formula (I), $R_3$ is $OR_5$ wherein $R_5$ is allyl.

In some embodiments of the compounds of Formula (I):
$R_2$ is methyl, ethyl, isopropyl, or $CH_2OH$; or $R_2$ and $R_{28}$ taken together form —$CH_2$—$CH_2$—;
$R_3$ is H, halogen, or a 5-membered heteroaryl ring having up to two heteroatoms selected from O, N and S, and up to two substituents selected from halogen and $C_{1-8}$ alkyl;
$R_4$ is H, alkoxy, a 5-membered heteroaryl ring having up to two heteroatoms selected from O, N and S and up to two substituents selected from halogen and $C_{1-8}$ alkyl, or phenyl optionally substituted with up to two substituents selected from $C_{1-8}$ alkyl, halogen, and alkoxy;
or $R_3$ and $R_4$ taken together form O—CH=C($CH_3$)—; and
$R_4$ is H or methyl; or a pharmaceutically acceptable salt, solvate or hydrate thereof.

In some embodiments of the compounds of Formula (I):
$R_2$ is methyl, ethyl, isopropyl, or $CH_2OH$; or $R_2$ and $R_{2a}$ taken together form —$CH_2$—$CH_2$—;
$R_3$ is chlorine, bromine, or iodine;
$R_4$ is alkoxy; and
$R_{15}$ is H or methyl; or a pharmaceutically acceptable salt, solvate or hydrate thereof.

In some embodiments of the compounds of Formula (I):
$R_1$ is H;
$R_2$ is methyl;
$R_3$ is H, chlorine, bromine, or thiophene;
$R_4$ is alkoxy, pyrrazoly-3-yl or phenyl wherein said pyrrazole optionally has up to two substituents selected from halogen and $C_{1-8}$ alkyl, and said phenyl optionally has a single halogen substitutent; and
$R_6$ is H; or a pharmaceutically acceptable salt, solvate or hydrate thereof.

In some embodiments of the compounds of Formula (I), the compound is a member of the group consisting of: 8-Bromo-7-hydroxy-1-methyl-2,3,4,5-tetrahydro-1H-3-benzazepine; 7-Allyloxy-8-bromo-1-methyl-2,3,4,5-tetrahydro-1H-3-benzazepine; 7-Benzyloxy-8-bromo-1-methyl-2,3,4,5-tetrahydro-1H-3-benzazepine; 8-Bromo-7-ethoxy-1-methyl-2,3,4,5-tetrahydro-1H-3-benzazepine; 8-Bromo-7-isopropoxy-1-methyl-2,3,4,5-tetrahydro-1H-3-benzazepine; N-Propyl-8-bromo-7-methoxy-1-methyl-2,3,4,5-tetrahydro-1H-3-benzazepine; 7-Hydroxy-8-iodo-1-methyl-2,3,4,5-tetrahydro-1H-3-benzazepine; 7-Allyloxy-8-iodo-1-methyl-2,3,4,5-tetrahydro-1H-3-benzazepine; 3,5-Dimethyl-6,7,8,9-tetrahydro-5H-1-oxa-7-aza-cycloheptaindene; 7-Allyloxy-8-chloro-1-methyl-2,3,4,5-tetrahydro-1H-3-benzazepine; 7-Methoxy-1-methyl-8-(2-thienyl)-2,3,4,5-tetrahydro-1H-3-benzazepine; 8-Cyano-7-methoxy-1-methyl-2,3,4,5-tetrahydro-1H-3-benzazepine; 8-bromo-1-cyclopropyl-7-methoxy-2,3,4,5-tetrahydro-1H-3-benzazepine; 8-bromo-1-hydroxymethyl-7-methoxy-2,3,4,5-tetrahydro-1H-3-benzazepine; 8-Bromo-1-isopropyl-7-methoxy-2,3,4,5-tetrahydro-1H-3-benzazepine; 8-Bromo-7-hydroxy-1-isopropyl-2,3,4,5-tetrahydro-1H-3-benzazepine; 7-Allyloxy-8-bromo-1-isopropyl-2,3,4,5-tetrahydro-1H-3-benzazepine; 8-Bromo-7-methoxy-1,4-dimethyl-2,3,4,5-tetrahydro-1H-3-benzazepine; 7-Allyloxy-8-bromo-1,4-dimethyl-2,3,4,5-tetrahydro-1H-3-benzazepine; 7-(2-Methyl-2H-pyrazol-3-yl)-1-methyl-2,3,4,5-tetrahydro-1H-3-benzazepine; 7-(4-Bromo-2-methyl-2H-pyrazol-3-yl)-1-methyl-2,3,4,5-tetrahydro-1H-3-benzazepine; 7-(3-Chlorophenyl)-1-methyl-2,3,4,5-tetrahydro-1H-3-benzazepine; 7-(2-Chlorophenyl)-1-methyl-2,3,4,5-tetrahydro-1H-3-benzazepine; 8-Chloro-1-hydroxy-2,3,4,5-tetrahydro-1H-3-benzazepine; 8-Bromo-1-methyl-2,3,4,5-tetrahydro-1H-3-benzazepine; 8-Fluoro-1-methyl-2,3,4,5-tetrahydro-1H-3-benzazepine; 7-Fluoro-1-methyl-2,3,4,5-tetrahydro-1H-3-benzazepine; 7,8-Dichloro-1-methyl-2,3,4,5-tetrahydro-1H-3-benzazepine; N-Methyl-8-chloro-1-methyl-2,3,4,5-tetrahydro-1H-3-benzazepine; 1-Methyl-7-trifluoromethoxy-2,3,4,5-tetrahydro-1H-3-benzazepine; 8-Iodo-1-methyl-7-trifluoromethoxy-2,3,4,5-tetrahydro-1H-3-benzazepine; N-Propyl-8-iodo-7-methoxy-1-methyl-2,3,4,5-tetrahydro-1H-3-benzazepine; 1-Ethyl-8-iodo-7-methoxy-2,3,4,5-tetrahydro-1H-3-benzazepine; 7-(3-Methoxyphenyl)-1-methyl-2,3,4,5-tetrahydro-1H-3-benzazepine; 7-(2,6-difluorophenyl)-1-methyl-2,3,4,5-tetrahydro-1H-3-benzazepine; 7-(2-fluorophenyl)-8-chloro-1-methyl-2,3,4,5-tetrahydro-1H-3-benzazepine; 7-(2-Trifluoromethylphenyl)-1-methyl-2,3,4,5-tetrahydro-1H-3-benzazepine; 7-(3-Trifluoromethylphenyl)-1-methyl-2,3,4,5-tetrahydro-1H-3-benzazepine; 7-(4-Trifluoromethylphenyl)-1-methyl-2,3,4,5-tetrahydro-1H-3-benzazepine; 8-(2-Chlorophenyl)-1-methyl-2,3,4,5-tetrahydro-1H-3-benzazepine; and 8-bromo-1-methoxymethyl-7-methoxy-2,3,4,5-tetrahydro-1H-3-benzazepine; or a pharmaceutically acceptable salt, solvate or hydrate thereof.

In some embodiments of the compounds of Formula (I), the compound is a member of the group consisting of: 8-Bromo-7-methoxy-1-methyl-2,3,4,5-tetrahydro-1H-3-benzazepine; 8-Chloro-7-methoxy-1-methyl-2,3,4,5-tetrahydro-1H-3-benzazepine; 8-Iodo-7-methoxy-1-methyl-2,3,4,5-tetrahydro-1H-3-benzazepine; N-Methyl-8-bromo-7-methoxy-1-methyl-2,3,4,5-tetrahydro-1H-3-benzazepine; 8-Bromo-1-ethyl-7-methoxy-2,3,4,5-tetrahydro-1H-3-benzazepine; 8-Chloro-1-ethyl-7-methoxy-2,3,4,5-tetrahydro-1H-3-benzazepine; 8-Iodo-1-ethyl-7-methoxy-2,3,4,5-tetrahydro-1H-3-benzazepine; 7-Methoxy-1-methyl-8-trifluoromethyl-2,3,4,5-tetrahydro-1H-3-benzazepine; and 7-Methoxy-1-methyl-8-pentafluoroethyl-2,3,4,5-tetrahydro-1H-3-benzazepine; or a pharmaceutically acceptable salt, solvate or hydrate thereof.

In some embodiments of the compounds of Formula (I), the compound is a member of the group consisting of: 8-Chloro-1-methyl-2,3,4,5-tetrahydro-1H-3-benzazepine; 8-Bromo-1-methyl-2,3,4,5-tetrahydro-1H-3-benzazepine; 8-Iodo-1-methyl-2,3,4,5-tetrahydro-1H-3-benzazepine; 8-Trifluoromethyl-1-methyl-2,3,4,5-tetrahydro-1H-3-benzazepine; 8-Trifluoromethyl-1-ethyl-2,3,4,5-tetrahydro-1H-3-benzazepine; 8-Chloro-1-ethyl-2,3,4,5-tetrahydro-1H-3-benzazepine; 8-Bromo-1-ethyl-2,3,4,5-tetrahydro-1H-3- benzazepine; 8-Iodo-1-ethyl-2,3,4,5-tetrahydro-1H-3-benzazepine; 7,8-Dichloro-1-methyl-2,3,4,5-tetrahydro-1H-3-benzazepine; 7,8-Dichloro-1-ethyl-2,3,4,5-tetrahydro-1H-3-benzazepine; 8-Chloro-7-fluoro-1-methyl-2,3,4,5-tetrahydro-1H-3-benzazepine; and 8-Chloro-7-fluoro-1-ethyl-2,3,4,5-tetrahydro-1H-3-benzazepine; or a pharmaceutically acceptable salt, solvate or hydrate thereof.

The present invention also provides compositions comprising one or more compounds of the invention, and one or more pharmaceutically acceptable carriers.

The present invention further provides methods of modulating a $5HT_{2C}$ receptor comprising contacting said receptor with a pharmaceutically effective amount of a compound or composition of the invention. Preferably, said compound is an agonist of said receptor.

The present invention further provides methods of prophylaxis or treatment of disorders of the central nervous system; damage to the central nervous system; cardiovascular disorders; gastrointestinal disorders; diabetes insipidus, and sleep apnea comprising administering to a patient in need of such prophylaxis or treatment an effective dose of a compound of the invention.

In some embodiments, the disorders of the central nervous system include depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related mental disorders, chronic fatigue syndrome, drug and alcohol addiction, obesity, bulimia, anorexia nervosa and premenstrual tension. In some embodiments, the disorders of the central nervous system is obesity.

In some embodiments, the damage to the central nervous system is by trauma, stroke, neurodegenerative diseases or toxic or infective CNS diseases, including encephalitis and meningitis.

In some embodiments, the cardiovascular disorder thrombosis. In further embodiments, the gastrointestinal disorder is dysfunction of gastrointestinal motility.

The present invention further provides methods of decreasing food intake of a mammal comprising administering to said mammal a pharmaceutically effective amount of a compound or composition of the invention.

The present invention further provides methods of inducing satiety in a mammal comprising administering to said mammal a pharmaceutically effective amount of a compound or composition of the invention.

The present invention further provides methods of controlling weight gain of a mammal comprising administering to said mammal a pharmaceutically effective amount of a compound or composition of the invention.

The present invention further provides methods of treating obesity comprising administering to a patient in need of such treatment a pharmaceutically effective amount of a compound or composition of the invention.

In some embodiments, some of the foregoing methods of the invention further comprising the step of identifying a subject, said subject being in need of decreasing food intake, controlling weight gain, or treating obesity, wherein said identifying step is performed prior to administering to said subject said pharmaceutically effective amount of said compound or composition of the invention.

One aspect of the present invention pertains to a compound of Formula (I) for use in a method of treatment of the human or animal body by therapy.

One aspect of the present invention pertains to a compound of Formula (I) for use in a method of prophylaxis or treatment of disorders of the central nervous system; damage to the central nervous system; cardiovascular disorders; gastrointestinal disorders; diabetes insipidus, and sleep apnea. In some embodiments the disorders of the central nervous system are selected the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In some embodiments the disorder is obesity.

One aspect of the present invention pertains to a compound of Formula (I) for the manufacture of a medicament for use in the prophylaxis or treatment of disorders of the central nervous system; damage to the central nervous system; cardiovascular disorders; gastrointestinal disorders; diabetes insipidus, and sleep apnea. In some embodiments the disorders of the central nervous system are selected the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In some embodiments the disorder is obesity.

In some embodiments, the invention provides methods for alleviation of a symptom of any of the diseases, conditions or disorders mentioned herein.

Applicants reserve the right to exclude any one or more of the compounds from any of the embodiments of the invention. Applicant additionally reserves the right to exclude any disorder from any of the embodiments of the invention.

DETAILED DESCRIPTION OF THE INVENTION

Figure 1A:
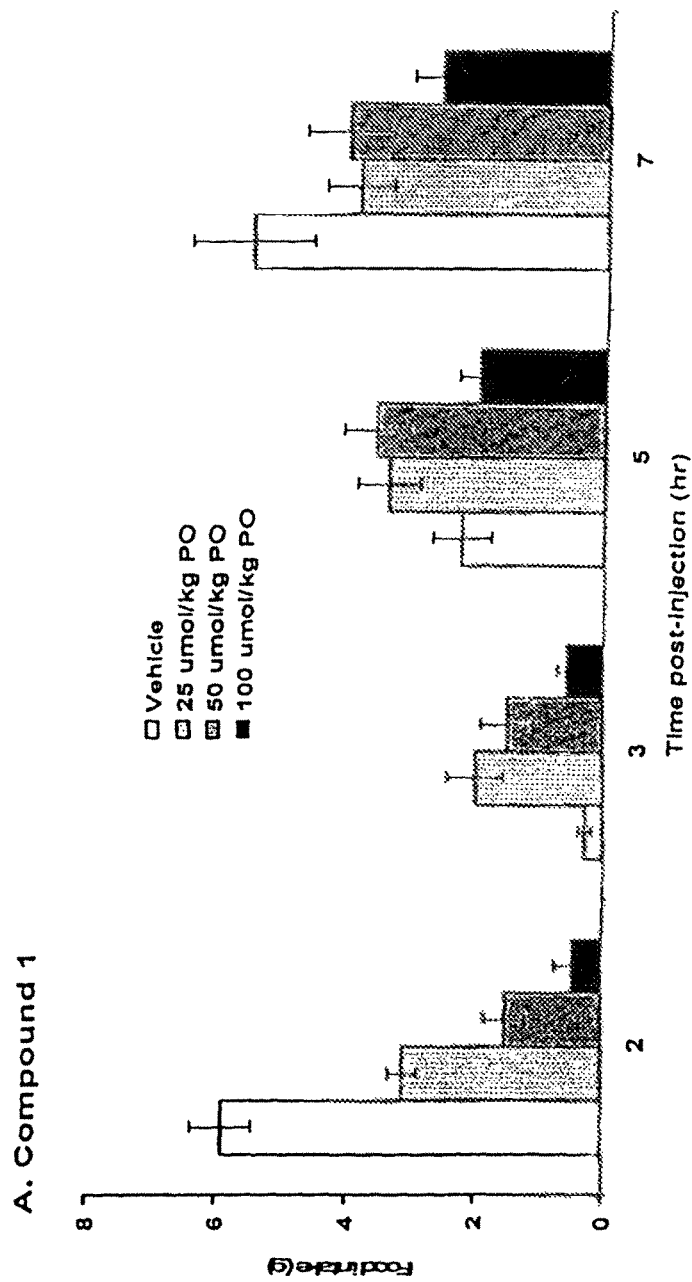
FIGS. 1A-1G illustrate the effects of seven different compounds of the invention on food intake in food-deprived rats.

The present invention relates to $5HT_{2C}$ receptor agonist compounds, methods of modulating $5HT_{2C}$ receptors by contacting the receptors with one or more compounds of the invention. The present invention also relates to methods of decreasing food intake, controlling weight gain, or treating obesity, using compounds of the invention.

The term "antagonist" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist. As used herein, the term "agonist" is intended to mean moieties that activate the intracellular response when they bind to the receptor, or enhance GTP binding to membranes. In the context of the present invention, a pharmaceutical composition comprising a $5HT_{2C}$ receptor agonist of the invention can be utilized for modulating the activity of the $5HT_{2C}$ receptor, decreasing food intake, inducing satiation (i.e., the feeling of fullness), controlling weight gain, treating obesity, decreasing body weight and/or affecting metabolism such that the recipient loses weight and/or maintains weight. Such pharmaceutical compositions can be used in the context of disorders and/or diseases where weight gain is a component of the disease and/or disorder such as, for example, obesity.

As used herein, the term "contact" or "contacting" shall mean bringing the indicated moieties together, whether in an in vitro system or an in vivo system. Thus, "contacting" an $5HT_{2C}$ receptor with a compound of the invention includes the administration of a compound of the invention to an animal having an $5HT_{2C}$ receptor, as well as, for example, introducing a compound of the invention into a sample containing a cellular or more purified preparation containing an $5HT_{2C}$ receptor.

Compounds of the invention include those having the Formula (I), shown below:

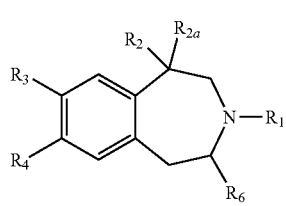

(I)

wherein:

$R_1$ is H or $C_{1-8}$ alkyl;

$R_2$ is $C_{1-8}$ alkyl, —$CH_2$—O—$C_{1-8}$ alkyl, —C(=O)—O—$C_{1-8}$ alkyl, —C(=O)—NH—$C_{1-8}$ alkyl, or $CH_2OH$;

$R_{2a}$ is H; or $R_2$ and $R_{2a}$ together form —$CH_2$—$CH_2$—;

$R_3$ and $R_4$ are each independently H, halogen, perhalo alkyl, (preferably $CF_3$), CN, $OR_5$, $SR_5$, $NHR_5$, $N(R_5)_2$, aryl, or heteroaryl, wherein said aryl can be optionally substituted with up to two substituents selected from $C_{1-8}$ alkyl, halogen and alkoxy, and said heteroaryl can be optionally substituted with up to two substituents selected from halogen and $C_{1-8}$ alkyl;

or $R_3$ and $R_4$ together with the atoms to which they are attached can form a 5- or 6-member heterocyclic ring having one O atom;

each $R_5$ is independently $C_{1-8}$ alkyl, $C_{1-8}$ alkenyl, aryl, heteroaryl, arylalkyl, heteroarylalkyl or perhaloalkyl; and $R_6$ is or $C_{1-8}$ alkyl; or a pharmaceutically acceptable salt, solvate or hydrate thereof provided that:
(A) if $R_2$ is methyl and $R_1$ and $R_3$ are both H, then $R_4$ is not thiazole, substituted thiazole or a thiazole derivative:
(B) if $R_6$ is other than H, then neither $R_3$ nor $R_4$ can be H;
(C) if $R_1$ and $R_2$ are methyl, and $R_4$ is H, then $R_3$ cannot be $NHR_5$ or $N(R_5)_2$;
(D) if $R_1$ and $R_2$ are methyl, and $R_4$ is H, then $R_3$ cannot be imidazole, substituted imidazole, or an imidazole derivative; and
(E) if $R_3$ is OH, and $R_1$ is methyl then $R_2$ cannot be cyclopentyl, —$CH_2$-cyclohexyl, cyclopropylmethyl, or cyclohexyl;
or provided (A), (B), (C), (D) above, and if $R_4$ is $OR_5$, then $R_2$ cannot be alkyl.

In some embodiments of the compounds and methods of the invention, when $R_1$, $R_{2a}$, $R_3$ and $R_6$ are H and $R_2$ is methyl, then $R_4$ cannot be a chlorine atom.

In other embodiments of the compounds and methods of the invention, when $R_1$, $R_{2a}$, $R_3$ and $R_6$ are H and $R_2$ is methyl, then $R_4$ can be a chlorine atom.

In some embodiments, if $R_4$ is $OR_5$, then $R_2$ cannot be cyclopentyl, —$CH_2$-cyclohexyl, 3,3-dimethyl-2-allyl, 3,3-dimethyl-2-methylallyl, 2-methylallyl, 2-butenyl, cyclopropylmethyl, cyclohexyl, or allyl.

It will be appreciated that compounds of Formula (I) may have one or more chiral centers, and exist as enantiomers or diastereomers. The invention is to be understood to extend to all such enantiomers, diastereomers and mixtures thereof, including racemates. Formula (I) and the formulae hereinafter are intended to represent all individual isomers and mixtures thereof, unless stated or shown otherwise.

As used herein, the term "alkyl" is intended to denote hydrocarbon groups including straight chain, branched and cyclic hydrocarbons, including for example but not limited to methyl, ethyl, n-propyl, isopropyl, cyclopropyl, n-butyl, sec-butyl, tert-butyl, cyclobutyl, cyclopropylmethyl, n-pentyl, isopentyl, tert-pentyl, cyclopentyl, cyclopentylmethyl, n-hexyl, cyclohexyl, and the like. Throughout this specification, it should be understood that the term alkyl is intended to encompass both non-cyclic hydrocarbon groups and cyclic hydrocarbon groups. In some embodiments of the compounds of the invention, alkyl groups are non-cyclic. In further embodiments, alkyl groups are cyclic, and in further embodiments, alkyl groups are both cyclic and noncyclic. Where no preference is specified, the term "alkyl" is intended to denote groups that are both cyclic and non-cyclic.

As used herein, the term "alkenyl" is intended to denote hydrocarbon compounds including straight chain, branched and cyclic hydrocarbons that contain at least one double bond, including for example but not limited to allyl, 2-methyl-allyl, 4-but-3-enyl, 4-hex-5-enyl, 3-methyl-but-2-enyl, cyclohex-2-enyl and the like.

As used herein, the term "halogen" has its normal meaning of period seven elements, including F, Cl, Br and I.

The term "alkoxy" is intended to denote substituents of the formula —O-alkyl, including —O-allyl. The term "lower" when used in connection with substituents such as alkyl indicates 6 carbons or less.

The term "arylalkyl" or "aralkyl" is intended to denote an alkyl group that bears an aryl substituent, for example a benzyl group. The term "alkylaryl" or "alkaryl" is intended to denote an aryl group that bears an alkyl substituent, for example a 4-methylphenyl group.

As used herein, the term "aryl" is intended to mean monocyclic and polycyclic aromatic groups. Although aryl groups can include as few as 3 carbon atoms, preferred aryl groups have 6 to about 14 carbon atoms, more preferably 6 to about 10 carbon, atoms. Examples of aryl groups include but are not limited to phenyl, naphthyl, anthracyl, phenanthryl and pyrenyl.

The term "heteroaryl" is intended to denote an aryl group that contains at least one, and preferably from one to four ring "hetero" (i.e., non-carbon, e.g., O, N or S) atom. Examples of "heteroaryl" groups are radicals derived from 5- and 6-member aryl ring compounds having from one to four nitrogen, sulfur and/or oxygen atoms, for example pyrrole, pyrazole, imidazole, triazole, tetrazole, pyridine, pyrimidine, furan, pyran, thiophene, benzimidazole, quinoline, isoquinoline, oxazole, thiazole, and thiadiazole.

As used herein the term heteroarylalkyl means an alkyl group that bears a heteroaryl substituent, for example a group having the structure —$CH_2$-pyrrole-2-yl.

The term "substituted thiazole" means a radical derived from thiazole that bears at least one substituent group. The term "thiazole derivative" means a fused ring system in which one of the fused rings is thiazole.

The term "substituted imidazole" means a radical derived from imidazole that bears at least one substituent group. The term "imidazole derivative" means a fused ring system in which one of the fused rings is imidazole.

In some embodiments of the invention, $R_4$ is $OR_5$. In some such embodiments, $R_2$ cannot be cyclopentyl, —$CH_2$-cyclohexyl, 3,3-dimethyl-2-allyl, 3,3-dimethyl-2-methylallyl, 2-butenyl, cyclopropylmethyl, cyclohexyl, or allyl. In further such embodiments, $R_2$ cannot be alkyl.

In some embodiments of the compounds of Formula (I), $R_3$ is halogen and $R_4$ is —$OR_5$. In some embodiments of the compounds of Formula (I), $R_5$ is allyl, 2-methyl-allyl, 4-but-3-enyl, 4-hex-5-enyl, 3-methyl-but-2-enyl or cyclohex-2-enyl. In some embodiments of the compounds of Formula (I), $R_5$ is methyl, ethyl, n-propyl, isopropyl or allyl. In some embodiments of the compounds of Formula (I), $R_5$ is methyl or allyl.

Certain substituents of the compounds disclosed herein can optionally be substituted, i.e., they can optionally bear further substituent groups. Some preferred substituent groups include halogen, lower alkyl (including but not limited to methyl, ethyl, isopropyl, cyclopropyl, tert-butyl, and methylcyclopropyl), alkoxy, mono-, di- or trihaloalkoxy (e.g., —O—$CX_3$ where X is halogen), —$(CH_2)_yNH_2$, —$(CH_2)_yN$-HBoc, —$N(R_{4a}(R_{4b})$, phenyl, methoxyphenyl) and naphthyl.

At various places in the present specification substituents of compounds of the invention are disclosed in groups or in ranges. It is specifically intended that the invention include each and every individual subcombination of the members of such groups and ranges. For example, the term "$C_{1-8}$ alkyl" is specifically intended to individually disclose methyl, ethyl, $C_3$ alkyl, $C_4$ alkyl, $C_5$ alkyl, $C_6$ alkyl, $C_7$ alkyl and $C_8$ alkyl.

In a preferred embodiment, the compounds of Formula (I) are selected from:

8-Bromo-7-hydroxy-1-methyl-2,3,4,5-tetrahydro-1H-3-benzazepine; 7-Allyloxy-8-bromo-1-methyl-2,3,4,5-tetrahydro-1H-3-benzazepine; 7-Benzyloxy-8-bromo-1-methyl-2,3,4,5-tetrahydro-1H-3-benzazepine; 8-Bromo-7-ethoxy-1-methyl-2,3,4,5-tetrahydro-1H-3-benzazepine; 8-Bromo-7-isopropoxy-1-methyl-2,3,4,5-tetrahydro-1H-3-benzazepine; N-Propyl-8-bromo-7-methoxy-1-methyl-2,3,4,5-tetrahydro-1H-3-benzazepine; 7-Hydroxy-8-iodo-1-methyl-2,3,4,5-tetrahydro-1H-3-benzazepine; 7-Allyloxy-8-iodo-1-methyl-2,3,4,5-tetrahydro-1H-3-benzazepine; 3,5-Dimethyl-6,7,8,9-tetrahydro-5H-1-oxa-7-aza-cycloheptaindene; 7-Allyloxy-8-chloro-1-methyl-2,3,4,5-tetrahydro-1H-3-benzazepine; 7-Methoxy-1-methyl-8-(2-thienyl)-2,3,4,5-tetrahydro-1H-3-benzazepine; 8-Cyano-7-methoxy-1-methy)-2,3,4,5-tetrahydro-1H-3-benzazepine; 8-bromo-1-cyclopropyl-7-methoxy-2,3,4,5-tetrahydro-1H-3-benzazepine; 8-bromo-1-hydroxymethyl-7-methoxy-2,3,4,5-tetrahydro-1H-3-benzazepine; 8-Bromo-1-isopropyl-7-methoxy-2,3,4,5-tetrahydro-1H-3-benzazepine; 8-Bromo-7-hydroxy-1-isopropyl-2,3,4,5-tetrahydro-1H-3-benzazepine; 7-Allyloxy-8-bromo-1-isopropyl-2,3,4,5-tetrahydro-1H-3-benzazepine; 8-Bromo-7-methoxy-1,4-dimethyl-2,3,4,5-tetrahydro-1H-3-benzazepine; 7-Allyloxy-8-bromo-1,4-dim-ethyl-2,3,4,5-tetrahydro-1H-3-benzazepine; 7-(2-Methyl-2H-pyrazol-3-yl)-1-methyl-2,3,4,5-tetrahydro-1H-3-benzazepine; 7-(4-Bromo-2-methyl-2H-pyrazol-3-yl)-1-methyl-2,3,4,5-tetrahydro-1H-3-benzazepine; 7-(3-Chlorophenyl)-1-methyl-2,3,4,5-tetrahydro-1H-3-benzazepine; 7-(2-Chlorophenyl)-1-methyl-2,3,4,5-tetrahydro-1H-3-benzazepine; 8-Chloro-1-hydroxy-2,3,4,5-tetrahydro-1H-3-benzazepine; 8-Bromo-1-methyl-2,3,4,5-tetrahydro-1H-3-benzazepine; 8-Fluoro-1-methyl-2,3,4,5-tetrahydro-1H-3-benzazepine; 7-Fluoro-1-methyl-2,3,4,5-tetrahydro-1H-3-benzazepine; 7,8-Dichloro-1-methyl-2,3,4,5-tetrahydro-1H-3-benzazepine; N-Methyl-8-chloro-1-methyl-2,3,4,5-tetrahydro-1H-3-benzazepine; 1-Methyl-7-trifluoromethoxy-2,3,4,5-tetrahydro-1H-3-benzazepine; 8-Iodo-1-methyl-7-trifluoromethoxy-2,3,4,5-tetrahydro-1H-3-benzazepine; N-Propyl-8-iodo-7-methoxy-1-methyl-2,3,4,5-tetrahydro-1H-3-benzazepine; 1-Ethyl-8-iodo-7-methoxy-2,3,4,5-tetrahydro-1H-3-benzazepine; 7-(3-Methoxyphenyl)-1-methyl-2,3,4,5-tetrahydro-1H-3-benzazepine; difluorophenyl)-1-methyl-2,3,4,5-tetrahydro-1H-3-benzazepine; 7-(2-fluorophenyl)-8-chloro-1-methyl-2,3,4,5-tetrahydro-1H-3-benzazepine; 7-(2-Trifluoromethylphenyl)-1-methyl-2,3,4,5-tetrahydro-1H-3-benzazepine; 7-(3-Trifluoromethylphenyl)-1-methyl-2,3,4,5-tetrahydro-1H-3-benzazepine; 7-(4-Trifluoromethylphenyl)-1-methyl-2,3,4,5-tetrahydro-1H-3-benzazepine; 8-(2-Chlorophenyl)-1-methyl-2,3,4,5-tetrahydro-1H-3-benzazepine; and 8-bromo-1-methoxymethyl-7-methoxy-2,3,4,5-tetrahydro-1H-3-benzazepine; or a pharmaceutically acceptable salt, solvate or hydrate thereof.

In a preferred embodiment, the compounds of Formula (I) are selected from:

N-methyl-8-Bromo-7-methoxy-1-methyl-2,3,4,5-tetrahydro-1H-3-benzazepine; N-methyl-8-Chloro-7-methoxy-1-methyl-2,3,4,5-tetrahydro-1H-3-benzazepine; N-methyl-8-Iodo-7-methoxy-1-methyl-2,3,4,5-tetrahydro-1H-3-benzazepine; N-Methyl-8-bromo-7-methoxy-1-methyl-2,3,4,5-tetrahydro-1H-3-benzazepine; N-methyl-8-Bromo-1-ethyl-7-methoxy-2,3,4,5-tetrahydro-1H-3-benzazepine; N-methyl-8-Chloro-1-ethyl-7-methoxy-2,3,4,5-tetrahydro-1H-3-benzazepine; N-methyl-8-Iodo-1-ethyl-7-methoxy-2,3,4,5-tetrahydro-1H-3-benzazepine; N-methyl-7-Methoxy-1-methyl-8-trifluoromethyl-2,3,4,5-tetrahydro-1H-3-benzazepine; and N-methyl-7-Methoxy-1-methyl-8-pentafluoroethyl-2,3,4,5-tetrahydro-1H-3-benzazepine; or a pharmaceutically acceptable salt, solvate or hydrate thereof.

In a preferred embodiment, the compounds of Formula (I) are selected from:

N-methyl-8-Chloro-1-methyl-2,3,4,5-tetrahydro-1H-3-benzazepine; N-methyl-8-Bromo-1-methyl-2,3,4,5-tetrahydro-1H-3-benzazepine; N-methyl-8-Iodo-1-methyl-2,3,4,5-tetrahydro-1H-3-benzazepine; N-methyl-8-Trifluoromethyl-1-methyl-2,3,4,5-tetrahydro-1H-3-benzazepine; N-methyl-8-Trifluoromethyl-1-ethyl-2,3,4,5-tetrahydro-1H-3-benzazepine; N-methyl-8-Chloro-1-ethyl-2,3,4,5-tetrahydro-1H-3-benzazepine; N-methyl-8-Bromo-1-ethyl-2,3,4,5-tetrahydro-1H-3-benzazepine; N-methyl-8-Iodo-1-ethyl-2,3,4,5-tetrahydro-1H-3-benzazepine; N-methyl-7,8-Dichloro-1-methyl-2,3,4,5-tetrahydro-1H-3-benzazepine; N-methyl-7,8-Dichloro-1-ethyl-2,3,4,5-tetrahydro-1H-3-benzazepine; N-methyl-8-Chloro-7-fluoro-1-methyl-2,3,4,5-tetrahydro-1H-3-benzazepine; and N-methyl-8-Chloro-7-fluoro-1-ethyl-2,3,4,5-tetrahydro-1H-3-benzazepine; or a pharmaceutically acceptable salt, solvate or hydrate thereof.

In a preferred embodiment, the compounds of Formula (I) are selected from:

8-Bromo-7-methoxy-1-methyl-2,3,4,5-tetrahydro-1H-3-benzazepine; 8-Chloro-7-methoxy-1-methyl-2,3,4,5-tetrahydro-1H-3-benzazepine; 8-Iodo-7-methoxy-1-methyl-2,3,4,5-tetrahydro-1H-3-benzazepine; N-Methyl-8-bromo-7-methoxy-1-methyl-2,3,4,5-tetrahydro-1H-3-benzazepine; 8-Bromo-1-ethyl-7-methoxy-2,3,4,5-tetrahydro-1H-3-benzazepine; 8-Chloro-1-ethyl-7-methoxy-2,3,4,5-tetrahydro-1H-3-benzazepine; 8-Iodo-1-ethyl-7-methoxy-2,3,4,5-tetrahydro-1H-3-benzazepine; 7-Methoxy-1-methyl-8-trifluoromethyl-2,3,4,5-tetrahydro-1H-3-benzazepine; and 7-Methoxy-1-methyl-8-pentafluoroethyl-2,3,4,5-tetrahydro-1H-3-benzazepine; or a pharmaceutically acceptable salt, solvate or hydrate thereof.

In a preferred embodiment, the compounds of Formula (I) are selected from:

8-Chloro-1-methyl-2,3,4,5-tetrahydro-1H-3-benzazepine; 8-Bromo-1-methyl-2,3,4,5-tetrahydro-1H-3-benzazepine; 8-Iodo-1-methyl-2,3,4,5-tetrahydro-1H-3-benzazepine; 8-Trifluoromethyl-1-methyl-2,3,4,5-tetrahydro-1H-3-benzazepine; 8-Trifluoromethyl-1-ethyl-2,3,4,5-tetrahydro-1H-3-benzazepine; 8-Chloro-1-ethyl-2,3,4,5-tetrahydro-1H-3-benzazepine; 8-Bromo-1-ethyl-2,3,4,5-tetrahydro-1H-3-benzazepine; 8-Iodo-1-ethyl-2,3,4,5-tetrahydro-1H-3-benzazepine; 7,8-Dichloro-1-methyl-2,3,4,5-tetrahydro-1H-3-benzazepine; 7,8-Dichloro-1-ethyl-2,3,4,5-tetrahydro-1H-3-benzazepine; 8-Chloro-7-fluoro-1-methyl-2,3,4,5-tetrahydro-1H-3-benzazepine; and 8-Chloro-7-fluoro-1-ethyl-2,3,4,5-tetrahydro-1H-3-benzazepine; or a pharmaceutically acceptable salt, solvate or hydrate thereof.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In some embodiments, compounds of Formula (I) are R enantiomers. In some embodiments, compounds of Formula (I) are S enantiomers. In some embodiments, compounds of Formula (I) are varying mixtures of enantiomers.

According to a further aspect of the invention, compounds of Formula (I) are provided for use in therapy. The compounds of Formula (I) can be used in the prophylaxis or treatment of disorders associated with 5-$HT_{2C}$ receptor function.

The compounds of Formula (I) can be used in the prophylaxis or treatment of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of Formula (I) in the manufacture of a medicament for the prophylaxis or treatment of the disorders disclosed herein. In a preferred embodiment, there is provided a use of a compound of Formula (I) in the manufacture of a medicament for the prophylaxis or treatment of obesity.

The compounds according to the invention may optionally exist as pharmaceutically acceptable salts including pharmaceutically acceptable acid addition salts prepared from pharmaceutically acceptable non-toxic acids including inorganic and organic acids. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as the pharmaceutically acceptable salts listed in Journal of Pharmaceutical Science, 66, 2 (1977) and incorporated herein by reference.

The acid addition salts can be obtained as the direct products of compound synthesis. In the alternative, the free base can be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compositions of the invention may conveniently be administered in unit dosage form and can be prepared by any of the methods well known in the pharmaceutical art, for example, as described in *Remington's Pharmaceutical Sciences* (Mack Pub. Co., Easton, Pa., 1980).

The compounds of the invention can be employed as the sole active agent in a pharmaceutical or can be used in combination with other active ingredients which could facilitate the therapeutic effect of the compound.

Compounds of the present invention or a solvate or physiologically functional derivative thereof can be used as active ingredients in pharmaceutical compositions, specifically as 5$HT_{2C}$ receptor agonists. By the term "active ingredient" is defined in the context of a "pharmaceutical composition" and shall mean a component of a pharmaceutical composition that provides the primary pharmaceutical benefit, as opposed to an "inactive ingredient" which would generally be recognized as providing no pharmaceutical benefit. The term "pharmaceutical composition" shall mean a composition comprising at least one active ingredient and at least one ingredient that is not an active ingredient (for example and not limitation, a filler, dye, or a mechanism for slow release), whereby the composition is amenable to use for a specified, efficacious outcome in a mammal (for example, and not) imitation, a human).

The data developed herein supports the conclusion that the presently disclosed 5-$HT_{2C}$ receptor agonists are of use for the treatment or prophylaxis of clinical obesity or overweight disorders in mammals, including, but not limited to, human. Compounds of the present invention can be administered by oral, sublingual, parenteral, rectal, topical administration or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

In addition to the neutral forms of compounds of the present invention, by appropriate addition of an ionizable substituent, which does not alter the receptor specificity of the compound, physiologically acceptable salts of the compounds may also be formed and used as therapeutic agents. Different amounts of the compounds of the to present invention will be required to achieve the desired biological effect. The amount will depend on factors such as the specific compound, the use for which it is intended, the means of administration, and the condition of the treated individual all of these dosing parameters are within the level of one of ordinary skill in the medicinal arts. A typical dose can be expected to fall in the range of 0.001 to 200 mg per kilogram of body weight of the mammal. Unit doses may contain from 1 to 200 mg of the compounds of the present invention and can be administered one or more times a day, individually or in multiples.

Pharmaceutical compositions, including, but not limited to, pharmaceutical compositions, comprising at least one compound of the present invention and/or an acceptable salt or solvate thereof (e.g., a pharmaceutically acceptable salt or solvate) as an active ingredient combined with at least one carrier or excipient (e.g., pharmaceutical carrier or excipient) can be used in the treatment of clinical conditions for which a $5HT_{2C}$ receptor agonist is indicated. At least one compound of the present invention can be combined with the carrier in either solid or liquid form in a unit dose formulation. The pharmaceutical carrier must be compatible with the other ingredients in the composition and must be tolerated by the individual recipient. Other physiologically active ingredients can be incorporated into the pharmaceutical composition of the invention if desired, and if such ingredients are compatible with the other ingredients in the composition. Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that when the $5HT_{2C}$ receptor agonists are utilized as active ingredients in a pharmaceutical composition, these are not intended for use only in humans, but in other non-human mammals as well. Indeed, recent advances in the area of animal health-care mandate that consideration be given for the use of $5HT_{2C}$ receptor agonists for the treatment of obesity in domestic animals (e.g., cats and dogs), and $5HT_{2C}$ receptor agonists in other domestic animals where no disease or disorder is evident (e.g., food-oriented animals such as cows, chickens, fish, etc.). Those of ordinary skill in the art are readily credited with understanding the utility of such compounds in such settings.

The compounds of the present invention can be readily prepared according to a variety of synthetic manipulations, all of which would be familiar to one skilled in the art. A representative general synthesis is set forth below in Scheme I:

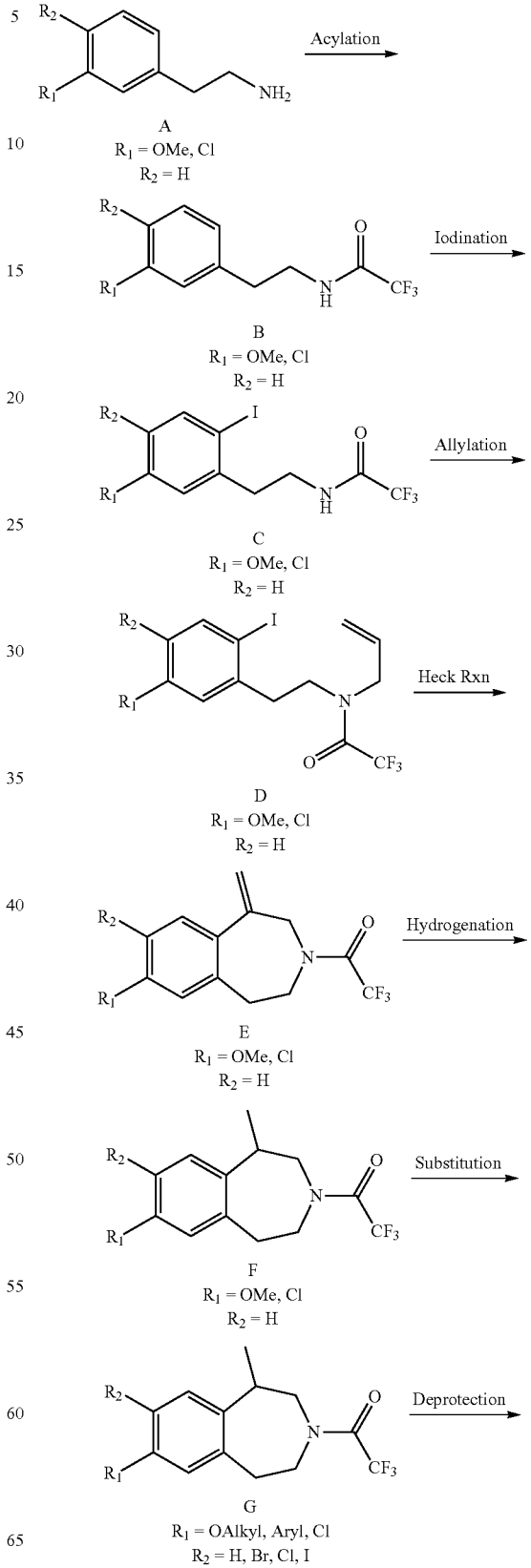

Scheme I
GENERAL REACTION SCHEME

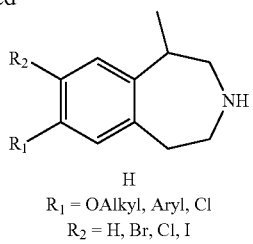

R₁ = OAlkyl, Aryl, Cl
R₂ = H, Br, Cl, I

Those of skill in the art will appreciate that a wide variety of compounds of the invention can be prepared according to Scheme I. For example, by starting with an appropriately substituted 2-phenyl ethylamino compound A having any of a wide variety of substituents $R_1$ and $R_2$, the corresponding 7- and/or 8-substituted 1-methyl-2,3,4,5-tetrahydro-1H-3-benzazepine (compound H) can be prepared. N-alkylation can be accomplished by, for example, treatment with excess paraformaldehyde (for methylation) or a higher order aldehyde, followed by reduction with $NaBH_3CN$ according to the general procedure of synthetic examples 9 and 10, infra. In addition, by starting with an appropriately substituted 1-alkyl-2-phenyl ethylamino compound A having any of a wide variety of substituents $R_1$ and $R_2$, the corresponding 7- and/or 8-substituted 2,5-dialkyl-2,3,4,5-tetrahydro-1H-3-benzazepine compound can be prepared.

In the synthesis of many compounds of the invention, protecting groups can be required to protect various functionality or functionalities during the synthesis. Representative protecting groups suitable for a wide variety of synthetic transformations are disclosed in Greene and Wuts, *Protective Groups in Organic Synthesis*, 2d ed, John Wiley & Sons, New York, 1991, the disclosure of which is incorporated herein by reference in its entirety.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Synthetic Examples

Example 1

(R,S)8-Bromo-7-methoxy-1-methyl-2,3,4,5-tetrahydra-1H-3-benzazepine

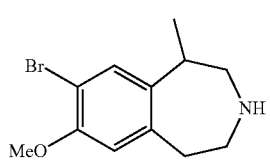

N-Trifluoroacetyl-3-methoxyphenethylamine

A solution of 3-methoxyphenethylamine (10.0 g, 64.0 mmol) in dichloromethane (150 mL), was cooled to 0 C, and treated with pyridine (6.5 mL, 83.5 mmol) followed, by the dropwise addition of trifluoracetic anhydride (17.9 g, 83.5 mmol) and the resulting mixture stirred for 3 hours while warming to 20 C. The product mixture was diluted with EtOAc (500 mL), washed sequentially with 10% aqueous HCl (100 mL), water (100 mL), brine (100 mL), dried with $Na_2SO_4$ and concentrated to give 15.8 g of a yellow oil. 1H NMR (400 MHz, $CDCl_3$) d 7.26 (dd, J=8, 8 Hz, 1H), 6.81 (d, J=8 Hz, 1H), 6.77 (d, J=8 Hz, 1H), 6.72 (s, 1H), 6.30 (bs, 1H), 3.80 (s, 3H), 3.62 (dd, J=7, 7 Hz, 2H), 2.86 (dd, J=7, 7 Hz, 2H). MS calculated for $C_{11}H_{12}F_3NO_2$+H: 248, observed: 248.

N-Trifluoroacetyl-2-iodo-5-methoxyphenethylamine

A solution of N-trifluoroacetyl-3-methoxyphenethylamine (15.8 g, 64 mmol) in methanol (325 mL) was cooled to −78 C, and treated with $CaCO_3$ (14.7 g, 145 mmol), followed by a solution of ICl (29 g, 181 mmol) in methanol (40 mL). The reaction was allowed to warm to 20 C while stirring overnight and then filtered, concentrated, dissolved in EtOAc (200 mL), washed twice with 5% aqueous sodium bisulfite (100 mL), once with brine (100 mL), dried with $Na_2SO_4$ and concentrated to give 23.8 g of a white solid powder. 1H NMR (400 MHz, $CDCl_3$) d 7.68 (d, J=9 Hz, 1H), 6.76 (s, 1H), 6.57 (d, J=9 Hz, 1H), 6.42 (bs, 1H), 3.77 (s, 3H), 3.61 (dd, J=7, 7 Hz, 2H), 2.99 (dd, J=7, 7 Hz, 2H). MS calculated for $C_{11}H_{11}F_3INO_2$+H: 374, observed: 374.

N-Allyl, N-trifluoroacetyl-2-iodo-5-methoxyphenethylamine

A solution of N-trifluoroacetyl-2-iodo-5-methoxyphenethylamine (23.8 g, 63.8 mmol) in toluene (425 mL) was sequentially treated with $K_2CO_3$ (12.4 g, 89.8 mmol), KOH (11.6 g, 207 mmol), n-$Bu_4NBr$ (2.2 g, 6.9 mmol) and allyl bromide (10.7 g, 89.8 mmol). The mixture was stirred at 80 C for 15 hours, cooled to 20 C, acidified with 10% aqueous HCl, separated and the aqueous phase extracted with ether (500 mL). The combined organic phases were washed with brine (200 mL), dried with $Na_2SO_4$ and concentrated to give 20.5 g of a brown oil. 1H NMR (400 MHz, $CDCl_3$), mixture of rotamers d 7.67 (m, 1H), 6.80 (m, 1H), 6.57 (m, 1H), 5.9-5.6 (bm, 1H), 5.27 (m, 2H), 4.11 (d, J=6 Hz, 0.5H), 3.85 (d, J=6 Hz, 0.5H), 3.77 (m, 3H), 3.55 (m, 2H), 3.00 (m, 2H). MS calculated for $C_{14}H_{15}F_3INO_2$+H: 414, observed: 414.

N-Trifluoroacetyl-7-methoxy-1-methylene-2,3,4,5-tetrahydro-1H-3-benzazepine

A solution of N-allyl, N-trifluoroacetyl-2-iodo-5-methoxyphenethylamine (20.5 g, 50 mmol) in dimethylformamide (250 mL) is treated with KOAc (14.6 g, 149 mmol), n-$Bu_4NBr$ (16.0 g, 50 mmol), $PPh_3$ (1.3 g, 5.0 mmol), $Pd(OAc)_2$ (0.56 g, 2.5 mmol) and stirred overnight at 90 C. The product mixture was cooled to 20 C, filtered, diluted with water (500 mL) and extracted with ether (3×500 mL). The combined organic phases were washed with water (100 mL), brine (100 mL), dried with $Na_2SO_4$ and concentrated. Flash chromatography (10% EtOAc in hexane, silica) resulted in 6.6 g of a yellow oil.

1H NMR (400 MHz, $CDCl_3$) d 7.26 (d, J=8 Hz, 1H), 6.77 (d, J=8 Hz, 1H), 6.66 (s, 1H), 5.34-5.19 (m, 2H), 4.40 (m, 2H), 3.83 (m, 2H), 3.80 (s, 3H), 3.00 (m, 2H). MS calculated for $C_{14}H_{14}F_3NO_2$+H: 285, observed: 285.

N-Trifluoroacetyl-7-methoxy-1-methyl-2,3,4,5-tetrahydro-1H-3-benzazepine

A solution of N-trifluoroacetyl-7-methoxy-1-methylene-2,3,4,5-trihydro-1H-3-benzazepine (6.6 g, 23.2 mmol) in ethanol (100 mL), was treated with 10% Pd/C (0.75 g, 2.3 mmol) and stirred overnight under an atmosphere of hydrogen. The product mixture was filtered through a pad of celite and silica and the solvent removed to give 6.27 g of a white solid. 1H NMR (400 MHz, CDCl$_3$, mixture of rotamers) d 7.10 (m, 1H), 6.74 (m, 1H), 6.68 (m, 1H), 4.1-3.8 (bm, 2H), 3.8 (s, 3H), 3.5 (m, 1.5H), 3.4 (m, 0.5H), 3.2-2.9 (bm, 4H), 1.32 (m, 3H). MS calculated for $C_{14}H_{16}F_3NO_2$+H: 288, observed: 288.

N-Trifluoroacetyl-8-bromo-7-methoxy-1-methyl-2,3,4,5-tetrahydro-1H-3-benzazepine A solution of N-trifluoroacetyl-7-methoxy-1-methyl-2,3,4,5-tetrahydro-1H-3-benzazepine (1.25 g, 4.35 mmol) in acetonitrile (40 mL) was treated with N-bromosuccinimide (0.852 g, 4.79 mmol) and stirred overnight at 20 C. The product mixture was diluted with EtOAc (200 mL), washed with saturated aqueous sodium bisulfite (100 mL) and brine (100 mL), dried with Na$_2$SO$_4$ and concentrated. Flash chromatography (15% EtOAc in hexane, silica) resulted in 1.55 g of a clear oil. 1H NMR (400 MHz, CDCl$_3$, mixture of rotamers) d 7.34 (s, 1H), 6.65 (m, 1H), 3.87 (s, 3H), 3.81 (m, 1H), 3.55 (m, 1.3H), 3.37 (m, 0.7H), 3.2-2.9 (bm, 4H), 1.30 (m, 3H). MS calculated for $C_{14}H_{15}BrF_3NO_2$+H: 366, observed: 366.

8-Bromo-7-methoxy-1-methyl-2,3,4,5-tetrahydro-1H-3-benzazepine

A solution of N-trifluoroacetyl-8-bromo-7-methoxy-1-methyl-2,3,4,5-tetrahydro-1H-3-benzazepine (0.95 g, 2.59 mmol) in methanol (20 mL) was treated with 15% aqueous NaOH (25 mL), and stirred overnight at 20 C. The product mixture was diluted with water (100 mL), extracted twice with EtOAc (100 mL), the combined organic phases were washed with brine (100 mL), dried with Na$_2$SO$_4$ and concentrated to give 0.687 g of a clear oil. 1H NMR (400 MHz, CDCl$_3$) d 7.92 (s, 1H), 6.34 (s, 1H), 3.87 (s, 3H), 3.1-2.9 (m, 6H), 2.75 (m, 1H), 2.60 (bs, 1H), 1.31 (d, J=7 Hz, 3H). MS calculated for $C_{12}H_{16}BrNO$+H: 270, observed: 270.

Example 2

(R,S)8-Chloro-7-methoxy-1-methyl-2,3,4,5-tetrahydro-1H-3-benzazepine

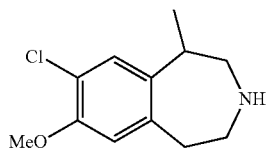

N-Trifluoroacetyl-8-chloro-7-methoxy-1-methyl-2,3,4,5-tetrahydro-1H-3-benzazepine A solution of N-trifluoroacetyl-7-methoxy-1-methyl-2,3,4,5-tetrahydro-1H-3-benzazepine (0.900 g, 2.67 mmol) in acetonitrile (30 mL) was treated with N-chlorosuccinimide (0.357 g, 2.67 mmol) and stirred overnight at 70 C. The product mixture was diluted with water (100 mL), extracted twice with EtOAc (100 mL), the combined organic phases washed with brine (100 mL), dried with Na$_2$SO$_4$ and concentrated. Flash chromatography (20% EtOAc in hexane, silica) resulted in 0.399 g of a clear oil. 1H NMR (400 MHz, CDCl$_3$, mixture of rotamers) d 7.17 (s, 1H), 6.68 (m, 1H), 3.88 (s, 3H), 3.78 (m, 1H), 3.6-3.3 (m, 2H), 3.2-2.9 (m, 4H), 1.34 (m, 3H). MS calculated for $C_{14}H_{15}ClF_3NO_2$+H: 322, observed: 322.

8-Chloro-7-methoxy-1-methyl-2,3,4,5-tetrahydro-1H-3-benzazepine

A solution of N-trifluoroacetyl-8-chloro7-methoxy-1-methyl-2,3,4,5-tetrahydro-1H-3-benzazepine (0.399 g, 1.24 mmol) in methanol (20 mL) was treated with 15% aqueous NaOH (20 mL), and stirred overnight at 20 C. The product mixture was diluted with water (100 mL), extracted twice with EtOAc (100 mL), the combined organic phases were washed with brine (100 mL), dried with Na$_2$SO$_4$ and concentrated to give 0.306 g of a yellow solid. 1H NMR (400 MHz, CDCl$_3$) d 7.05 (s, 1H), 6.59 (s, 1H), 3.80 (s, 3H), 3.0-2.8 (m, 6H), 2.62 (m, 1H), 2.16 (bs, 1H), 1.24 (d, J=7 Hz, 3H). MS calculated for $C_{12}H_{16}ClNO$+H: 226, observed: 226.

Example 3

(R,S)8-Iodo-7-methoxy-1-methyl-2,3,4,5-tetrahydro-1H-3-benzazepine

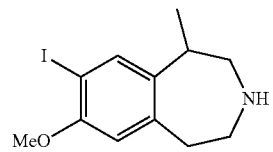

N-Trifluoroacetyl-8-iodo-7-methoxy-1-methyl-2,3,4,5-tetrahydro-1H-3-benzazepine A solution of N-trifluoroacetyl-7-methoxy-1-methyl-2,3,4,5-tetrahydro-1H-3-benzazepine (1.50 g, 5.22 mmol) in methanol (70 mL) was treated with CaCO$_3$ (1.06 g, 10.44 mmol) followed by a solution of ICl (1.70 g, 10.44 mmol) in methanol (10 mL), and stirred overnight at 20 C. The product mixture was filtered, concentrated, dissolved in EtOAc (200 mL), extracted twice with 5% aqueous sodium bisulfite (100 mL), once with brine (100 mL), dried with Na$_2$SO$_4$ and concentrated. Flash chromatography (15% EtOAc in hexane, silica) resulted in 1.54 g of a white solid. 1H NMR (400 MHz, CDCl$_3$, mixture of rotamers) d 7.55 (m, 1H), 6.57 (m, 1H), 3.86 (s, 3H), 3.80 (m, 1H), 3.60-3.30 (m, 2H), 3.20-2.80 (m, 4H), 1.30 (m, 3H). MS calculated for $C_{14}H_{15}F_3INO_2$+H: 414, observed: 414.

8-Iodo-7-methoxy-1-methyl-2,3,4,5-tetrahydro-1H-3-benzazepine

A solution of N-trifluoroacetyl-8-iodo7-methoxy-1-methyl-2,3,4,5-tetrahydro-1H-3-benzazepine (0.600 g, 1.45 mmol) in methanol (20 mL) was treated with 15% aqueous NaOH (20 mL), and stirred for 3 hours at 50 C. The product mixture was diluted with water (100 mL), extracted twice with EtOAc (100 mL), the combined organic phases were washed with brine (100 mL), dried with Na$_2$SO$_4$ and concentrated to give 0.425 g of a yellow solid. 1H NMR (400 MHz, CDCl$_3$) d 7.52 (s, 1H), 6.57 (s, 1H), 3.86 (s, 3H), 3.12-3.06

(m, 4H), 2.95 (m, 2H), 2.75 (m, 1H), 2.43 (bs, 1H), 1.33 (d, J=8 Hz, 3H). MS calculated for $C_{12}H_{16}INO+H$: 318, observed: 318.

Example 4

(R,S)8-Bromo-7-hydroxy-1-methyl-2,3,4,5-tetrahydro-1H-3-benzazepine

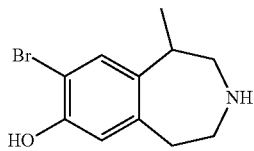

N-Trifluoroacetyl-8-bromo-7-hydroxy-1-methyl-2,3,4,5-tetrahydro-1H-3-benzazepine A solution of N-trifluoroacetyl-8-bromo-7-methoxy-1-methyl-2,3,4,5-tetrahydro-1H-3-benzazepine (1.50 g, 4.10 mmol) in dichloromethane (80 mL) was treated dropwise with BBr$_3$ (9.4 mL of a 1.0M solution in CH$_2$Cl$_2$, 9.4 mmol), and the mixture stirred overnight while warming to 20 C. The excess BBr$_3$ was quenched with the dropwise addition of water, the mixture diluted with ether (200 mL), washed with Na$_2$CO$_3$ (100 mL) and brine (100 mL), dried with Na$_2$SO$_4$ and concentrated. Flash chromatography (15% EtOAc in hexane, silica) resulted in 1.25 g of a white solid foam.

1H NMR (400 MHz, CDCl$_3$, mixture of rotamers) d 7.25 (s, 1H), 6.79 (m, 1H), 3.79 (m, 1H), 3.7-3.3 (m, 2H), 3.2-2.8 (m, 4H), 1.32 (m, 3H).

8-Bromo-7-hydroxy-1-methyl-2,3,4,5-tetrahydro-1H-3-benzazepine

A solution of N-trifluoroacetyl-8-bromo-7-hydroxy-1-methyl-2,3,4,5-tetrahydro-1H-3-benzazepine (0.655 g, 1.89 mmol) in methanol (20 mL) was treated with 15% aqueous NaOH (20 mL), and stirred overnight at 20 C. The product mixture was diluted with water (100 mL), extracted twice with EtOAc (100 mL), the combined organic phases were washed with brine (100 mL), dried with Na$_2$SO$_4$ and concentrated to give 0.460 g of a clear oil. 1H NMR (400 MHz, DMSO-d$_6$) d 7.11 (s, 1H), 6.65 (s, 1H), 2.90 (m, 1H), 2.73 (m, 5H), 2.55 (m, 1H), 1.19 (d, J=7 Hz, 3H). MS calculated for $C_{11}H_{14}BrNO+H$: 256, observed: 256.

Example 5

(R,S)7-Allyloxy-8-bromo-1-methyl-2,3,4,5-tetrahydro-1H-3-benzazepine

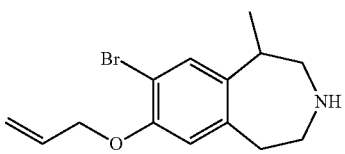 [SMILES: C=CCOc1cc2c(cc1Br)C(C)CNCC2]

N-Trifluoroacetyl-7-allyloxy-8-bromo-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.150 g, 0.426 mmol) in dichloromethane (5 mL) was treated with allyl bromide (0.155 g, 1.28 mmol) and DBU (0.195 g, 1.28 mmol) and then stirred 2 hours at 20 C. The product mixture was diluted with EtOAc (50 mL), washed with 5% aqueous HCl (20 mL), brine (20 mL), dried with Na$_2$SO$_4$ and concentrated. Flash chromatography (15% EtOAc in hexane, silica) resulted in 0.149 g of a clear oil. 1H NMR (400 MHz, CDCl$_3$, mixture of rotamers) d 7.34 (s, 1H), 6.65 (m, 1H), 6.04 (m, 1H), 5.47 (d, J=17 Hz, 1H), 5.30 (d, J=9 Hz, 1H), 4.59 (s, 2H), 3.80 (m, 1H), 3.6-3.3 (m, 3H), 3.2-2.8 (m, 4H), 1.31 (m, 3H). MS calculated for $C_{16}H_{17}BrF_3NO_2+H$: 392, observed: 392.

7-Allyloxy-8-bromo-1-methyl-2,3,4,5-tetrahydro-1H-3-benzazepine

A solution of N-trifluoroacetyl-7-allyloxy-8-bromo-1-methyl-2,3,4,5-tetrahydro-1H-3-benzazepine (1.18 g, 3.00 mmol) in methanol (35 mL) was treated with 15% aqueous NaOH (35 mL), and stirred overnight at 20 C. The product mixture was diluted with water (200 mL), extracted twice with EtOAc (200 mL), the combined organic phases were washed with brine (100 mL), dried with Na$_2$SO$_4$ and concentrated to give 0.880 g of a clear oil. 1H NMR (400 MHz, CDCl$_3$) d 7.29 (s, 1H), 6.63 (s, 1H), 6.04 (m, 1H), 5.47 (d, J=17 Hz, 1H), 5.29 (d, J=11 Hz, 1H), 4.58 (s, 2H), 3.01 (m, 3H), 2.89 (m, 3H), 2.75 (m, 1H), 1.31 (d, J=7 Hz, 3H). MS calculated for $C_{14}H_{18}BrNO+H$: 296, observed: 296.

Example 6

(R,S)7-Benzyloxy-8-bromo-1-methyl-2,3,4,5-tetrahydro-1H-3-benzazepine

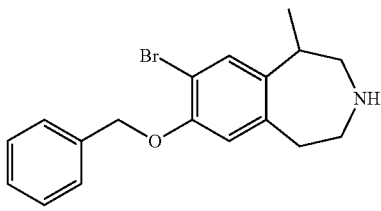 [SMILES: CC1CNCCc2cc(OCc3ccccc3)c(Br)cc21]

N-Trifluoroacetyl-7-benzyloxy-8-bromo-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.075 g, 0.213 mmol) in dichloromethane (5 mL) was treated with benzyl bromide (0.072 g, 0.64 mmol), DBU (0.100 g, 0.64 mmol), and stirred 2 hours at 20 C. The product mixture was diluted with EtOAc (50 mL), washed with 5% aqueous HCl (20 mL), brine (20 mL), dried with Na$_2$SO$_4$ and concentrated. Flash chromatography (15% EtOAc in hexane, silica) resulted in 0.081 g of a clear oil. MS calculated for $C_{20}H_{19}BrF_3NO_2+H$: 442, observed: 442.

7-Benzyloxy-8-bromo-1-methyl-2,3,4,5-tetrahydro-1H-3-benzazepine

A solution of N-trifluoroacetyl-7-benzyloxy-8-bromo-1-methyl-2,3,4,5-tetrahydro-1H-3-benzazepine (0.81 g, 1.83 mmol) in methanol (20 mL) was treated with 15% aqueous NaOH (20 mL), and stirred overnight at 20 C. The product mixture was diluted with water (200 mL), extracted twice with EtOAc (200 mL), the combined organic phases were washed with brine (100 mL), dried with $Na_2SO_4$ and concentrated to give 0.412 g of a clear oil. 1H NMR (400 MHz, $CDCl_3$) d 7.38 (d, J=8 Hz, 2H), 7.30 (dd, J=7, 8 Hz, 2H), 7.23 (m, 2H), 6.61 (s, 1H), 5.03 (s, 2H), 2.94 (m, 3H), 2.81 (m, 3H), 2.62 (m, 1H), 2.30 (bs, 1H), 1.24 (d, J=7 Hz, 3H). MS calculated for $C_{18}H_{20}BrNO+H$: 346, observed: 346.

Example 7

(R,S)8-Bromo-7-ethoxy-1-methyl-2,3,4,5-tetrahydro-1H-3-benzazepine

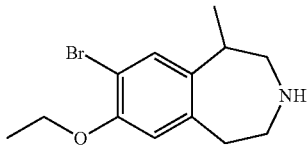 [SMILES: CCOc1cc2c(cc1Br)C(C)CNCC2]

N-Trifluoroacetyl-8-bromo-7-ethoxy-1-methyl-2,3,4,5-tetrahydro-1H-3-benzazepine

A solution of N-trifluoroacetyl-8-bromo-7-hydroxy-1-methyl-2,3,4,5-tetrahydro-1H-3-benzazepine (0.015 g, 0.043 mmol) in dichloromethane (1 mL) was treated with ethyl iodide (0.016 g, 0.102 mmol), DBU (0.016 g, 0.102 mmol) and stirred 2 hours at 20 C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 0.010 g of a clear oil.

8-Bromo-7-ethoxy-1-methyl-2,3,4,5-tetrahydro-1H-3-benzazepine

A solution of N-trifluoroacetyl-8-bromo-7-ethoxy-1-methyl-2,3,4,5-tetrahydro-1H-3-benzazepine (0.010 g, 0.026 mmol) in methanol (1 mL) was treated with 15% aqueous NaOH (1 mL), and stirred overnight at 20 C. The product mixture was diluted with water (3 mL), extracted twice with EtOAc (5 mL), the combined organic phases were washed with brine (3 mL), dried with $Na_2SO_4$ and concentrated to give 0.007 g of a clear oil. 1H NMR (400 MHz, $CDCl_3$) d 7.29 (s, 1H), 6.63 (s, 1H), 4.07 (q, J=6 Hz, 2H), 3.03 (m, 3H), 2.91 (m, 3H), 2.73 (m, 1H), 2.26 (bs, 1H), 1.46 (t, J=6 Hz, 3H), 1.32 (d, J=7 Hz, 3H). MS calculated for $C_{15}H_{17}BrF_3NO_2+H$: 380, observed: 380.

Example 8

(R,S)8-Bromo-7-isopropoxy-1-methyl-2,3,4,5-tetrahydro-1H-3-benzazepine

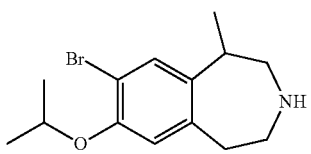 [SMILES: CC(C)Oc1cc2c(cc1Br)C(C)CNCC2]

N-Trifluoroacetyl-8-bromo-7-isopropoxy-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.035 g, 0.099 mmol) in dichloromethane (1 mL) was treated with isopropyl bromide (0.037 g, 0.297 mmol), DBU (0.048 g, 0.205 mmol) and stirred 2 hours at 20 C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 0.014 g of a clear oil. MS calculated for $C_{16}H_{19}BrF_3NO_2+H$: 394, observed: 394.

8-Bromo-7-isopropoxy-1-methyl-2,3,4,5-tetrahydro-1H-3-benzazepine

A solution of N-trifluoroacetyl-8-bromo-7-isopropoxy-1-methyl-2,3,4,5-tetrahydro-1H-3-benzazepine (0.014 g, 0.035 mmol) in methanol (1 mL) was treated with 15% aqueous NaOH (1 mL), and stirred overnight at 20 C. The product mixture was diluted with water (3 mL), extracted twice with EtOAc (5 mL), the combined organic phases were washed with brine (3 mL), dried with $Na_2SO_4$ and concentrated to give 0.008 g of a clear oil. 1H NMR (400 MHz, $CDCl_3$) d 7.24 (s, 1H), 6.64 (s, 1H), 4.48 (m, 1H), 2.98 (m, 3H), 2.87 (m, 3H), 1.36 (m, 6H), 1.30 (d, J=7 Hz, 3H). MS calculated for $C_{14}H_{20}BrNO+H$: 298, observed: 298.

Example 9

(R,S)N-Methyl-8-bromo-7-methoxy-1-methyl-2,3,4,5-tetrahydro-1H-3-benzazepine

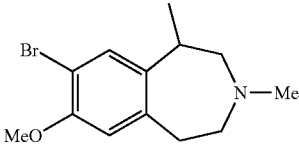 [SMILES: COc1cc2c(cc1Br)C(C)CN(C)CC2]

A solution of 8-Bromo-7-methoxy-1-methyl-2,3,4,5-tetrahydro-1H-3-benzazepine (6 mg, 0.022 mmol) in methanol (1 mL) was treated with excess paraformaldehyde, 1.0 M HCl in ether (0.004 mL, 0.004 mmol), $NaBH_3CN$ (1.0 mg, 0.013 mmol), and stirred overnight at 20 C. The product mixture was diluted with 5% aqueous NaOH (5 mL), extracted 3 times with $CH_2Cl_2$ (5 mL each), the combined organic phases were dried with $Na_2SO_4$ and concentrated. Flash chromatography (10% MeOH in $CH_2Cl_2$, silica) resulted in 5 mg of a clear oil. 1H NMR (400 MHz, $CDCl_3$) d 7.31 (s, 1H), 6.66 (s, 1H), 3.87 (s, 3H), 3.26 (bm, 2H), 3.01 (bs, 1H), 2.85 (m, 2H), 2.45 (s, 3H), 2.45-2.25 (m, 2H), 1.36 (d, J=7 Hz, 3H). MS calculated for $C_{13}H_{18}BrNO+H$: 284, observed: 284.

Example 10

(R,S)N-Propyl-8-bromo-7-methoxy-1-methyl-2,3,4,5-tetrahydro-1H-3-benzazepine

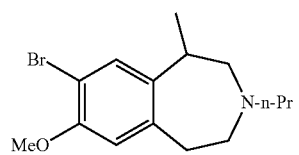

A solution of 8-Bromo-7-methoxy-1-methyl-1,2,4,5-tetrahydro-3H-3-benzazepine (6 mg, 0.022 mmol) in methanol (1 mL) was treated with propionaldehyde (5.0 mg, 0.067 mmol), 1.0 M HCl in ether (0.004 mL, 0.004 mmol), NaBH$_3$CN (1.0 mg, 0.013 mmol), and stirred overnight at 20 C. The product mixture was diluted with 5% aqueous NaOH (5 mL), extracted 3 times with CH$_2$Cl$_2$ (5 mL each), the combined organic phases were dried with Na$_2$SO$_4$ and concentrated. Flash chromatography (10% MeOH in CH$_2$Cl$_2$, silica) resulted in 4 mg of a clear oil. 1H NMR (400 MHz, CD$_3$OD) d 7.33 (s, 1H), 6.87 (s, 1H), 3.84 (s, 3H), 3.25 (m, 2H), 3.11 (m, 2H), 2.97 (m, 1H), 2.78 (bm, 2H), 2.63 (bm, 2H), 1.67 (m, 2H), 1.38 (d, J=7 Hz, 3H), 0.96 (t, J=7 Hz, 3H). MS calculated for C$_{15}$H$_{22}$BrNO+H: 312, observed: 312.

Example 11

(R,S)7-Hydroxy-8-iodo-1-methyl-2,3,4,5-tetrahydro-1H-3-benzazepine

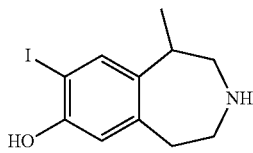

N-Trifluoroacetyl-7-hydroxy-8-iodo-1-methyl-2,3,4,5-tetrahydro-1H-3-benzazepine

A solution of N-trifluoroacetyl-8-iodo-7-methoxy-1-methyl-2,3,4,5-tetrahydro-1H-3-benzazepine (80 mg, 0.19 mmol) in dichloromethane (3 mL) was treated with BBr$_3$ (0.40 mL of a 1.0M solution in CH$_2$Cl$_2$, 0.40 mmol) and stirred overnight at 20 C. The excess BBr$_3$ was quenched with water and the product mixture was diluted with ether (20 mL), washed with Na$_2$CO$_3$ (10 mL) and brine (10 mL), dried with Na$_2$SO$_4$ and concentrated. Flash chromatography (15% EtOAc in hexane, silica) resulted in 74 mg of a white solid. MS calculated for C$_{13}$H$_{13}$F$_3$INO$_2$+H: 400, observed: 400.

7-Hydroxy-8-iodo-1-methyl-2,3,4,5-tetrahydro-1H-3-benzazepine

A solution of N-trifluoroacetyl-7-hydroxy-8-iodo-1-methyl-2,3,4,5-tetrahydro-1H-3-benzazepine (25 mg, 0.063 mmol) in methanol (2 mL) was treated with 15% aqueous NaOH (2 mL), and stirred overnight at 20 C. The product mixture was diluted with water (5 mL), extracted twice with EtOAc (5 mL), the combined organic phases were washed with brine (5 mL), dried with Na$_2$SO$_4$ and concentrated to give 13 mg of a white solid. 1H NMR (400 MHz, CD$_3$OD) d 7.46 (s, 1H), 6.64 (s, 1H), 3.16 (m, 3H), 2.94 (m, 3H), 2.81 (m, 1H), 1.35 (d, J=7 Hz, 3H). MS calculated for C$_{11}$H$_{14}$INO+H: 304, observed: 304.

Example 12

(R,S)7-Allyloxy-8-iodo-1-methyl-2,3,4,5-tetrahydro-1H-3-benzazepine

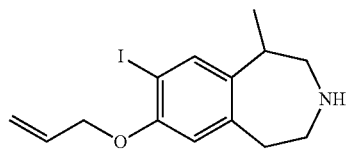 [SMILES: C=CCOc1cc2c(cc1I)C(C)CNCC2]

N-Trifluoroacetyl-7-allyloxy-8-iodo-1-methyl-2,3,4,5-tetrahydro-1H-3-benzazepine A solution of N-trifluoroacetyl-7-hydroxy-8-iodo-1-methyl-2,3,4,5-tetrahydro-1H-3-benzazepine (30 mg, 0.075 mmol) in dichloromethane (2 mL) was treated with allyl bromide (18 mg, 0.15 mmol), DBU (23 mg, 0.15 mmol) and stirred 2 hours at 20 C. to The product mixture was diluted with EtOAc (10 mL), washed with 5% aqueous HCl (5 mL), brine (5 mL), dried with Na$_2$SO$_4$ and concentrated. Flash chromatography (15% EtOAc in hexane, silica) resulted in 23 mg of a clear oil. MS calculated for C$_{16}$H$_{17}$F$_3$INO$_2$+H: 440, observed: 440.

7-Allyloxy-8-iodo-1-methyl-2,3,4,5-tetrahydro-1H-3-benzazepine

A solution of N-trifluoroacetyl-7-allyloxy-8-iodo-1-methyl-2,3,4,5-tetrahydro-1H-3-benzazepine (23 mg, 0.058 mmol) in methanol (2 mL) was treated with 15% aqueous NaOH (2 mL), and stirred overnight at 20 C. The product mixture was diluted with water (5 mL), extracted twice with EtOAc (5 mL), the combined organic phases were washed with brine (5 mL), dried with Na$_2$SO$_4$ and concentrated to give 18 mg of a white solid. MS calculated for C$_{14}$H$_{18}$INO+H: 344, observed: 344.

Example 13

(R,S)3,5-Dimethyl-6,7,8,9-tetrahydro-5H-1-oxa-7-aza-cycloheptaindene

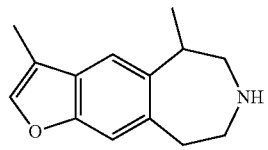 [SMILES: Cc1coc2cc3c(cc12)C(C)CNCC3]

N-trifluoroacetyl-3,5-dimethyl-6,7,8,9-tetrahydro-5H-1-oxa-7-aza-cycloheptaindene A solution of N-trifluoroacetyl-7-allyloxy-8-iodo-1-methyl-2,3,4,5-tetrahydro-1H-3-benzazepine (158 mg, 0.360 mmol) in dimethylformamide (4 mL) was treated with KOAc (106 mg, 1.08 mmol), n-Bu$_4$NBr (116 mg, 0.360 mmol), PPh$_3$ (13 mg, 0.036 mmol), Pd(OAc)$_2$ (4 mg, 0.018 mmol) and stirred overnight at 100 C. The product mixture was filtered, water (10 mL) added and then extracted twice with EtOAc (10 mL). The combined organic phases were washed with brine (10 mL), dried with Na$_2$SO$_4$ and concentrated. Flash chromatography (5% EtOAc in hexane, silica) resulted in 15 mg of a clear oil. MS calculated for C$_{16}$H$_{16}$F$_3$NO$_2$+H: 312, observed: 312.

3,5-Dimethyl-6,7,8,9-tetrahydro-5H-1-oxa-7-aza-cycloheptaindene

A solution of N-trifluoroacetyl-3,5-dimethyl-6,7,8,9-tetrahydro-5H-1-oxa-7-aza-cycloheptaindene (15 mg, 0.048 mmol) in methanol (2 mL) was treated with 15% aqueous NaOH (2 mL), and stirred overnight at 20 C. The product mixture was diluted with water (5 mL), extracted twice with EtOAc (5 mL), the combined organic phases were washed with brine (5 mL), dried with $Na_2SO_4$ and concentrated to give 10 mg of a white solid. 1H NMR (400 MHz, $CDCl_3$) d 7.25 (s, 1H), 7.12 (s, 1H), 7.09 (s, 1H), 3.12 (m, 1H), 2.97 (m, 4H), 2.85 (m, 1H), 2.64 (bm, 1H), 2.15 (s, 3H), 1.34 (d, J=8 Hz, 3H). MS calculated for $C_{14}H_{12}NO+H$: 216, observed: 216.

Example 14

(R,S)7-Allyloxy-8-chloro-1-methyl-2,3,4,5-tetrahydro-1H-3-benzazepine

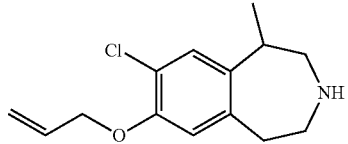 [SMILES: C=CCOc1cc2c(cc1Cl)C(C)CNCC2]

N-Trifluoroacetyl-8-chloro-7-hydroxy-1-methyl-2,3,4,5-tetrahydro-1H-3-benzazepine A solution of N-trifluoroacetyl-8-chloro-7-methoxy-1-methyl-2,3,4,5-tetrahydro-1H-3-benzazepine (48 mg, 0.15 mmol) in dichloromethane (2 mL) was treated with $BBr_3$ (0.30 mL of a 1.0M solution in $CH_2Cl_2$, 0.30 mmol) and stirred overnight at 20 C. The excess $BBr_3$ was quenched with water and the resulting mixture diluted with ether (20 mL), washed with $Na_2CO_3$ (10 mL) and brine (10 mL), dried with $Na_2SO_4$ and concentrated. Flash chromatography (15% EtOAc in hexane, silica) resulted in 24 mg of a white solid. MS calculated for $C_{13}H_{13}ClF_3NO_2+H$: 308, observed: 308.

N-Trifluoroacetyl-7-allyloxy-8-chloro-1-methyl-2,3,4,5-tetrahydro-1H-3-benzazepine A solution of N-trifluoroacetyl-8-chloro-7-hydroxy-1-methyl-2,3,4,5-tetrahydro-1H-3-benzazepine (24 mg, 0.078 mmol) in dichloromethane (2 mL) was treated with allyl bromide (18 mg, 0.15 mmol), DBU (23 mg, 0.15 mmol) and stirred 2 hours at 20 C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 23 mg of a white solid. MS calculated for $C_{16}H_{17}ClF_3NO_2+H$: 348, observed: 348.

7-Allyloxy-8-chloro-1-methyl-2,3,4,5-tetrahydro-1H-3-benzazepine

A solution of N-trifluoroacetyl-7-allyloxy-8-chloro-1-methyl-2,3,4,5-tetrahydro-1H-3-benzazepine (23 mg, 0.066 mmol) in methanol (2 mL) was treated with 15% aqueous NaOH (2 mL), and stirred overnight at 20 C. The product mixture was diluted with water (5 mL), extracted twice with EtOAc (5 mL), the combined organic phases were washed with brine (5 mL), dried with $Na_2SO_4$ and concentrated to give 19 mg of a white solid. 1H NMR (400 MHz, $CD_3OD$) d 7.12 (s, 1H), 6.81 (s, 1H), 6.03 (m, 1H), 5.43 (d, J=17 Hz, 1H), 5.24 (d, J=10 Hz, 1H), 4.57 (d, J=5 Hz, 2H), 3.1-2.9 (m, 5H), 2.81 (m, 1H), 2.63 (m, 1H), 1.30 (d, J=7 Hz, 3H).

Example 15

(R,S)7-Methoxy-1-methyl-8-(2-thienyl)-2,3,4,5-tetrahydro-1H-3-benzazepine

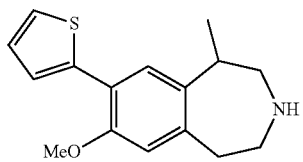 [SMILES: COc1cc2c(cc1-c1cccs1)C(C)CNCC2]

N-Trifluoroacetyl-7-methoxy-1-methyl-8-(2-thienyl)-2,3,4,5-tetrahydro-1H-3-benzazepine A solution of N-trifluoromethylacetyl-8-bromo-7-methoxy-1-methyl-1,2,4,5-tetrahydro-3H-3-benzazepine (51 mg, 0.14 mmol) in 1,4-dioxane (2 mL) was treated with thiophene-2-boronic acid (36 mg, 0.28 mmol), $K_2CO_3$ (58 mg, 0.42 mmol), water (0.1 mL), Pd(PPh$_3$)$_4$ (16 mg, 0.014 mmol) and stirred overnight at 100 C. The product mixture was diluted with EtOAc, filtered, absorbed on silica and purified by flash chromatography (10% EtOAc in hexane, silica) resulting in 28 mg of a yellow solid. MS calculated for $C_{18}H_{18}F_3NO_2S+H$: 370, observed: 370.

7-Methoxy-1-methyl-8-(2-thienyl)-2,3,4,5-tetrahydro-1H-3-benzazepine

A solution of N-trifluoroacetyl-7-methoxy-1-methyl-8-(2-thienyl)-2,3,4,5-tetrahydro-1H-3-benzazepine (28 mg, 0.076 mmol) in methanol (2 mL) was treated with 15% aqueous NaOH (2 mL), and stirred 0.5 hours at 50 C. The product mixture was diluted with water (5 mL), extracted twice with EtOAc (5 mL), the combined organic phases were washed with brine (5 mL), dried with $Na_2SO_4$ and concentrated to give 18 mg of a yellow oil. 1H NMR (400 MHz, $CDCl_3$) d 7.45 (d, J=4 Hz, 1H), 7.39 (s, 1H), 7.27 (d, J=6 Hz, 1H), 7.07 (dd, J=4, 6 Hz, 1H), 6.71 (s, 1H), 3.90 (s, 3H), 3.1-2.9 (m, 6H), 2.80 (m, 1H), 2.22 (bs, 1H), 1.38 (d, J=7 Hz, 3H). MS calculated for $C_{16}H_{19}NOS+H$: 274, observed: 274.

Example 16

(R,S)8-Cyano-7-methoxy-1-methyl-2,3,4,5-tetrahydro-1H-3-benzazepine

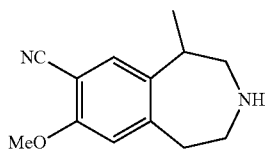 [SMILES: COc1cc2c(cc1C#N)C(C)CNCC2]

N-Trifluoroacetyl-8-cyano-7-methoxy-1-methyl-2,3,4,5-tetrahydro-1H-3-benzazepine A solution of N-trifluoroacetyl-8-bromo-7-methoxy-1-methyl-2,3,4,5-tetrahydro-1H-3-benzazepine (18 mg, 0.05 mmol) in dimethylformamide (1 mL) was treated with CuCN (20 mg, 0.24 mmol) and the mixture was microwaved at 200 C for 0.5 hours. The product mixture was diluted with water (5 mL), extracted twice with EtOAc (5 mL), the combined organic phases were washed with brine (5 mL), dried with $Na_2SO_4$ and concentrated. Flash chromatography (35% EtOAc in hexane, silica) resulted in 10 mg of a clear oil. MS calculated for $C_{15}H_{15}F_3N_2O_2$+H: 313, observed: 313.

8-Cyano-7-methoxy-1-methyl-2,3,4,5-tetrahydro-1H-3-benzazepine

A solution of N-trifluoroacetyl-8-cyano-7-methoxy-1-methyl-2,3,4,5-tetrahydro-1H-3-benzazepine (10 mg, 0.032 mmol) in methanol (2 mL) was treated with 15% aqueous NaOH (2 mL), and stirred 1 hour at 50 C. The product mixture was diluted with water (5 mL), extracted twice with EtOAc (5 mL), the combined organic phases were washed with brine (5 mL), dried with $Na_2SO_4$ and concentrated to give 6.0 mg of a white solid. 1H NMR (400 MHz, $CD_3OD$) d 7.33 (s, 1H, 6.93 (s, 1H), 3.91 (s, 3H), 3.18-2.97 (m, 5H), 2.80 (m, 1H), 2.60 (m, 1H), 1.33 (d, J=8 Hz, 3H). MS calculated for $C_{13}H_{16}N_2O$+H: 217, observed: 217.

Example 17

(R,S)8-bromo-1-cyclopropyl-7-methoxy-2,3,4,5-tetrahydro-1H-3-benzazepine

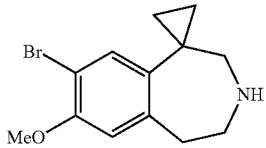 [SMILES: COc1cc2c(cc1Br)C1(CC1)CNCC2]

N-Trifluoroacetyl-1-cyclopropyl-7-ethoxy-2,3,4,5-tetrahydro-1H-3-benzazepine A solution of diethyl zinc (1 mL, 1M in hexanes) in dichloromethane (1 mL) at 0 C was treated with trifluoroacetic acid in dichloromethane (0.5 mL) and the mixture stirred for 15 min. Diiodomethane (0.280 g, 1.0 mmol) in dichloromethane (0.5 mL) was then added and stirred for 15 minutes. N-Trifluoroacetyl-7-methoxy-1-methylene-2,3,4,5-tetrahydro-1H-3-benzazepine (0.075 g, 0.26 mmol) in dichloromethane (1 mL) was added and the mixture stirred for 30 minutes at 0 C and then for 2 hours at 20 C. The product mixture was quenched with aqueous saturated $NH_4Cl$ (5 mL), extracted twice with $CH_2Cl_2$ (20 mL), washed with saturated aqueous $NaHCO_3$ (10 mL), washed with $H_2O$ (10 mL), and concentrated. Flash chromatography (7% EtOAc in hexanes, silica) resulted in 0.050 g of a white solid. MS calculated for $C_{15}H_{16}F_3NO_2$+H: 300, observed: 300.

N-Trifluoroacetyl-8-bromo-1-cyclopropyl-7-methoxy-2,3,4,5-tetrahydro-1H-3-benzazepine A solution of N-trifluoroacetyl-1-cyclopropyl-7-methoxy-2,3,4,5-tetrahydro-1H-3-benzazepine (0.025 g, 0.08 mmol) in acetonitrile (1 mL) was treated with N-bromosuccinimide (0.032 g, 0.18 mmol) and stirred for 2 hrs. at 50 C. The product mixture was concentrated and then purified by flash chromatography (10% EtOAc in hexanes, silica) resulting in 0.014 g of a white solid. MS calculated for $C_{15}H_{15}BrF_3NO_2$+H: 378, observed: 378.

8-bromo-1-cyclopropyl-7-methoxy-2,3,4,5-tetrahydro-1H-3-benzazepine

A solution of N-trifluoroacetyl-8-bromo-1-cyclopropyl-7-methoxy-2,34,5-tetrahydro-1H-3-benzazepine (0.014 g, 0.037 mmol) in methanol (1 mL) was treated with 15% aqueous NaOH (1 mL), and stirred for 2 hours at 50 C. The product mixture was diluted with brine (10 mL), extracted twice with EtOAc (10 mL), dried with $MgSO_4$, and concentrated to give 0.008 g of a clear oil. 1H NMR (400 MHz, $CD_3OD$) d 7.26 (s, 1H), 6.78 (s, 1H), 3.83 (s, 3H), 3.02 (m, 2H), 2.92 (m, 2H), 2.67 (s, 2H), 0.91 (m, 2H), 0.85 (m, 2H). MS calculated for $C_{13}H_{16}BrNO$+H: 282, observed: 282.

Example 18

(R,S)8-bromo-1-hydroxymethyl-7-methoxy-2,3,4,5-tetrahydro-1H-3-benzazepine

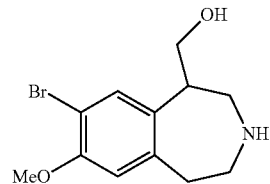 [SMILES: COc1cc2c(cc1Br)C(CO)CNCC2]

N-Trifluoroacetyl-1-hydroxymethyl-7-methoxy-2,3,4,5-tetrahydro-1H-3-benzazepine A solution of N-trifluoroacetyl-7-methoxy-1-methylene-2,3,4,5-tetrahydro-1H-3-benzazepine (0.100 g, 0.35 mmol) in tetrahydrofuran (1 mL) was treated with $BH_3$-THF complex (0.36 mL, 1M in THF), and stirred for 30 min. at 20 C. Water (0.5 mL), saturated aqueous $NaHCO_3$ (0.5 mL), and 30% $H_2O_2$ (0.2 mL) were added sequentially and the reaction stirred for 30 min. at 20 C. The product mixture was diluted with EtOAc (10 mL), washed with brine (10 mL), and concentrated. Flash chromatography (33% EtOAc in hexane, silica) resulted in 0.035 g of a clear oil. MS calculated for $C_{14}H_{16}F_3NO_3$+H: 304, observed: 304.

N-Trifluoroacetyl-8-bromo-1-hydroxymethyl-7-methoxy-2,3,4,5-tetrahydro-1H-3-benzazepine A solution of N-trifluoromethylacetyl-1-hydroxymethyl-7-methoxy-2,3,4,5-tetrahydro-1H-3-benzazepine (0.035 g, 0.12 mmol) in acetonitrile (1 mL) was treated with N-bromosuccinimide (0.025 g, 0.14 mmol), and stirred for 30 min. at 20 C. The product mixture was concentrated and then purified by flash chromatography (33% EtOAc in hexane, silica) resulting in 0.019 g clear oil. MS calculated for $C_{14}H_{15}BrF_3NO_3$+H: 382, observed: 382.

8-bromo-1-hydroxymethyl-7-methoxy-2,3,4,5-tetrahydro-1H-3-benzazepine

A solution of N-trifluoroacetyl-8-bromo-1-hydroxymethyl-7-methoxy-2,3,4,5-tetrahydro-1H-3-benzazepine (0.009 g, 0.024 mmol) in methanol (1 mL) was treated with 15% aqueous NaOH (1 mL), and stirred for 1 hour at 50 C. The product mixture was diluted with brine (5 mL), extracted twice with EtOAc (5 mL), dried with MgSO$_4$, and concentrated to give 0.006 g clear oil. 1H NMR (400 MHz, CD$_3$OD) d 7.28 (s, 1H), 6.79 (s, 1H), 3.84 (m, 2H), 3.0-2.8 (m, 7H). MS calculated for C$_{12}$H$_{16}$BrNO$_2$+H: 286, observed: 286.

Example 19

(R,S)8-Bromo-1-ethyl-7-methoxy-2,3,4,5-tetrahydro-1H-3-benzazepine

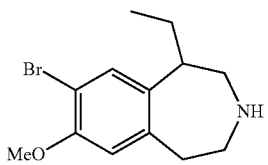 [SMILES: CCC1CNCCc2cc(OC)c(Br)cc21]

N-Crotyl, N-trifluoroacetyl-2-iodo-5-methoxyphenethylamine

A solution of N-trifluoroacetyl-2-iodo-5-methoxyphenethylamine (6.68 g, 17.9 mmol) in toluene (100 mL) was treated with K$_2$CO$_3$ (3.22 g, 23.3 mmol), KOH (3.01 g, 53.7 mmol), n-Bu$_4$NBr (0.580 g, 1.80 mmol) and crotyl bromide (3.15 g, 23.3 mmol). The mixture was stirred at 75 C for 16 hours, cooled to 20 C, diluted with Et$_2$O (500 mL), washed with 10% aqueous HCl (500 mL) and concentrated. Flash chromatography (10% EtOAc in hexane, silica) resulted in 5.22 g of a clear oil. MS calculated for C$_{15}$H$_{17}$F$_3$INO$_2$+H: 428, observed: 428.

N-Trifluoroacetyl-1-ethylene-7-methoxy-2,3,4,5-tetrahydro-1H-3-benzazepine

A solution of N-crotyl, N-trifluoroacetyl-2-iodo-5-methoxyphenethylamine (5.20 g, 12.2 mmol) in dimethylformamide (80 mL) was treated with KOAc (3.59 g, 36.6 mmol), n-Bu$_4$NBr (3.93 g, 12.2 mmol), PPh$_3$ (0.320 g, 1.22 mmol), Pd(OAc)$_2$ (0.137 g, 0.61 mmol) and stirred overnight at 90 C. The product mixture was cooled to 20 C, diluted with water (200 mL), extracted twice with ether (500 mL), the combined organic phases washed twice with brine (200 mL), and concentrated. Flash chromatography (10% EtOAc in hexane, silica) resulted in 2.29 g of a clear oil, which consists of a mixture of olefinic isomers. MS calculated for C$_{15}$H$_{16}$F$_3$NO$_2$+H: 300, observed: 300.

N-Trifluoroacetyl-1-ethyl-7-methoxy-2,3,4,5-tetrahydro-1H-3-benzazepine

A solution of N-trifluoroacetyl-1-ethylene-7-methoxy-2,3,4,5-tetrahydro-1H-3-benzazepine (2.29 g, 7.65 mmol) in methanol (100 mL) was treated with 10% Pd/C (4.0 g, 0.77 mmol)) and stirred overnight under an atmosphere of hydrogen. The product mixture was filtered through a pad of celite and silica, and the solvent removed to give 2.14 g of a clear oil. MS calculated for C$_{15}$H$_{18}$F$_3$NO$_2$+H: 302, observed: 302.

N-Trifluoroacetyl-8-bromo-1-ethyl-7-methoxy-2,3,4,5-tetrahydro-1H-3-benzazepine

A solution of N-trifluorolacetyl-1-ethyl-7-methoxy-2,3,4,5-tetrahydro-1H-3-benzazepine (0.710 g, 2.36 mmol) in acetonitrile (20 mL) was treated with N-bromosuccinimide (0.504 g, 2.83 mmol), and stirred overnight at 20 C. The product mixture was concentrated, diluted with EtOAc (100 mL), washed with water (50 mL) and brine (50 mL), dried with Na$_2$SO$_4$ and concentrated. Flash chromatography (10% EtOAc in hexanes, silica) resulted in 0.561 g of a clear oil. MS calculated for C$_{15}$H$_{17}$BrF$_3$NO$_2$+H: 380, observed: 380.

8-Bromo-1-ethyl-7-methoxy-2,3,4,5-tetrahydro-1H-3-benzazepine

A solution of N-trifluoroacetyl-8-bromo-1-ethyl-7-methoxy-2,3,4,5-tetrahydro-1H-3-benzazepine (0.561 g, 1.48 mmol) in methanol (30 mL) was treated with 15% aqueous NaOH (30 mL), and stirred overnight at 20 C. The product mixture was diluted with brine (100 mL), extracted twice with EtOAc (200 mL), dried with MgSO$_4$, and concentrated to give 0.412 g of a clear oil. 1H NMR (400 MHz, CD$_3$OD) d 7.24 (s, 1H), 6.76 (s, 1H), 3.83 (s, 3H), 3.02 (m, 3H), 2.91 (s, 1H), 2.85-2.76 (m, 3H), 2.63 (m, 1H), 1.78 (m, 1H), 1.72 (m, 1H), 0.94 (dd, J=8, 8 Hz, 3H). MS calculated for C$_{13}$H$_{18}$BrNO+H: 284, observed: 284.

Example 20

(R,S)8-Chloro-1-ethyl-7-methoxy-2,3,4,5-tetrahydro-1H-3-benzazepine

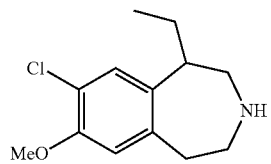 [SMILES: CCC1CNCCc2cc(OC)c(Cl)cc21]

N-Trifluoroacetyl-8-chloro-1-ethyl-7-methoxy-2,3,4,5-tetrahydro-1H-3-benzazepine A solution of N-trifluorolacetyl-1-ethyl-7-methoxy-2,3,4,5-tetrahydro-1H-3-benzazepine (0.600 g, 1.99 mmol) in acetonitrile (20 mL) was treated with N-chlorosuccinimide (0.057 g, 0.32 mmol), and stirred overnight at 60 C. The product mixture was concentrated, diluted with EtOAc (100 mL), washed with water (50 mL) and brine (50 mL), dried with Na$_2$SO$_4$ and concentrated. Flash chromatography (10% EtOAc in hexanes, silica) resulted in 0.421 g of a clear oil. MS calculated for C$_{15}$H$_{17}$ClF$_3$NO$_2$+H: 336, observed: 336.

8-Chloro-1-ethyl-7-methoxy-2,3,4,5-tetrahydro-1H-3-benzazepine

A solution of N-trifluoroacetyl-8-chloro-1-ethyl-7-methoxy-2,3,4,5-tetrahydro-1H-3-benzazepine (0.421 g, 1.25 mmol) in methanol (30 mL) was treated with 15% aqueous NaOH (30 mL), and stirred overnight at 20 C. The product mixture was diluted with brine (100 mL), extracted twice with EtOAc (200 mL), dried with MgSO$_4$, and concentrated to give 0.241 g of a clear oil. 1H NMR (400 MHz, CD$_3$OD) d 7.05 (s, 1H), 6.79 (s, 1H), 3.84 (s, 3H), 3.03 (m, 3H), 2.91 (s, 1H), 2.86-2.76 (m, 3H), 2.64 (m, 1H), 1.81 (m, 1H), 1.72 (m, 1H), 0.93 (dd, J=8, 8 Hz, 3H). MS calculated for C$_{13}$H$_{18}$ClNO+H: 240, observed: 240.

Example 21

(R,S)8-Bromo-1-isopropyl-7-methoxy-2,3,4,5-tetrahydro-1H-3-benzazepine

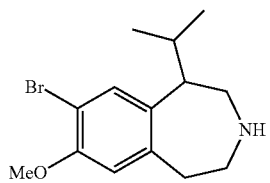 [SMILES: COc1cc2c(cc1Br)C(C(C)C)CNCC2]

N-(3-methylbut-2-enyl), N-trifluoroacetyl-2-iodo-5-methoxyphenethylamine

A solution of N-trifluoroacetyl-2-iodo-5-methoxyphenethylamine (0.700 g, 1.88 mmol) in toluene (25 mL) was treated with K$_2$CO$_3$ (0.340 g, 2.4 mmol), KOH (0.210 g, 3.76 mmol), n-Bu$_4$NBr (0.060 g, 0.19 mmol) and 4-bromo-2-methyl-2-butene (0.364 g, 2.44 mmol). The mixture was stirred at 80 C for 3 hours, cooled to 20 C, diluted with ether (100 mL), washed with 10% HCl (50 mL) and concentrated. Flash chromatography (10% EtOAc in hexane, silica) resulted in 0.272 g of a clear oil. 1H NMR (400 MHz, CDCl$_3$, mixture of rotamers) d 7.65 (m, 1H), 6.75 (m, 1H), 6.54 (m, 1H), 5.20 (m, 0.4H), 5.0 (m, 0.6H), 4.10 (m, 1H), 3.82 (m, 1H), 3.76 (d, 2H), 3.50 (m, 2H), 3.02 (m, 2H), 1.75 (m, 3H), 1.66 (m, 3H).

N-Trifluoroacetyl-1-isopropylene-7-methoxy-2,3,9,5-tetrahydro-1H-3-benzazepine

A solution of N-(3-methylbut-2-enyl), N-trifluoroacetyl-2-iodo-5-methoxyphenethylamine (0.0272 g, 0.62 mmol) in dimethylformamide (12 mL) was treated with KOAc (0.183 g, 1.86 mmol), n-Bu$_4$NBr (0.200 g, 0.062 mmol), PPh$_3$ (0.016 g, 0.062 mmol), Pd(OAc)$_2$ (0.183 g, 1.86 mmol) and stirred overnight at 90 C. The product mixture was cooled to 20 C, diluted with water (50 mL), extracted twice with ether (50 mL), the combined organic phases were washed with brine (50 mL), and concentrated. Flash chromatography (10% EtOAc in hexane, silica) resulted in 0.096 g of a clear oil. MS calculated for C$_{16}$H$_{18}$F$_3$NO$_2$+H: 314, observed: 314.

N-Trifluoroacetyl-1-isopropyl-7-methoxy-2,3,4,5-tetrahydro-1H-3-benzazepine

A solution of N-trifluoroacetyl-1-isopropylene-7-methoxy-2,3,4,5-tetrahydro-1H-3-benzazepine (0.096 g, 0.31 mmol) in ethanol (2 mL) was treated with 10% Pd/C (0.033 g, 0.031 mmol)) and stirred overnight under an atmosphere of hydrogen. The product mixture was filtered through a pad of celite and silica, and the solvent removed to give 0.091 g of a clear oil. MS calculated for C$_{16}$H$_{20}$F$_3$NO$_2$+H: 316, observed: 316.

N-Trifluoroacetyl-8-bromo-1-isopropyl-7-methoxy-2,3,4,5-tetrahydro-1H-3-benzazepine A solution of N-trifluorolacetyl-1-isopropyl-7-methoxy-2,3,4,5-tetrahydro-1H-3-benzazepine (0.091 g, 0.29 mmol) in acetonitrile (3 mL) was treated with N-bromosuccinimide (0.057 g, 0.32 mmol), and stirred overnight at 20 C. After removing the solvent, flash chromatography (10% EtOAc in hexanes, silica) resulted in 0.056 g of a clear oil. MS calculated for C$_{16}$H$_{19}$BrF$_3$NO$_2$+H: 394, observed: 394.

8-Bromo-1-isopropyl-7-methoxy-2,3,4,5-tetrahydro-1H-3-benzazepine

A solution of N-trifluoroacetyl-8-bromo-1-isopropyl-7-methoxy-2,3,4,5-tetrahydro-1H-3-benzazepine (0.013 g, 0.03 mmol) methanol (0.5 mL) was treated with 15% aqueous NaOH (0.5 mL), and stirred overnight at 20 C. The product mixture was diluted with brine (5 mL), extracted twice with EtOAc (5 mL), dried with MgSO$_4$, and concentrated to give 0.10 g of a clear oil. 1H NMR (400 MHz, CD$_3$OD) d 7.08 (s, 1H), 6.64 (s, 1H), 3.72 (s, 3H), 3.2-3.10 (m, 3H), 2.7-2.5 (m, 3H), (m, 2H), 0.96 (d, 3H), 0.63 (d, 3H). MS calculated for C$_{14}$H$_{20}$BrNO+H: 298, observed: 298.

Example 22

(R,S)8-Bromo-7-hydroxy-1-isopropyl-2,3,4,5-tetrahydro-1H-3-benzazepine

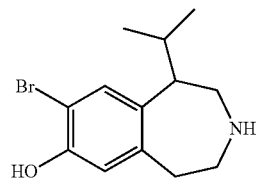 [SMILES: CC(C)C1CNCCc2cc(O)c(Br)cc21]

N-Trifluoroacetyl-8-bromo-7-hydroxy-1-isopropyl-2,3,4,5-tetrahydro-1H-3-benzazepine A solution of N-trifluoroacetyl-8-bromo-1-isopropyl-7-methoxy-2,3,4,5-tetrahydro-1H-3-benzazepine (0.041 g, 0.10 mmol) in dichloromethane (1 mL) was treated with BBr$_3$ (0.32 ml, 1.0 M solution in CH$_2$Cl$_2$) and stirred overnight at 20 C. The excess BBr$_3$ is quenched with water and the resulting mixture diluted with ether (50 mL), washed twice with saturated aqueous Na$_2$CO$_3$ (20 mL) and concentrated. Flash chromatography (20% EtOAc in hexanes, silica) resulted in 0.037 g clear oil. MS calculated for C$_{15}$H$_{17}$BrF$_3$NO$_2$+H: 380, observed: 380.

8-Bromo-7-hydroxy-1-isopropyl-2,3,4,5-tetrahydro-1H-3-benzazepine

A solution of N-trifluoroacetyl-8-bromo-7-hydroxy-1-isopropyl-2,3,4,5-tetrahydro-1H-3-benzazepine (0.018 g, 0.047 mmol) in methanol (1 mL) was treated with 15% aqueous NaOH (1 mL), and stirred for 3 hours at 50 C. The product mixture was brought to pH 7-8 with 10% aqueous HCl, extracted three times with EtOAc (50 mL), dried with MgSO$_4$, and concentrated to give 0.013 g of a white solid. 1H NMR (400 MHz, CD$_3$OD) d 7.10 (s, 1H), 6.60 (s, 1H), 3.30 (m, 1H), 3.2-3.0 (m, 2H), 2.78 (m, 1H), 2.7-2.5 (m, 2H), 2.3-2.1 (m, 2H), 1.05 (d, 3H), 0.73 (d, 3H). MS calculated for C$_{13}$H$_{18}$BrNO+H: 284, observed: 284.

Example 23

(R,S)7-Allyloxy-8-bromo-1-isopropyl-2,3,4,5-tetrahydro-1H-3-benzazepine

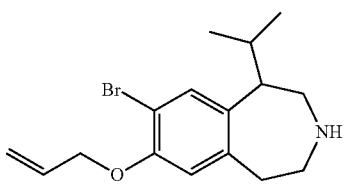 [SMILES: C=CCOc1cc2c(cc1Br)C(C(C)C)CNCC2]

N-Trifluoroacetyl-7-allyloxy-8-bromo-1-isopropyl-2,3,4,5-tetrahydro-1H-3-benzazepine A solution of N-trifluoroacetyl-8-bromo-7-hydroxy-1-isopropyl-2,3,4,5-tetrahydro-1H-3-benzazepine (0.017 g, 0.045 mmol) in dichloromethane (1 mL) was treated with N''''-tert-butyl-N,N,N',N',N'',N''-hexamethylphosphorimidic triamide (0.016 g, 0.068 mmol), allyl bromide (0.011 g, 0.09 mmol) and stirred for 3 hours at 20 C. The product mixture was diluted with 10% aqueous HCl, extracted twice with dichloromethane (20 mL), and concentrated. Flash chromatography (10% EtOAc in hexanes, silica) resulted in 0.011 g of a clear oil. MS calculated for C$_{18}$H$_{21}$BrF$_3$NO$_2$+H: 420, observed: 420.

7-Allyloxy-8-bromo-1-isopropyl-2,3,4,5-tetrahydro-1H-3-benzazepine

A solution of N-trifluoroacetyl-7-allyloxy-8-bromo-1-isopropyl-2,3,4,5-tetrahydro-1H-3-benzazepine (0.011 g, 0.026 mmol) in methanol (0.5 mL) was treated with of 15% aqueous NaOH (0.5 mL), and stirred for 3 hours at 50 C. The product mixture was diluted with brine (5 mL), extracted twice with EtOAc (5 mL), dried with MgSO$_4$, and concentrated to give 0.010 g of a clear oil. 1H NMR (400 MHz, CD$_3$OD) d 7.09 (s, 1H), 6.62 (s, 1H), 5.94 (m, 1H), 5.32 (dd, 1H), 5.12 (dd, 1H), 4.46 (d, 2H), 3.19 (m, 1H), 3.05 (m, 2H), 2.66 (m, 1H), 2.5 (bm, 2H), 2.3-2.1 (m, 2H), 0.95 (d, 3H), 0.63 (d, 3H). MS calculated for C$_{16}$H$_{22}$BrNO+H: 324, observed: 324.

Example 24

8-Bromo-7-methoxy-1,4-dimethyl-2,3,4,5-tetrahydro-1H-3-benzazepine

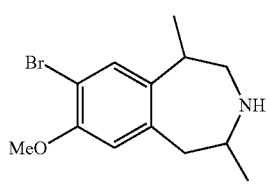 [SMILES: COc1cc2c(cc1Br)C(C)CNC(C)C2]

N-Trifluoroacetyl-1-(3-methoxyphenyl)-2-propylamine

A solution of 1-(3-methoxyphenyl)-2-propylamine (3.59 g, 21.7 mmol) in dichloromethane (75 mL) at 0 C, was treated with pyridine (2.1 mL, 28.2 mmol), trifluoracetic anhydride (5.9 g, 28.2 mmol), and then stirred for 3 hours while warming to 20 C. The product mixture was diluted with EtOAc (300 mL), washed sequentially with 10% aqueous HCl (100 mL), water (100 mL), brine (100 mL), dried with Na$_2$SO$_4$ and concentrated. Flash chromatography (20% EtOAc in hexane, silica) resulted in 4.29 g of a yellow solid. 1H NMR (400 MHz, CD$_3$OD) d 7.17 (dd, J=8, 8 Hz, 1H), 6.76 (m, 3H), 4.19 (m, 1H), 3.77 (s, 3H), 2.78 (m, 2H), 1.21 (d, 1=7 Hz, 2H).

N-Trifluoroacetyl-1-(2-iodo-5-methoxyphenyl)-2-propylamine

A solution of N-trifluoroacetyl-1-(3-methoxyphenyl)-2-propylamine (4.29 g, 15.7 mmol) in methanol (100 mL) was cooled to –78 C and treated with CaCO$_3$ (3.17 g, 31.4 mmol), followed by a solution of ICl (6.37 g, 39.3 mmol) in methanol (50 mL). The reaction was allowed to warm to 20 C while stirring overnight. The product mixture was filtered, concentrated, dissolved in EtOAc (200 mL), washed twice with 5% aqueous sodium bisulfite (100 mL), once with brine (100 mL), dried with Na$_2$SO$_4$ and concentrated to give 6.72 g of a white solid powder. MS calculated for C$_{12}$H$_{13}$F$_3$INO$_2$+H: 388, observed: 388.

N-Allyl, N-trifluoroacetyl-1-(2-iodo-5-methoxyphenyl)-2-propylamine

A solution of N-trifluoroacetyl-1-(2-iodo-5-methoxyphenyl)-2-propylamine (6.09 g, 15.7 mmol) in toluene (450 mL) was treated with K$_2$CO$_3$ (2.82 g, 20.4 mmol), KOH (2.45 g, 47.1 mmol), n-Bu$_4$NBr (0.506 g, 1.57 mmol) and allyl bromide (2.47 g, 20.4 mmol), and stirred overnight at 80 C. The product mixture was acidified with 10% aqueous HCl, separated, the aqueous phase extracted with ether (500 mL), the combined organic phases were washed with brine (200 mL), dried with Na$_2$SO$_4$ and concentrated to give 4.45 g of a brown oil.

N-Trifluoroacetyl-7-methoxy-4-methyl-1-methylene-2,3,4,5-tetrahydro-1H-3-benzazepine A solution of N-allyl, N-trifluoroacetyl-1-(2-iodo-5-methoxyphenyl)-2-propylamine (4.45 g, 10.8 mmol) in dimethylformamide (120 mL) was treated with KOAc (3.17 g, 32.3 mmol), n-Bu$_4$NBr (3.47 g, 10.8 mmol), PPh$_3$ (0.283 g, 1.08 mmol), Pd(OAc)$_2$ (0.242 g, 1.08 mmol) and stirred overnight at 80 C. The product mixture was cooled to 20 C, filtered, diluted with water (200 mL), extracted with ether (3×200 mL), the combined organic phases washed with water (100 mL), brine (100 mL), dried with Na$_2$SO$_4$ and concentrated. Flash chromatography (10% EtOAc in hexane, silica) resulted in 1.39 g of a yellow oil.

N-Trifluoroacetyl-1,4-dimethyl-7-methoxy-2,3,4,5-tetrahydro-1H-3-benzazepine A solution of N-trifluoroacetyl-7-methoxy-4-methyl-1-methylene-2,3,4,5-tetrahydro-1H-3-benzazepine (1.39 g, 4.64 mmol) in ethanol (40 mL) was treated with 10% Pd/C (0.49 g, 0.46 mmol) and stirred overnight under an atmosphere of hydrogen. The product mixture was filtered through a pad of celite and silica and then concentrated. Flash chromatography (20% EtOAc in hexane, silica) resulted in 0.77 g of a clear oil. 1H NMR (400 MHz, CDCl₃, mixture of rotamers) d 7.06 (m, 1H), 6.71 (m, 1H), 6.63 (m, 1H), 4.38 (bm, 1H), 3.8 (s, 3H), 3.6 (m, 1H), 3.25 (m, 1H), 3.18 (bm, 2H), 2.72 (m, 1H), 1.34 (m, 3H) 1.22 (m, 3H).

N-Trifluoroacetyl-8-bromo-1,4-dimethyl-7-methoxy-2,3,4,5-tetrahydro-1H-3-benzazepine A solution N-trifluoroacetyl-1,4-dimethyl-7-methoxy-2,3,4,5-tetrahydro-1H-3-benzazepine (0.452 g, 1.50 mmol) in acetonitrile (20 mL) was treated with N-bromosuccinimide (0.294 g, 1.65 mmol) and stirred overnight at 20 C. The product mixture was diluted with EtOAc (100 mL), washed with sodium bisulfite (50 mL) and brine (50 mL), dried with Na₂SO₄ and concentrated. Flash chromatography (20% EtOAc in hexane, silica) resulted in a clear oil. 1H NMR (400 MHz, CDCl₃, mixture of rotamers) d 7.32 (s, 1H), 6.62 (m, 1H), 4.37 (m, 1H), 3.87 (s, 3H), 3.81 (m, 1H), 3.28-3.10 (m, 3H), 2.73 (m, 1H), 1.31 (m, 3H), 1.25 (m, 3H).

8-Bromo-1,4-dimethyl-7-methoxy-2,3,4,5-tetrahydro-1H-3-benzazepine

A solution of N-trifluoroacetyl-8-bromo-1,4-dimethyl-7-methoxy-2,3,4,5-tetrahydro-1H-3-benzazepine (21 mg, 0.055 mmol) in methanol (2 mL) was treated with 15% aqueous NaOH (2 mL), and stirred overnight at 20 C. The product mixture was diluted with water (5 mL), extracted twice with EtOAc (10 mL), the combined organic phases were washed with brine (10 mL), dried with Na₂SO₄ and concentrated to give 11 mg of a clear oil. 1H NMR (400 MHz, CDCl₃) d 7.29 (s, 1H), 6.64 (s, 1H), 3.88 (s, 3H), 3.02 (m, 2H), 2.89 (dd, J=9, 14 Hz, 1H), 2.80 (m, 1H), 2.67 (d, J=14 Hz, 1H), 2.53 (dd, J=10, 13, 1H) 1.30 (d, J=7 Hz, 3H), 1.19 (d, J=6 Hz, 3H). MS calculated for C₁₃H₁₈BrNO+H: 284, observed: 284.

Example 25

7-Allyloxy-8-bromo-1,4-dimethyl-2,3,4,5-tetrahydro-1H-3-benzazepine

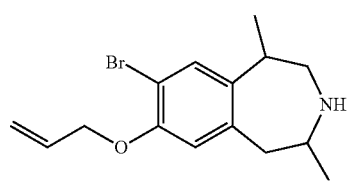 [SMILES: C=CCOc1cc2c(cc1Br)C(C)CNC(C)C2]

N-Trifluoroacetyl-8-bromo-1,4-dimethyl-7-hydroxy-2,3,4,5-tetrahydro-1H-3-benzazepine A solution of N-trifluoroacetyl-8-bromo-1,4-dimethyl-7-methoxy-2,3,4,5-tetrahydro-1H-3-benzazepine (0.383 g, 1.01 mmol) in dichloromethane (30 mL) was treated with BBr₃ (2.35 mL of a 1.0M solution in CH₂Cl₂, 2.35 mmol) and stirred overnight while warming to 20 C. The excess BBr₃ is quenched with water, and the resulting mixture was diluted with ether (100 mL), washed with saturated aqueous Na₂CO₃ (50 mL) and brine (50 mL), dried with Na₂SO₄ and concentrated. Flash chromatography (15% EtOAc in hexane, silica) resulted in 0.302 g of a white solid. 1H NMR (400 MHz, CDCl₃, mixture of rotamers) d 7.22 (m, 1H), 6.77 (m, 1H), 5.34 (s, 1H), 4.35 (m, 1H), 3.62 (m, 1H), 3.24 (m, 1H), 3.13 (m, 2H), 2.69 (m, 1H), 1.31 (m, 3H), 1.22 (m, 3H).

N-Trifluoroacetyl-7-allyloxy-8-bromo-1,4-dimethyl-2,3,4,5-tetrahydro-1H-3-benzazepine A solution N-trifluoroacetyl-8-bromo-1,4-dimethyl-7-hydroxy-2,3,4,5-tetrahydro-1H-3-benzazepine (0.030 g, 0.082 mmol) in dichloromethane (2 mL) was treated with allyl bromide (0.030 g, 0.246 mmol), DBU (0.037 g, 0.246 mmol) and stirred 2 hours at 20 C. The product mixture was diluted with EtOAc (10 mL), washed with 5% aqueous HCl (2 mL), brine (5 mL), dried with Na₂SO₄ and concentrated. Flash chromatography (15% EtOAc in hexane, silica) resulted in 0.028 g of a clear oil. 1H NMR (400 MHz, CDCl₃, mixture of rotamers) d 7.32 (s, 1H), 6.62 (m, 1H), 6.02 (m, 1H), 5.45 (d, J=17 Hz, 1H), 5.30 (d, J=11 Hz, 1H), 4.58 (s, 2H), 4.36 (m, 1H), 3.62 (m, 1H), 3.23 (m, 1H), 3.11 (m, 1H), 2.81 (d, J=10 Hz, 1H), 2.70 (m, 1H), 1.34 (m, 3H), 1.21 (m, 3H).

7-Allyloxy-8-bromo-1,4-dimethyl-2,3,4,5-tetrahydro-1H-3-benzazepine

A solution of N-trifluoroacetyl-7-allyloxy-8-bromo-1,4-dimethyl-2,3,4,5-tetrahydro-1H-3-benzazepine (0.028 g, 0.069 mmol) in methanol (2 mL) was treated with 15% aqueous NaOH (2 mL), and stirred for 3 hours at 20 C. The product mixture was diluted with water (10 mL), extracted twice with EtOAc (10 mL), the combined organic phases were washed with brine (10 mL), dried with Na₂SO₄ and concentrated to give 0.020 g of a clear oil. 1H NMR (400 MHz, CDCl₃) d 7.30 (s, 1H), 6.64 (s, 1H), 6.06 (m, 1H), 5.47 (d, J=17 Hz, 1H), 5.30 (d, J=11 Hz, 1H), 4.56 (s, 2H), 3.03 (m, 2H), 2.90 (dd, J=9, 14 Hz, 1H), 2.80 (m, 1H), 2.65 (d, J=14 Hz, 1H), 2.55 (dd, J=10, 14 Hz, 1H), 1.77 (bs, 1H), 1.30 (d, J=7 Hz, 3H), 1.20 (d, J=6 Hz, 3H).

Example 26

(R,S)8-Chloro-1-methyl-2,3,4,5-tetrahydro-8H-3-benzazepine

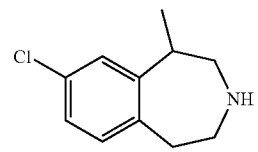

N-Trifluoroacetyl-4-chlorophenethylamine

A solution of 4-chlorophenethylamine (1.0 g, 6.4 mmol) in dichloromethane (20 mL) was cooled to 0 C, treated with pyridine (1.0 mL, 12.8 mmol), trifluoracetic anhydride (1.6 g, 7.7 mmol) and then stirred for 1 hour while warming to 20 C. The product mixture was diluted with EtOAc (100 mL), washed sequentially with 10% aqueous HCl (50 mL), water (50 mL), brine (50 mL), dried with Na₂SO₄ and concentrated to give 1.6 g of a white solid.

N-Trifluoroacetyl-2-iodo-4-chlorophenethylamine

A solution of N-trifluoroacetyl-4-chlorophenethylamine (1.6 g, 6.4 mmol) in dichloromethane (20 mL) was treated with bis(pyridine)iodonium(I)tetrafluoroborate (2.6 g, 7.0 mmol), CF$_3$SO$_3$H (2.1 g, 14.1 mmol) and stirred overnight at 20 C. The product mixture was concentrated, dissolved in EtOAc (100 mL), washed twice with 5% aqueous sodium bisulfite (50 mL), twice with saturated aqueous NaHCO$_3$, (50 mL) once with brine (50 mL), dried with Na$_2$SO$_4$ and concentrated to give 0.94 g of a clear oil. MS calculated for C$_{10}$H$_8$ClF$_3$INO+H: 378, observed: 378.

N-Allyl, N-trifluoroacetyl-2-iodo-4-chlorophenethylamine

A solution of N-trifluoroacetyl-2-iodo-4-chlorophenethylamine (0.94 g, 2.4 mmol) in toluene (25 mL) was treated with K$_2$CO$_3$ (0.43 g, 3.12 mmol), KOH (0.40 g, 7.2 mmol), n-Bu$_4$NBr (0.077 g, 0.24 mmol) and allyl bromide (0.43 g, 3.6 mmol) sequentially. The mixture was stirred at 80 C for 3.5 hours, cooled to 20 C and acidified with 10% aqueous HCl. The phases were separated, the aqueous phase extracted with ether (100 mL), the combined organic phases were washed with brine (50 mL), dried with Na$_2$SO$_4$ and concentrated to give 0.76 g of a clear oil. MS calculated for C$_{13}$H$_{12}$ClF$_3$INO+H: 418, observed: 418.

N-Trifluoroacetyl-8-chloro-1-methylene-2,3,4,5-tetrahydro-1H-3-benzazepine

A solution of N-allyl, N-trifluoroacetyl-2-iodo-4-chlorophenethylamine (0.76 g, 1.8 mmol) in dimethylformamide (20 mL) was treated with KOAc (0.53 g, 5.4 mmol), n-Bu$_4$NBr (0.58 g, 1.8 mmol), PPh$_3$ (0.047 g, 0.18 mmol), Pd(OAc)$_2$ (0.041 g, 0.18 mmol) and stirred overnight at 105 C. The product mixture was cooled to 20 C, filtered, diluted with water (100 mL), extracted with ether (3×100 mL), the combined organic phases washed with water (100 mL), brine (100 mL), dried with Na$_2$SO$_4$ and concentrated. Flash chromatography (10% EtOAc in hexane, silica) resulted in 0.228 g of a clear oil.
1H NMR (400 MHz, CDCl$_3$) d 7.29 (s, 1H), 7.18 (m, 1H), 7.04 (m, 1H), 5.38 (m, 2H), 5.40 (d, J=16 Hz, 2H), 3.80 (m, 2H), 3.00 (m, 2H). MS calculated for C$_{13}$H$_{11}$ClF$_3$NO+H: 290, observed: 290.

N-Trifluoroacetyl-8-chloro-1-methyl-2,3,4,5-tetrahydro-1H-3-benzazepine

A solution of N-trifluoroacetyl-8-chloro-1-methylene-2,3,4,5-trihydro-1H-3-benzazepine (0.16 g, 0.55 mmol) in methanol (10 mL) was treated with 10% Pd/C (0.02 g) and stirred 30 minutes under an atmosphere of hydrogen. The product mixture was filtered, concentrated and purified by flash chromatography (5% EtOAc in hexane, silica) resulting in 0.057 g of a white solid. MS calculated for C$_{13}$H$_{13}$ClF$_3$NO+H: 292, observed: 292.

8-Chloro-1-methyl-2,3,4,5-tetrahydro-1H-3-benzazepine

A solution of N-trifluoroacetyl-8-chloro-1-methyl-2,3,4,5-tetrahydro-1H-3-benzazepine (65 mg, 0.22 mmol) in methanol (2 mL) was treated with 15% aqueous NaOH (2 mL), and stirred for 3.5 hours at 60 C. The product mixture was concentrated, extracted 3 times with CH$_2$Cl$_2$ (5 mL), dried with Na$_2$SO$_4$ and concentrated to give 35 mg of a clear oil. 1H NMR (400 MHz, CDCl$_3$) d 7.11 (s, 1H), 7.05 (d, J=8 Hz, 1H), 6.98 (d, J=8 Hz, 1H), 3.1-2.9 (m, 6H), 2.71 (m, 1H), 2.68 (bs, 1H), 1.32 (d, J=8 Hz, 3H). MS calculated for C$_{11}$H$_{14}$ClN+H: 196, observed: 196.

Example 27

(R,S)7-(2-Methyl-2H-pyrazol-3-yl)-1-methyl-2,3,4, 5-tetrahydro-1H-3-benzazepine

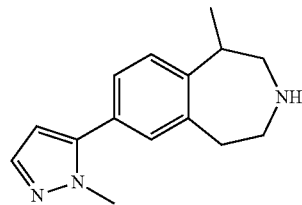 [SMILES: CC1CNCCc2cc(-c3ccnn3C)ccc21]

N-Trifluoroacetyl-7-hydroxy-1-methyl-2,3,4,5-tetrahydro-1H-3-benzazepine

A solution of N-trifluoroacetyl-7-methoxy-1-methyl-2,3, 4,5-tetrahydro-1H-3-benzazepine (0.506 g, 1.76 mmol) in dichloromethane (20 mL) was treated with BBr$_3$ (4.1 mL of a 1.0M solution in CH$_2$Cl$_2$, 4.1 mmol) and stirred overnight while warming to 20 C. The excess BBr$_3$ was quenched with water, and the resulting mixture was diluted with ether (200 mL), washed with Na$_2$CO$_3$ (100 mL) and brine (100 mL), dried with Na$_2$SO$_4$ and concentrated. Flash chromatography (15% EtOAc in hexane, silica) resulted in 0.460 g of a white solid foam. MS calculated for C$_{13}$H$_{14}$F$_3$NO$_2$+H: 274, observed: 274.

N-Trifluoroacetyl-7-hydroxy-1-methyl-2,3,4,5-tetrahydro-1H-3-benzazepine, O-trifluoromethanesulfonate A solution of N-trifluoroacetyl-7-hydroxy-1-methyl-2,3, 4,5-tetrahydro-1H-3-benzazepine (460 mg, 1.76 mmol) in dichloromethane (15 mL) was treated with pyridine (417 mg, 5.27 mmol), trifluoromethanesulfonic anhydride (991 mg, 3.52 mmol) and stirred 1.5 hours at 20 C. The product mixture was diluted with dichloromethane (100 mL), washed with water (50 mL), 5% aqueous HCl (50 mL), saturated aqueous NaHCO$_3$ (50 mL), brine (50 mL), dried with Na$_2$SO$_4$ and concentrated. Flash chromatography (15% EtOAc in hexane, silica) resulted in 658 mg of a clear oil. MS calculated for C$_{14}$H$_{13}$F$_6$NO$_4$S+H: 406, observed: 406.

N-Trifluoroacetyl-7-(2-Methyl-2H-pyrazol-3-yl)-1-methyl-2,3,4,5-tetrahydro-1H-3-benzazepine To a solution of N-trifluoroacetyl-7-hydroxy-1-methyl-2, 3,4,5-tetrahydro-1H-3-benzazepine, O-trifluoromethanesulfonate (100 mg, 0.25 mmol) in dimethylformamide (2 mL) was treated with (2-methyl-2H-pyrazol-3-yl)-tri-n-butyltin (138 mg, 0.37 mmol), LiCl (21 mg, 0.50 mmol), Pd(PPh$_3$)$_2$Cl$_2$ (35 mg, 0.05 mmol) and stirred at 100 C for 4 hours. The product mixture was diluted with EtOAc (20 mL), washed twice with water (10 mL), once with brine (10 mL), dried with Na$_2$SO$_4$ and concentrated. Flash chromatography (30% EtOAc in hexane, silica) resulted in 80 mg of a clear oil. MS calculated for C$_{17}$H$_{18}$F$_3$N$_3$O+H: 338, observed: 338.

7-(2-Methyl-2H-pyrazol-3-yl)-1-methyl-2,3,4,5-tetrahydro-1H-3-benzazepine

A solution of N-trifluoroacetyl-7-(2-Methyl-2H-pyrazol-3-yl)-1-methyl-2,3,4,5-tetrahydro-1H-3-benzazepine (48 mg, 0.14 mmol) in methanol (2 mL) was treated with 15% aqueous NaOH (2 mL), and the solution stirred overnight at 20 C. The product mixture was concentrated, extracted 3 times with $CH_2Cl_2$ (5 mL), dried with $Na_2SO_4$ and the solvent evaporated. Flash chromatography (0-15% MeOH in $CH_2Cl_2$, silica) resulted in 30 mg of a clear oil. 1H NMR (400 MHz, $CDCl_3$) d 7.48 (s, 1H), 7.21 (m, 2H), 7.13 (s, 1H), 6.27 (s, 1H), 3.89 (s, 3H), 3.3-2.9 (m, 9H), 2.79 (dd, J=7, 14 Hz, 1H), 1.40 (d, J=8 Hz, 3H). MS calculated for $C_{15}H_{19}N_3$+H: 242, observed: 242.

Example 28

(R,S)7-(4-Bromo-2-methyl-2H-pyrazol-3-yl)-1-methyl-2,3,4,5-tetrahydro-1H-3-benzazepine

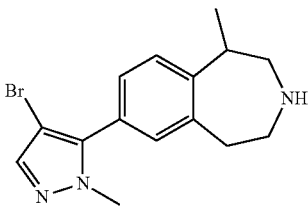 [SMILES: CC1CNCCc2cc(-c3c(Br)cnn3C)ccc21]

N-Trifluoroacetyl-7-(4-bromo-2-Methyl-2H-pyrazol-3-yl)-1-methyl-2,3,4,5-tetrahydro-1H-3-benzazepine To a solution of N-trifluoroacetyl-7-(2-Methyl-2H-pyrazol-3-yl)-1-methyl-2,3,4,5-tetrahydro-1H-3-benzazepine (30 mg, 0.082 mmol) in dichloromethane (1 mL) was treated with N-bromosuccinimide (15.3 mg, 0.086 mmol) and stirred overnight at 20 C. The product mixture was absorbed on silica and purified by flash chromatography (2-5% MeOH in $CH_2Cl_2$, silica) resulting in 37 mg of a white crystalline solid. MS calculated for $C_{17}H_{17}BrF_3N_3O$+H: 416, observed: 416.

7-(4-Bromo-2-methyl-2H-pyrazol-3-yl)-1-methyl-2,3,4,5-tetrahydro-1H-3-benzazepine A solution of N-trifluoroacetyl-7-(4-bromo-2-Methyl-2H-pyrazol-3-yl)-1-methyl-2,3,4,5-tetrahydro-1H-3-benzazepine (37 mg, 0.089 mmol) in methanol (2 mL) was treated with of 15% aqueous NaOH (2 mL), and stirred overnight at 20 C. The product mixture was concentrated, extracted 3 times with $CH_2Cl_2$ (5 mL), dried with $Na_2SO_4$ and the solvent evaporated. Flash chromatography (0-15% MeOH in $CH_2Cl_2$, silica) resulted in 28 mg of a clear oil. 1H NMR (400 MHz, $CDCl_3$) d 7.50 (s, 1H), 7.25 (d, J=8 Hz, 1H), 7.17 (d, J=8 Hz, 1H), 7.10 (s, 1H), 3.83 (s, 3H), 3.17 (m, 1H), 3.1-2.9 (m, 8H), 2.80 (dd, J=7, 13 Hz, 1H), 2.48 (bs, 1H), 1.40 (d, J=8 Hz, 3H). MS calculated for $C_{15}H_{18}BrN_3$+H: 320, observed: 320.

Example 29

(R,S)7-(3-Chlorophenyl)-1-methyl-2,3,4,5-tetrahydro-1H-3-benzazepine

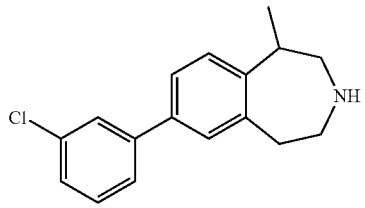 [SMILES: CC1CNCCc2cc(-c3cccc(Cl)c3)ccc21]

A solution of N-trifluoroacetyl-7-hydroxy-1-methyl-2,3,4,5-tetrahydro-1H-3-benzazepine, O-trifluoromethanesulfonate (50 mg, 0.123 mmol) in 1,4-dioxane (1.5 mL) was treated with 2-chlorophenylboronic acid (39 mg, 0.243 mmol), CsF (56 mg, 0.37 mmol), water (50 mg, 2.78 mmol), $Pd(PPh_3)_4$ (29 mg, 0.025 mmol) and stirred overnight at 75 C. The product mixture was diluted with EtOAc (20 mL), washed with water (10 mL), brine (10 mL), dried with $Na_2SO_4$ and concentrated. Flash chromatography (10-20% EtOAc in hexane, silica) resulted in 45 mg of a clear oil. MS calculated for $C_{19}H_{17}ClF_3NO$+H: 368, observed: 368. The product (27 mg, 0.073 mmol) was dissolved in methanol (2 mL) treated with 15% aqueous NaOH (2 mL), and stirred overnight at 20 C. The product mixture was concentrated, extracted 3 times with $CH_2Cl_2$ (5 mL), dried with $Na_2SO_4$ and the solvent evaporated to give 18 mg of a clear oil. 1H NMR (400 MHz, $CDCl_3$) d 7.54 (s, 1H), 7.42 (d, J=6 Hz, 1H), 7.35-7.21 (m, 5H), 3.14 (m, 1H), 3.1-2.9 (m, 8H), 2.80 (bm, 2H), 1.38 (d, J=8 Hz, 3H). MS calculated for $C_{17}H_{18}ClN_3$+H: 272, observed: 272.

Example 30

(R,S)7-(2-Chlorophenyl)-1-methyl-2,3,4,5-tetrahydro-1H-3-benzazepine

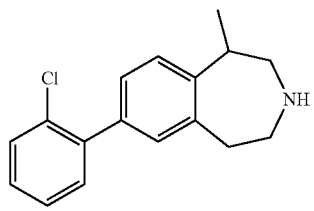 [SMILES: CC1CNCCc2cc(-c3ccccc3Cl)ccc21]

A solution of N-trifluoroacetyl-7-hydroxy-1-methyl-2,3,4,5-tetrahydro-1H-3-benzazepine, O-trifluoromethanesulfonate (50 mg, 0.123 mmol) in 1,4-dioxane (1.5 mL) was treated with 2-chlorophenylboronic acid (39 mg, 0.243 mmol), CsF (56 mg, 0.37 mmol), water (50 mg, 2.78 mmol), $Pd(PPh_3)_4$ (29 mg, 0.025 mmol) and stirred overnight at 75 C. The product mixture was diluted with EtOAc (20 mL), washed with water (10 mL), brine (10 mL), dried with $Na_2SO_4$ and concentrated. Flash chromatography (10-20% EtOAc in hexane, silica) resulted in 36 mg of a clear oil. MS calculated for C₁₉H₁₇ClF₃NO+H: 368, observed: 368. The product (27 mg, 0.073 mmol) was dissolved in methanol (2 mL) treated with 15% aqueous NaOH (2 mL), and stirred overnight at 20 C. The product mixture was concentrated, extracted 3 times with CH₂Cl₂ (5 mL), dried with Na₂SO₄ and the solvent evaporated to give 24 mg of a clear oil. 1H NMR (400 MHz, CDCl₃) d 7.44 (d, J=8 Hz, 1H), 7.35-7.22 (m, 5H), 7.15 (s, 1H), 3.14 (m, 1H), 3.1-2.9 (m, 8H), 2.80 (dd, J=13, Hz, 1H), 2.51 (bs, 1H), 1.38 (d, J=8 Hz, 3H). MS calculated for C₁₇H₁₈ClN₃+H: 272, observed: 272.

Example 31

(R,S)8-Chloro-1-hydroxy-2,3,4,5-tetrahydro-1H-3-benzazepine

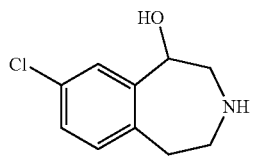 [SMILES: OC1CNCCc2ccc(Cl)cc21]

N-Trifluoroacetyl-8-chloro-1-oxo-,3,4,5-trihydro-1H-3-benzazepine

A solution of N-trifluoroacetyl-8-chloro-1-methylene-3,4,5-trihydro-1H-3-benzazepine (0.23 g, 0.80 mmol) in 1:1 methanol/dichloromethane (45 mL) was cooled to −78 C, treated with ozone until the solution turned blue (about 20 minutes), PPh₃ (0.21 g, 0.80 mmol) was added and the resulting solution was stirred 90 minutes while to warming to 20 C. The product mixture was concentrated and purified by flash chromatography (30% EtOAc in hexane, silica) resulting in 0.215 g of a white solid. MS calculated for C₁₂H₉ClF₃NO₂+H: 292, observed: 292.

8-Chloro-1-hydroxy-2,3,4,5-tetrahydro-1H-3-benzazepine

A solution of N-trifluoroacetyl-8-chloro-1-oxo-3,4,5-trihydro-1H-3-benzazepine (50 mg, 0.17 mmol) in methanol (2 mL) was treated with NaBH₄ and the resulting mixture was stirred 16 hours at 20 C. The white solid product was collected by filtration, washed with water and dried, resulting in 30 mg of a white solid. 1H NMR (400 MHz, CD₃OD) d 7.39 (s, 1H), 7.12 (d, J=8 Hz, 1H), 7.06 (d, J=8 Hz, 1H), 4.74 (d, 1=8 Hz, 1H), 3.1-2.7 (m, 6H). MS calculated for C₁₀H₁₂ClNO+H: 198, observed: 198.

Example 32

(R,S)8-Bromo-1-methyl-2,3,4,5-tetrahydro-1H-3-benzazepine

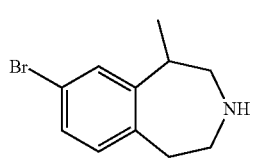

By the same general procedure as in example 26, (R,S)8-bromo-1-methyl-2,3,4,5-tetrahydro-1H-3-benzazepine was obtained from 4-bromophenethylamine as a colorless oil. 1H NMR (400 MHz, CDCl₃) d 7.27 (s, 1H), 7.22 (d, 1=8 Hz, 1H), 6.94 (d, 0.1=8 Hz, 1H), 3.1-2.85 (m, 6H), 2.72 (m, 1H), 2.25 (bs, 1H), 1.33 (d, 0.1=7 Hz, 3H). MS calculated for C₁₁H₁₄BrN+H: 240, observed: 240.

Example 33

(R,S)8-Fluoro-1-methyl-2,3,4,5-tetrahydro-1H-3-benzazepine

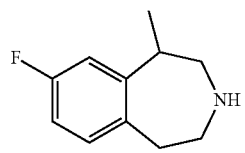

By the same general procedure as in example 26, (R,S)8-fluoro-1-methyl-2,3,4,5-tetrahydro-1H-3-benzazepine was obtained from 4-fluorophenethylamine as a colorless oil. 1H NMR (400 MHz, CDCl₃) d 7.00 (dd, J=8, 10 Hz, 1H), 6.86 (d, J=10 Hz, 1H), 6.76 (d, J=8 Hz, 1H), 3.08-2.56 (m, 7H), 1.85 (bs, 1H), 1.31 (d, J=7 Hz, 3H). MS calculated for C₁₁H₁₄FN+H: 180, observed: 180.

Example 34

(R,S)7-Fluoro-1-methyl-2,3,4,5-tetrahydro-1H-3-benzazepine

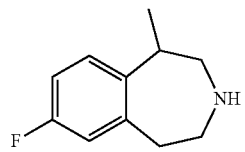

By the same general procedure as in example 26, (R,S)7-fluoro-1-methyl-2,3,4,5-tetrahydro-1H-3-benzazepine was obtained from 3-fluorophenethylamine as a colorless oil. 1H NMR (400 MHz, CDCl₃) d 7.09 (dd, J=6, 8 Hz, 1H), 6.85-6.78 (m, 2H), 3.10-2.89 (m, 6H), 2.71 (dd, J=7, 13 Hz, 1H), 1.91 (bs, 1H), 1.33 (d, J=7 Hz, 3H). MS calculated for C₁₁H₁₄FN+H: 180, observed: 180.

Example 35

(R,S)7-Chloro-1-methyl-2,3,4,5-tetrahydro-1H-3-benzazepine

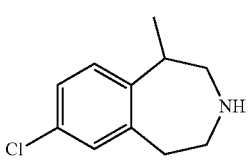

By the same general procedure as in example 26, (R,S)7-chloro-1-methyl-2,3,4,5-tetrahydro-1H-3-benzazepine was obtained from 3-chlorophenethylamine as a colorless oil. 1H NMR (400 MHz, CDCl$_3$) d 7.10 (d, J=8 Hz, 1H), 7.06 (m, 2H), 3.1-2.9 (m, 6H), 2.70 (dd, J=13, 7 Hz, 1H), 1.89 (bs, 1H), 1.31 (d, J=7 Hz, 3H). MS calculated for C$_{11}$H$_{14}$ClN+H: 196, observed: 196.

Example 36

(R,S)7,8-Dichloro-1-methyl-2,3,4,5-tetrahydro-1H-3-benzazepine

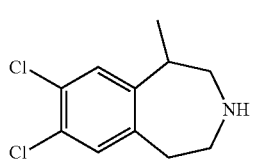

By the same general procedure as in example 26, (R,S)7,8-dichloro-1-methyl-2,3,4,5-tetrahydro-1H-3-benzazepine was obtained from 3,4-dichlorophenethylamine as a colorless oil. 1H NMR (400 MHz, CDCl$_3$) d 7.20 (s, 1H), 7.16 (s, 1H), 3.05-2.86 (m, 6H), 2.71 (dd, 1=7, 13 Hz, 1H), 1.83 (bs, 1H), 1.33 (d, J=7 Hz, 3H). MS calculated for C$_{11}$H$_{13}$Cl$_2$N+H: 230, observed: 230.

Example 37

(R,S)N-Methyl-8-chloro-1-methyl-2,3,4,5-tetrahydro-1H-3-benzazepine

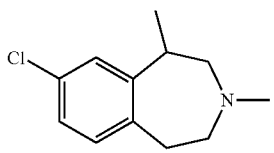

By the same general procedure as in example 9, (R,S)N-methyl-8-chloro-1-methyl-2,3,4,5-tetrahydro-1H-3-benzazepine was obtained from (R,S)8-chloro-1-methyl-2,3,4,5-tetrahydro-1H-3-benzazepine as a colorless oil. MS calculated for C$_{12}$H$_{16}$ClN+H: 210, observed: 210.

Example 38

(R,S)1-Methyl-7-trifluoromethoxy-2,3,4,5-tetrahydro-1H-3-benzazepine

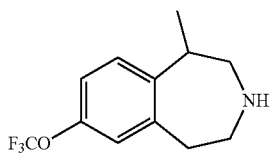

By the same general procedure as in example 26, (R,S)1-methyl-7-trifluoromethoxy-2,3,4,5-tetrahydro-1H-3-benzazepine was obtained from 3-trifluoromethoxyphenethy-lamine as a colorless oil. 1H NMR (400 MHz, CD$_3$OD) 7.39 (d, J=8 Hz, 1H), 7.19 (m, 1H), 3.46 (m, 2H), 3.38 (d, J=13 Hz, 1H), 3.29 (m, 1H), 3.16 (m, 2H), 3.05 (dd, J=13, 9 Hz, 1H), 1.50 (d, J=8 Hz, 3H). MS calculated for C$_{12}$H$_{14}$F$_3$NO+H: 246, observed: 246.

Example 39

(R,S)8-Iodo-1-methyl-7-trifluoromethoxy-2,3,4,5-tetrahydro-1H-3-benzazepine

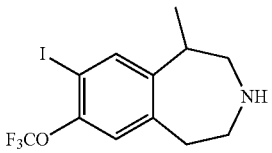 [SMILES: CC1CNCCc2cc(OC(F)(F)F)c(I)cc21]

By the same general procedure as in example 3, (R,S)8-iodo-1-methyl-7-trifluoromethoxy-2,3,4,5-tetrahydro-1H-3-benzazepine was obtained from N-trifluoroacetyl-1-methyl-7-trifluoromethoxy-2,3,4,5-tetrahydro-1H-3-benzazepine as a colorless oil. 1H NMR (400 MHz, CD$_3$OD) d 7.79 (s, 1H), 7.25 (s, 1H), 3.46-3.40 (m, 3H), 3.28-3.12 (m, 3H), 3.07 (dd, J=13, 9 Hz, 1H), 1.47 (d, J=7 Hz, 3H). MS calculated for C$_{12}$H$_{14}$F$_3$INO+H: 372, observed: 372.

Example 40

(R,S)N-Propyl-8-iodo-7-methoxy-1-methyl-2,3,4,5-tetrahydro-1H-3-benzazepine

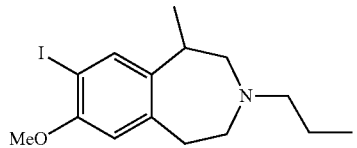 [SMILES: CCCN1CCc2cc(OC)c(I)cc2C(C)C1]

By the same general procedure as in example 10, (R,S)N-Propyl-8-iodo-7-methoxy-1-methyl-2,3,4,5-tetrahydro-1H-3-benzazepine was obtained from (R,S)8-iodo-7-methoxy-1-methyl-1,2,4,5-tetrahydro-3H-3-benzazepine as a colorless oil. MS calculated for C$_{15}$H$_{22}$INO+H: 360, observed: 360.

Example 41

(R,S)1-Ethyl-8-iodo-7-methoxy-2,3,4,5-tetrahydro-1H-3-benzazepine

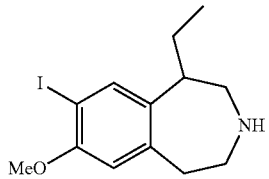 [SMILES: CCC1CNCCc2cc(OC)c(I)cc21]

By the same general procedure as in example 19, (R,S)1-ethyl-8-iodo-7-methoxy-2,3,4,5-tetrahydro-1H-3-benzazepine was obtained from N-trifluorolacetyl-1-ethyl-7-methoxy-2,3,4,5-tetrahydro-1H-3-benzazepine as a colorless oil. 1H NMR (400 MHz, CDCl₃) d 7.47 (s, 1H), 6.54 (s, 1H), 3.86 (s, 3H), 3.20-2.97 (m, 4H), 2.93-2.75 (m, 3H), 2.64 (m, 1H), 1.78 (m, 2H), 0.95 (dd, J=8, 8 Hz, 3H). MS calculated for $C_{13}H_{18}INO+H$: 332, observed: 332.

Example 42

(R,S)7-(3-Methoxyphenyl)-1-methyl-2,3,4,5-tetrahydro-1H-3-benzazepine

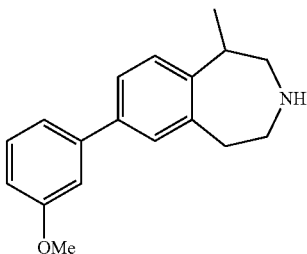 [SMILES: COc1cccc(-c2ccc3c(c2)CCNCC3C)c1]

By the same general procedure as in example 29, (R,S)7-(3-Methoxyphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. 1H NMR (400 MHz, CDCl₃) d 7.37 (dd, 1=7, 7 Hz, 1H), 7.30 (m, 2H), 7.21 (d, J=7 Hz, 1H), 7.14 (d, J=7 Hz, 1H), 7.09 (s, 1H), 6.86 (d, 0.1=8 Hz, 1H), 3.85 (s, 3H), 3.2-2.9 (m, 6H), 2.80 (m, 1H), 2.64 (bs, 1H), 1.38 (d, J=7 Hz, 3H). MS calculated for $C_{18}H_{21}NO+H$: 268, observed: 268.

Example 43

(R,S)7-(2,6-difluorophenyl)-1-methyl-2,3,4,5-tetrahydro-1H-3-benzazepine

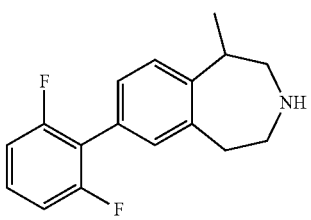 [SMILES: CC1CNCCc2cc(-c3c(F)cccc3F)ccc21]

By the same general procedure as in example 29, (R,S)7-(2,6-difluorophenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. 1H NMR (400 MHz, CDCl₃) d 7.35-7.10 (m, 5H), 6.95 (dd, J=7, 8 Hz, 1H), 3.2-2.9 (m, 6H), 2.79 (dd, J=8, 13 Hz, 1H), 2.70 (bs, 1H), 1.38 (d, 1=8 Hz, 3H). MS calculated for $C_{17}H_{17}F_2N+H$: 274, observed: 274.

Example 44

(R,S)7-(2-fluorophenyl)-8-chloro-1-methyl-2,3,4,5-tetrahydro-1H-3-benzazepine

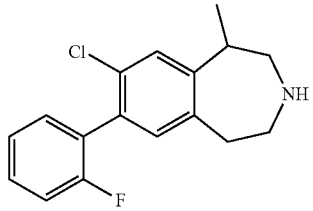 [SMILES: CC1CNCCc2cc(-c3ccccc3F)c(Cl)cc21]

By the same general procedure as in example 29, (R,S)7-(2-fluorophenyl)-8-chloro-1-methyl-2,3,4,5-tetrahydro-1H-3-benzazepine was obtained from N-trifluoroacetyl-8-chloro-7-hydroxy-1-methyl-2,3,4,5-tetrahydro-1H-3-benzazepine as a colorless oil. 1H NMR (400 MHz, CDCl₃) d 7.35-7.23 (m, 3H), 7.19-7.09 (m, 2H), 7.03 (s, 1H), 3.15-2.85 (m, 7H), 2.76 (dd, J=8, 13 Hz, 1H), 1.36 (d, J=8 Hz, 3H). MS calculated for $C_{17}H_{17}ClFN+H$: 290, observed: 290.

Example 45

(R,S)7-(2-Trifluoromethylphenyl)-1-methyl-2,3,4,5-tetrahydro-4H-3-benzazepine

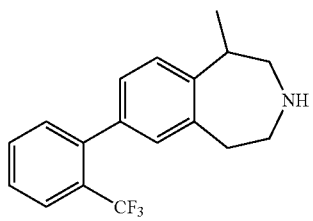 [SMILES: CC1CNCCc2cc(-c3ccccc3C(F)(F)F)ccc21]

By the same general procedure as in example 29, (R,S)7-(2-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. 1H NMR (400 MHz, CDCl₃) d 7.71 (d, J=8 Hz, 1H), 7.52 (dd, J=7, 8 Hz, 1H), 7.42 (dd, J=7, 8 Hz, 1H), 7.31 (d, J=7 Hz, 1H), 7.17 (d, J=8 Hz, 1H), 7.11 (d, J=8 Hz, 1H), 3.15 (m, 1H), 3.1-2.9 (m, 5H), 2.76 (dd, J=8, 13 Hz, 1H), 2.37 (bs, 1H), 1.38 (d, J=8 Hz, 3H). MS calculated for $C_{18}H_{18}F_3N+H$: 306, observed: 306.

Example 46

(R,S)7-(3-Trifluoromethylphenyl)-1-methyl-2,3,4,5-tetrahydro-1H-3-benzazepine

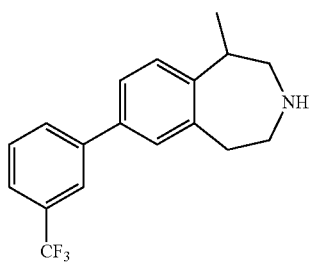 [SMILES: CC1CNCCc2cc(-c3cccc(C(F)(F)F)c3)ccc21]

By the same general procedure as in example 29, (R,S)7-(3-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. 1H NMR (400 MHz, CDCl$_3$) d 7.80 (s, 1H), 7.73 (d, J=8 Hz, 1H), 7.57-7.48 (m, 2H), 7.38 (d, J=8 Hz, 1H), 7.30 (s, 1H), 7.24 (d, J=7 Hz, 1H), 3.16 (m, 1H), 3.1-2.9 (m, 6H), 2.79 (dd, J=8, 13 Hz, 1H), 1.38 (d, J=8 Hz, 3H). MS calculated for C$_{18}$H$_{18}$F$_3$N+H: 306, observed: 306.

Example 47

(R,S)7-(4-Trifluoromethylphenyl)-1-methyl-2,3,4,5-tetrahydro-1H-3-benzazepine

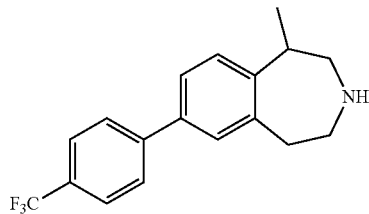 [SMILES: CC1CNCCc2cc(-c3ccc(C(F)(F)F)cc3)ccc21]

By the same general procedure as in example 29, (R,S)7-(4-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. 1H NMR (400 MHz, CDCl$_3$) d 7.65 (s, 4H), 7.38 (d, J=8 Hz, 1H), 7.31 (s, 1H), 7.24 (d, J=8 Hz, 1H), 3.15 (m, 1H), 3.1-2.9 (m, 5H), 2.80 (dd, J=8, 13 Hz, 1H), 2.48 (bs, 1H), 1.38 (d, J=8 Hz, 3H). MS calculated for C$_{18}$H$_{18}$F$_3$N+H: 306, observed: 306.

Example 48

(R,S)8-(2-Chlorophenyl)-1-methyl-2,3,4,5-tetrahydro-1H-3-benzazepine

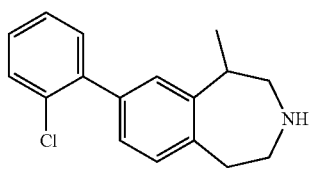 [SMILES: CC1CNCCc2ccc(-c3ccccc3Cl)cc21]

A solution of N-trifluoroacetyl-8-bromo-1-methyl-2,3,4,5-tetrahydro-1H-3-benzazepine (84 mg, 0.229 mmol) in dimethylformamide (2.5 mL) was treated with 2-chlorophenylboronic acid (43 mg, 0.275 mmol), CsF (52 mg, 0.34 mmol), water (70 mg, 3.9 mmol), Pd(PPh$_3$)$_4$ (27 mg, 0.023 mmol) and stirred overnight at 75 C. The product mixture was diluted with EtOAc (20 mL), washed with water (10 mL), brine (10 mL), dried with Na$_2$SO$_4$ and concentrated. Flash chromatography (10-20% EtOAc in hexane, silica) resulted in 36 mg of a clear oil. MS calculated for C$_{19}$H$_{17}$ClF$_3$NO+H: 368, observed: 368. The product (39 mg, 0.106 mmol) was dissolved in methanol (2 mL) treated with 15% aqueous NaOH (2 mL), and stirred overnight at 20 C. The product mixture was concentrated, extracted 3 times with CH$_2$Cl$_2$ (5 mL), dried with Na$_2$SO$_4$ and the solvent evaporated to give 18 mg of a clear oil. 1H NMR (400 MHz, CDCl$_3$) d 7.44 (d, J=8 Hz, 1H), 7.35-7.17 (m, 5H), 7.12 (d, J=8 Hz, 1H), 3.14 (m, 1H), 3.1-2.9 (m, 5H), 2.79 (dd, J=7, 13 Hz, 1H), 2.36 (bs, 1H), 1.36 (d, J=7 Hz, 3H). MS calculated for C$_{17}$H$_{18}$ClN$_3$+H: 272, observed: 272.

Example 49

(R,S)7-Methoxy-1-methyl-8-trifluoromethyl-2,3,4,5-tetrahydro-1H-3-benzazepine

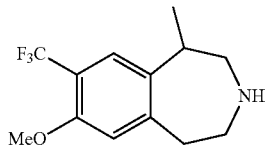

A solution of N-trifluoromethylacetyl-8-iodo-7-methoxy-1-methyl-1,2,4,5-tetrahydro-3H-3-benzazepine (135 mg, 0.327 mmol) in dimethylformamide (3 mL) and toluene (0.5 mL) was treated with sodium trifluoroacetate (133 mg, 0.981 mmol), copper (I) iodide (124 mg, 0.654 mmol) and the toluene distilled off to remove any residual water. The reaction mixture was stirred at 155 C for 3.5 hours, diluted with EtOAc, filtered, absorbed on silica and purified by flash chromatography (10% EtOAc in hexane, silica) resulting in 26 mg of a colorless oil. MS calculated for C$_{15}$H$_{15}$F$_6$NO$_2$+H: 356, observed: 356. The intermediate (26 mg, 0.073 mmol) in methanol (2 mL) was treated with 15% aqueous NaOH (2 mL), and stirred 0.5 hours at 50 C. The product mixture was diluted with water (5 mL), extracted twice with EtOAc (5 mL), the combined organic phases were washed with brine (5 mL), dried with Na$_2$SO$_4$ and concentrated to give 14 mg of a colorless oil. 1H NMR (400 MHz, CDCl$_3$) d 7.32 (s, 1H), 6.73 (s, 1H), 3.89 (s, 3H), 3.1-2.9 (bm, 8H), 2.75 (bm, 1H), 2.23 (bs, 1H), 1.36 (d, J=8 Hz, 3H). MS calculated for C$_{13}$H$_{16}$F$_3$NO+H: 260, observed: 260.

Example 50

(R,S)7-Methoxy-1-methyl-8-pentafluoroethyl-2,3,4,5-tetrahydro-1H-3-benzazepine

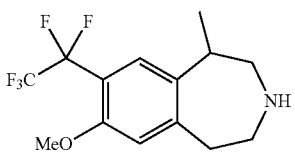 [SMILES: COc1cc2c(cc1C(F)(F)C(F)(F)F)C(C)CNCC2]

A solution of N-trifluoromethylacetyl-8-iodo-7-methoxy-1-methyl-1,2,4,5-tetrahydro-3H-3-benzazepine (100 mg, 0.242 mmol) in dimethylformamide (3 mL) and toluene (1 mL) was treated with sodium pentafluoropropionate (64 mg, 0.344 mmol), copper (I) iodide (92 mg, 0.484 mmol) and the toluene distilled off to remove any residual water. The reaction mixture was stirred at 160 C for 3.5 hours, diluted with EtOAc, filtered, absorbed on silica and purified by flash chromatography (10% EtOAc in hexane, silica) resulting in 22 mg of a colorless oil. MS calculated for C$_{16}$H$_{15}$F$_8$NO$_2$+H: 406, observed: 406. The intermediate (22 mg, 0.054 mmol) in methanol (2 mL) was treated with 15% aqueous NaOH (2 mL), and stirred 0.5 hours at 50 C. The product mixture was diluted with water (5 mL), extracted twice with EtOAc (5 mL), the combined organic phases were washed with brine (5 mL), dried with $Na_2SO_4$ and concentrated to give 14 mg of a colorless oil. 1H NMR (400 MHz, $CDCl_3$) d 7.25 (s, 1H), 6.74 (s, 1H), 3.85 (s, 3H), 3.1-2.9 (bm, 6H), 2.76 (bm, 1H), 2.37 (bs, 1H), 1.35 (d, J=8 Hz, 3H). MS calculated for $C_{14}H_{16}F_5NO+H$: 310, observed: 310.

Example 51

(R,S)8-Trifluoromethyl-1-methyl-2,3,4,5-tetrahydro-1H-3-benzazepine

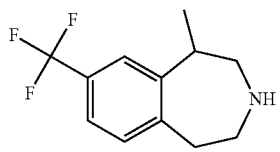 [SMILES: CC1CNCCc2ccc(C(F)(F)F)cc21]

By the same general procedure as in example 26, (R,S)8-trifluoromethyl-1-methyl-2,3,4,5-tetrahydro-1H-3-benzazepine was obtained from 4-trifluoromethylphenethylamine as a colorless oil. 1H NMR (400 MHz, DMSO) d 7.55 (d, J=8 Hz, 1H), 7.49 (s, 1H), 7.43 (d, J=8 Hz, 1H), 3.55-3.50 (m, 1H) 3.43-3.23 (m, 7H), 3.13 (dd, J=16, 7 Hz, 1H), 3.0-2.91 (m, 2H), 1.36 (d, J=7 Hz, 3H). MS calculated for $C_{12}H_{14}F_3N+H$: 230.19, observed: 230.4

Example 52

(R,S)8-bromo-1-methoxymethyl-7-methoxy-2,3,4,5-tetrahydro-1H-3-benzazepine

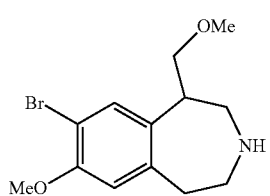 [SMILES: COCC1CNCCc2cc(OC)c(Br)cc21]

A solution of 8-bromo-1-hydroxymethyl-7-methoxy-2,3,4,5-tetrahydro-1H-3-benzazepine (0.075 g, 0.26 mmol) in dichloromethane (2 mL) was treated with $BOC_2O$ (0.062 g, 0.29 mmol), and stirred overnight at 20 C. The product was absorbed on silica and purified by flash chromatography (33% EtOAc in hexane, silica) resulting in 0.034 g of a clear oil. MS calculated for $C_{17}H_{24}BrNO_4+H$: 386, observed: 386. The BOC-protected intermediate was dissolved in dimethylformamide (1 mL), treated with excess NAH and excess iodomethane sequentially, and then stirred for 1 hour at 20 C. The reaction mixture was quenched with water (5 mL), extracted twice with EtOAc (5 mL), the combined organic phases were washed with brine (5 mL), dried with $Na_2SO_4$ and concentrated to give 0.019 g of a clear oil. MS calculated for $C_{18}H_{26}BrNO_4+H$: 400, observed: 400. The N—BOC protected methylether was then treated with 4M HCl in dioxane (1 mL) and stirred 2 hours at 20 C. Evaporation resulted in 0.009 g of the desired product as a clear oil. 1H NMR (400 MHz, $CD_3OD$) d 7.30 (s, 1H), 6.92 (s, 1H), 3.87 (s, 3H), 3.65 (s, 3H) 3.5-3.1 (m, 9H). MS calculated for $C_{13}H_{18}BrNO_2+H$: 300, observed: 300.

Example 53

(R,S)8-Chloro-1-ethyl-2,3,4,5-tetrahydro-1H-3-benzazepine

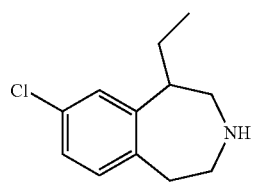

N-Crotyl, N-trifluoroacetyl-2-iodo-4-chlorophenethylamine

A solution of N-trifluoroacetyl-2-iodo-4-chlorophenethylamine (6.2 g, 15.8 mmol) in dimethylformamide (350 mL) was treated with $K_2CO_3$ (15.8 g, 114 mmol) and crotyl bromide (6.0 g, 44 mmol) sequentially, the mixture was stirred at 60 C for 16 hours and then cooled to 20 C. The mixture was diluted with EtOAc (350 mL), washed with water (3×300 mL), dried with $Na_2SO_4$ and concentrated. Flash chromatography (5-15% EtOAc in hexane) resulted in 2.5 g of a clear oil. MS calculated for $C_{14}H_{14}ClF_3INO+H$: 432, observed: 432.

N-Trifluoroacetyl-8-chloro-1-ethyl-2,3,4,5-tetrahydro-1H-3-benzazepine

A solution of N-crotyl, N-trifluoroacetyl-2-iodo-4-chlorophenethylamine (2.5 g, 5.8 mmol) in dimethylformamide (250 mL) was treated with KOAc (1.07 g, 10.9 mmol), n-$Bn_2Et_2NBr$ (1.33 g, 5.84 mmol), $Pd(OAc)_2$ (0.063 g, 0.28 mmol) and stirred overnight at 77 C. The product mixture was cooled to 20 C, filtered, diluted with water (100 mL), extracted with EtOAc (3×100 mL), the combined organic phases washed with water (100 mL), brine (100 mL), dried with $Na_2SO_4$ and concentrated. Flash chromatography (2-20% EtOAc in hexane, silica) resulted in 0.339 g of a clear oil. The product, which was assumed to be a mixture of double-bond isomers, was dissolved in methanol (50 mL) treated with $Et_3N$ (0.2 mL), 10% Pd/C (0.10 g) and stirred 16 hours under 100 psi of hydrogen. The product mixture was filtered, concentrated and purified by flash chromatography (5% EtOAc in hexane, silica) resulting in 0.20 g of a white solid. MS calculated for $C_{14}H_{15}ClF_3NO+H$: 306, observed: 306.

8-Chloro-1-ethyl-2,3,4,5-tetrahydro-1H-3-benzazepine

A solution of N-trifluoroacetyl-8-chloro-1-ethyl-2,3,4,5-tetrahydro-1H-3-benzazepine (63 mg, 0.207 mmol) in methanol (2 mL) was treated with 15% aqueous NaOH (2 mL), and stirred for 3.5 hours at 60 C. The product mixture was concentrated, extracted 3 times with $CH_2Cl_2$ (5 mL), dried with $Na_2SO_4$ and concentrated to give 35 mg of a clear oil. 1H NMR (400 MHz, DMSO-$d_6$) d 7.2 (m, 3H), 3.3-3.0 (m, 7H), 1.9-1.6 (m, 2H), 0.91 (t, J=7 Hz, 3H). MS calculated for $C_{12}H_{16}ClN+H$: 210, observed: 210.

Example 54

(R,S)8-Chloro-7-fluoro-1-methyl-2,3,4,5-tetrahydro-1H-3-benzazepine

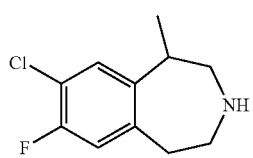

N-Trifluoroacetyl-8-chloro-7-fluoro-1-methyl-2,3,4,5-tetrahydro-1H-3-benzazepine A solution of N-trifluoroacetyl-8-chloro-1-methyl-2,3,4,5-tetrahydro-1H-3-benzazepine (2.5 g, 8.5 mmol) in 1,2-dichloroethane (15 mL) was treated with Selectfluor (3.9 g, 11 mmol), trifluoromethanesulfonic acid (8 mL, 90 mmol) and stirred 60 hours at 75 C. The product mixture was poured into water (200 mL), extracted with EtOAc (200 mL), the organic phase washed with saturated aqueous NaHCO$_3$ (2×100 mL), brine (100 mL), dried with Na$_2$SO$_4$ and concentrated. The crude product was purified by flash chromatography (6% EtOAc in hexane, silica) resulting in 1.6 g of a white solid. MS calculated for $C_{13}H_{12}ClF_4NO+H$: 310, observed: 310.

8-Chloro-7-fluoro-1-methyl-2,3,4,5-tetrahydro-1H-3-benzazepine

A solution of N-trifluoroacetyl-8-chloro-7-fluoro-1-methyl-2,3,4,5-tetrahydro-1H-3-benzazepine (160 mg, 0.22 mmol) in methanol (3 mL) was treated with 15% aqueous NaOH (2 mL), and stirred for 3.5 hours at 25 C. The product mixture was concentrated, extracted 3 times with CH$_2$Cl$_2$ (5 mL), dried with Na$_2$SO$_4$ and concentrated to give 93 mg of a clear oil. 1H NMR (400 MHz, CDCl$_3$) d 7.11 (m, 1H), 6.85 (m, 1H), 3.05-2.95 (m, 3H), 2.95-2.80 (m, 3H), 2.68 (m, 1H), 2.38 (bm, 1H), 1.31 (m, 3H). MS calculated for $C_{11}H_{13}ClFN+H$: 214, observed: 214.

Example 55

Separation of Enantiomers for Selected Compounds of the Invention

The following compounds were separated into their respective enantiomers using a Varian ProStar HPLC system with a 20 mm×250 mm Chiralcel OD chiral column, eluting with 0.2% diethylamine in various concentrations of isopropanol (IPA) in hexanes, see Table 1 below. In some cases, the separations were performed on the intermediate trifluoroacetamide protected amines.

TABLE 1

| Example | Enantiomer | Retention time for the free amine (mins) | Retention time for the trifluoro-acetamide | Conditions |
| --- | --- | --- | --- | --- |
| 1 | 1 | 21.9 | | 5% IPA in hexane |
| | 2 | 24.5 | | 10 mL/min |
| 2 | 1 | 42 | | 5% IPA in hexane |
| | 2 | 47 | | 9 mL/min |
| 3 | 1 | 20.8 | | 5% IPA in hexane |
| | 2 | 24.2 | | 10 mL/min |
| 19 | 1 | 34.9 | | 1% IPA in hexane |
| | 2 | 39.5 | | 9 mL/min |
| 26 | 1 | | 23.8 [1] | 5% IPA in hexane |
| | 2 | | 29.2 [2] | 7 mL/min |
| 37 | 1 | | 23.8 [3] | 5% IPA in hexane |
| | 2 | | 29.2 [4] | 7 mL/min |
| 51 | 1 | | 18.6 [5] | 1% IPA in hexane |
| | 2 | | 21.4 [6] | 9 mL/min |
| 53 | 1 | | 13.7 [7] | 5% IPA in hexane |
| | 2 | | 20.2 [8] | 10 mL/min |

[1] The separated trifluoroacetamide enantiomer was hydrolyzed to give Enantiomer 1 of Compound 26.
[2] The separated trifluoroacetamide enantiomer was hydrolyzed to give Enantiomer 2 of Compound 26.
[3] The separated trifluoroacetamide enantiomer was hydrolyzed and subsequently N-methylated to give Enantiomer 1 of Compound 37.
[4] The separated trifluoroacetamide enantiomer was hydrolyzed and subsequently N-methylated to give Enantiomer 2 of Compound 37.
[5] The separated trifluoroacetamide enantiomer was hydrolyzed to give Enantiomer 1 of Compound 51.
[6] The separated trifluoroacetamide enantiomer was hydrolyzed to give Enantiomer 2 of Compound 51.
[7] The separated trifluoroacetamide enantiomer was hydrolyzed to give Enantiomer 1 o Compound 53.
[8] The separated trifluoroacetamide enantiomer was hydrolyzed to give Enantiomer 2 of Compound 53.

Example 56

Intracellular IP$_3$ Accumulation Assay

HEK293 cells were transfected in 15 cm sterile dishes with or without (control) 16 ug of human 5-HT$_{2C}$ receptor cDNA using 25 ul of lipofectamine. Cells were then incubated for 3-4 hours at 37° C./5% CO$_2$ and then transfection media was removed and replaced with 100 ul of DMEM. Cells were then plated onto 100 cm sterile dishes. The next day cells were plated into 96 well PDL microtiter plates at a density of 55K/0.2 ml. Six hours later, media was exchanged with [$^3$H] inositol (0.25 uCi/well) in inositol free DMEM and plates were incubated at 37° C./5% CO$_2$ overnight. The next day, wells were aspirated and 200 ul of DMEM containing test compound, 10 uM pargyline, and 10 mM LiCl was added to appropriate wells. Plates were then incubated at 37° C./5% CO$_2$ for three to hours followed aspiration and by addition of fresh ice cold stop solution (1M KOH, 19 mM Na-borate, 3.8 mM EDTA) to each well. Plates were kept on ice for 5-10 min and the wells were neutralized by addition of 200 ul of fresh ice cold neutralization solution (7.5% HCl). Plates were then frozen until further processing is desired. The lysate was then transferred into 1.5 ml Eppendorf tubes and 1 ml of chloroform/methanol (1:2) was added/tube. The solution was vortexed for 15 seconds and the upper phase was applied to a Biorad AG1-X8™ anion exchange resin (100-200 mesh). First, the resin was washed with water at 1:1.25 W/V and 0.9 ml of upper phase was loaded onto the column. The column was then washed with 10 ml of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water.

The biological activities in the IP Accumulation Assay for several representative compounds are shown in Table 2 below:

TABLE 2

| Compound (Example Number) | $5-HT_{2C}$ $(IC_{50})$* IP Accumulation Assay (nM) |
|---|---|
| 1 | 4.2 |
| 2 | 4.5 |
| 3 | 1.4 |
| 4 | 2.1 |
| 5 | 12.1 |
| 12 | 6.3 |
| 19 | 18 |
| 26 | 5.8 |
| 32 | 2.1 |

*Reported values are averages of at least two trials.

The majority of the other compounds of the Examples were tested at least once, and they showed activities in the IP Accumulation Assay in the range between ~1.4 nM and ~5 µM.

Example 57

Inhibition of Food Intake in Food-Deprived Rats

Male Sprague-Dawley rats (250-350 g) were deprived of food overnight prior to testing. Prior to food deprivation, the animals were weighed and separated into treatment groups in order to balance groups according to body weight. On the test day, animals were placed into individual cages (no bedding) at 9:00 am with free access to water. At 10:00 am, animals were injected with test compound (p.o., i.p., or s.c.) and then presented with a pre-weighed amount of food in a dish either 60 min (p.o.) or 30 min (i.p. and s.c.) after drug administration. Food consumption over different time points was then determined by weighing the food cup at 1, 2, 4, and 6 hr after the food was presented. Thus, food consumption was measured at 2, 3, 5, and 7 hr post-injection in p.o. studies, and at 1.5, 2.5, 4.5, and 6.5 hr post-injection in i.p. and s.c. studies.

Figure 1B:
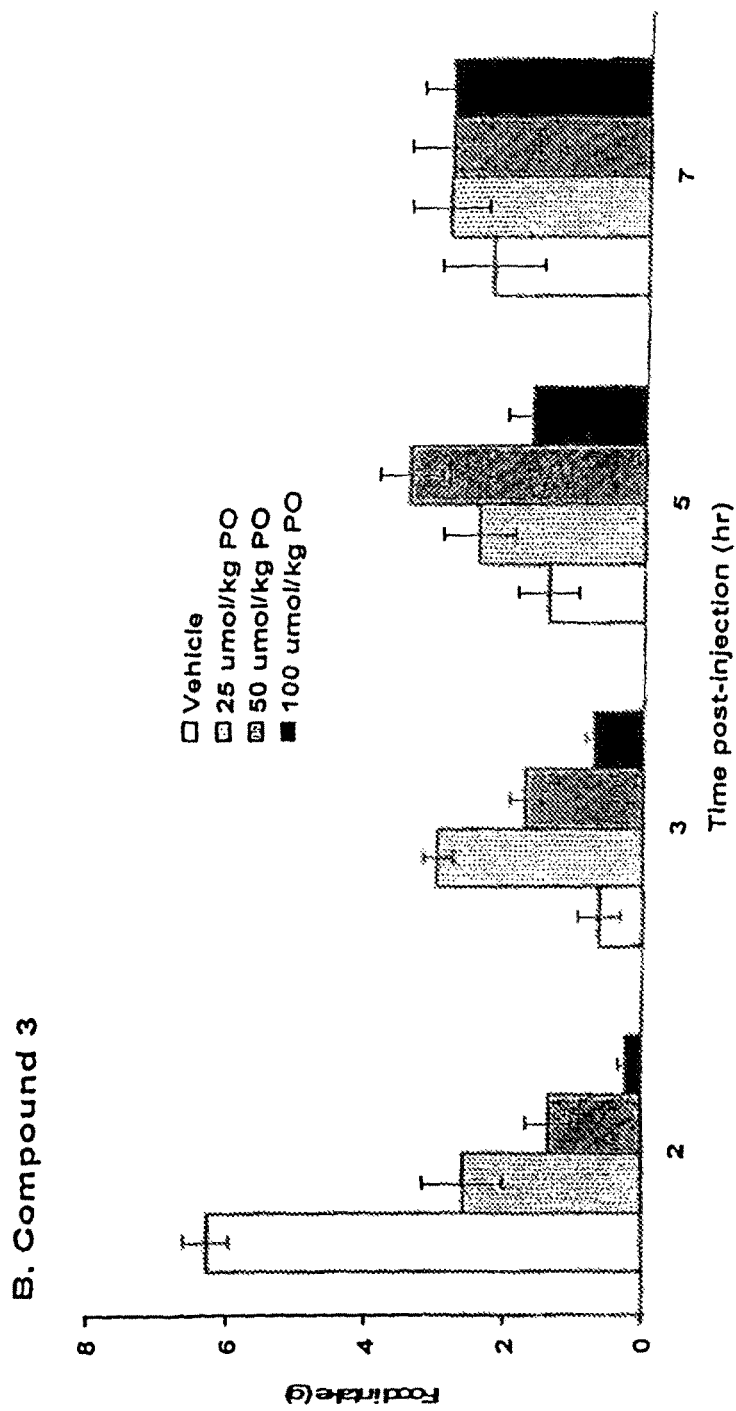
Figure 1C:
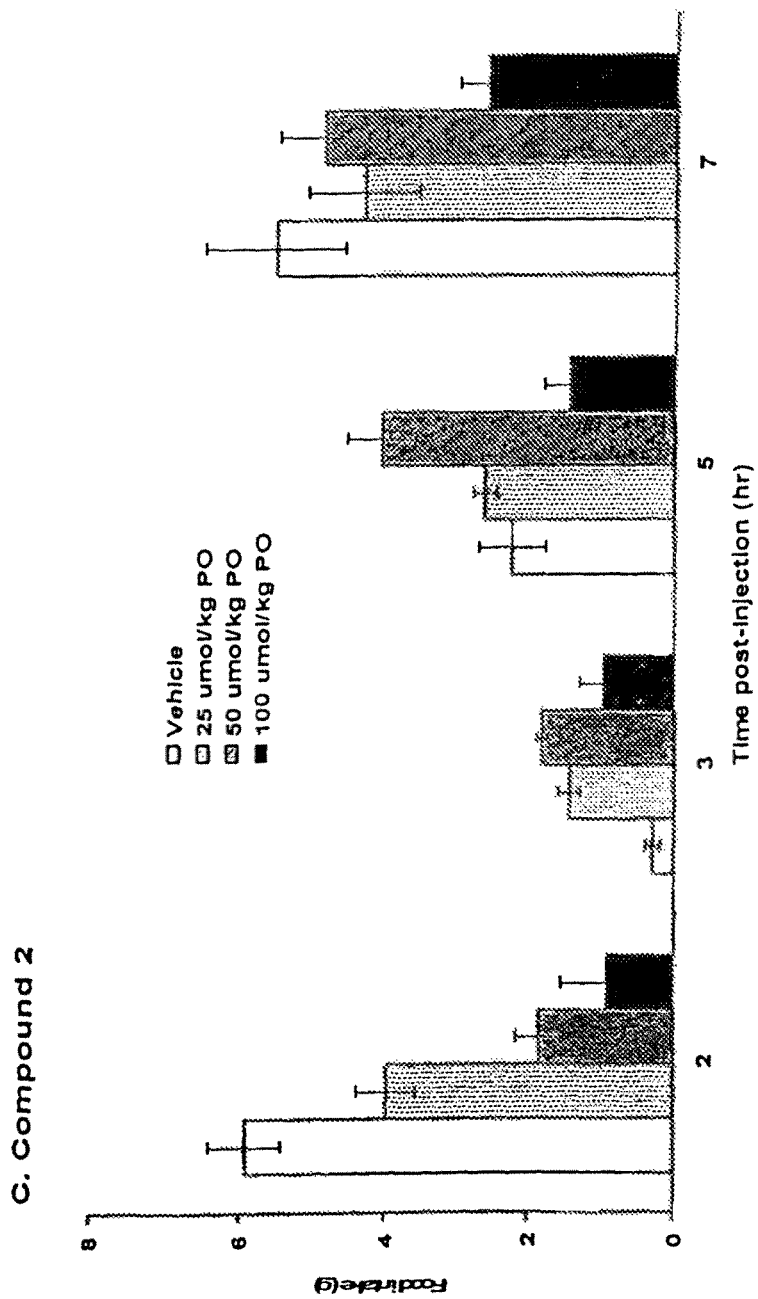
Figure 1D:
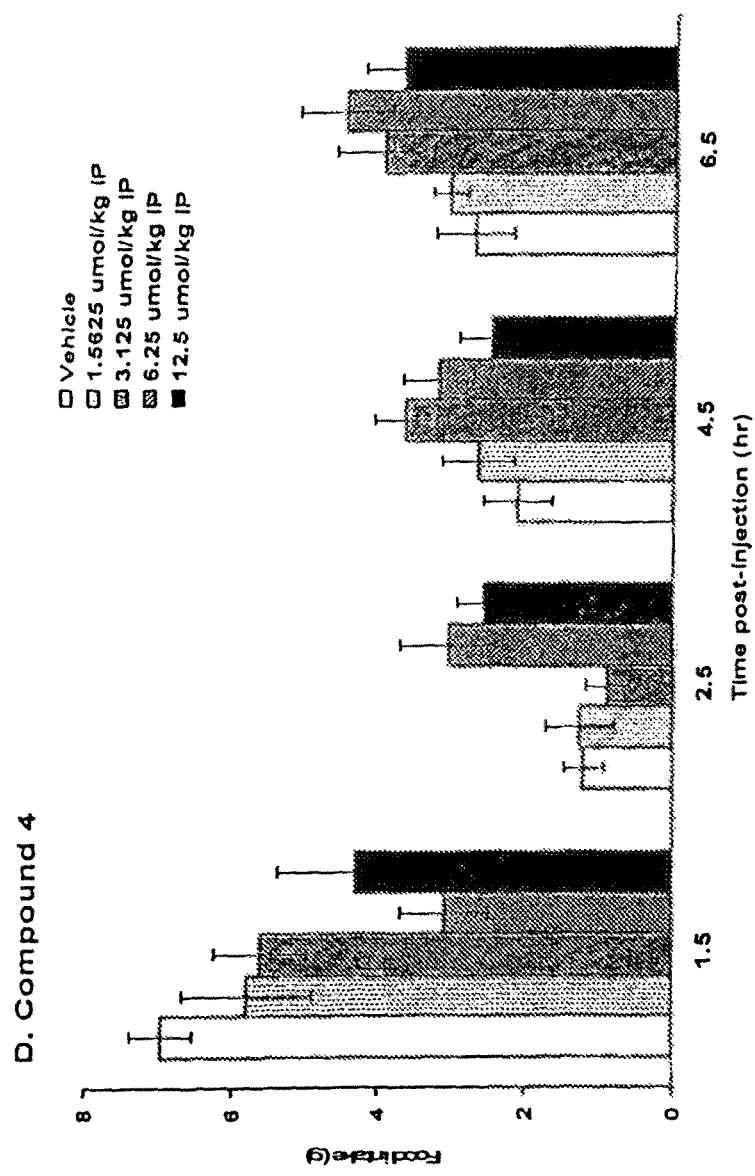
Figure 1E:
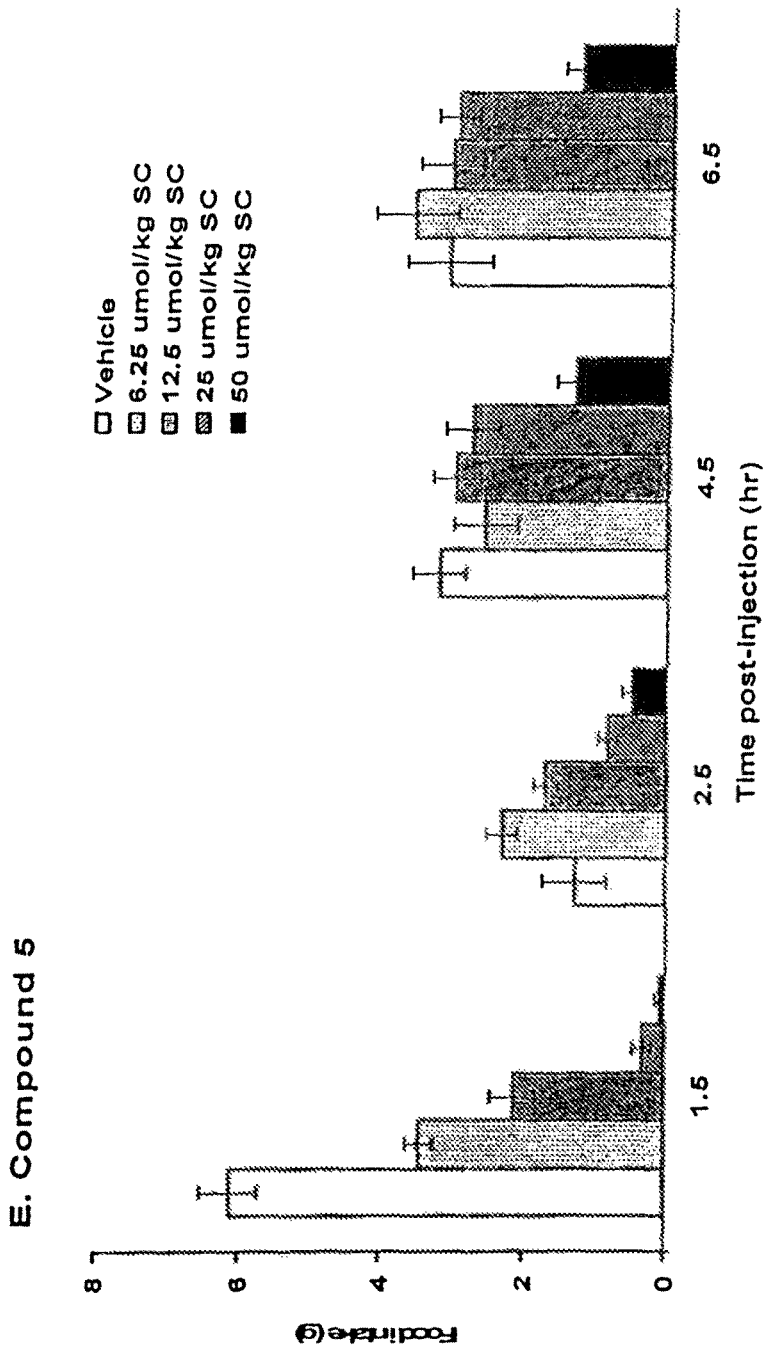
Figure 1F:
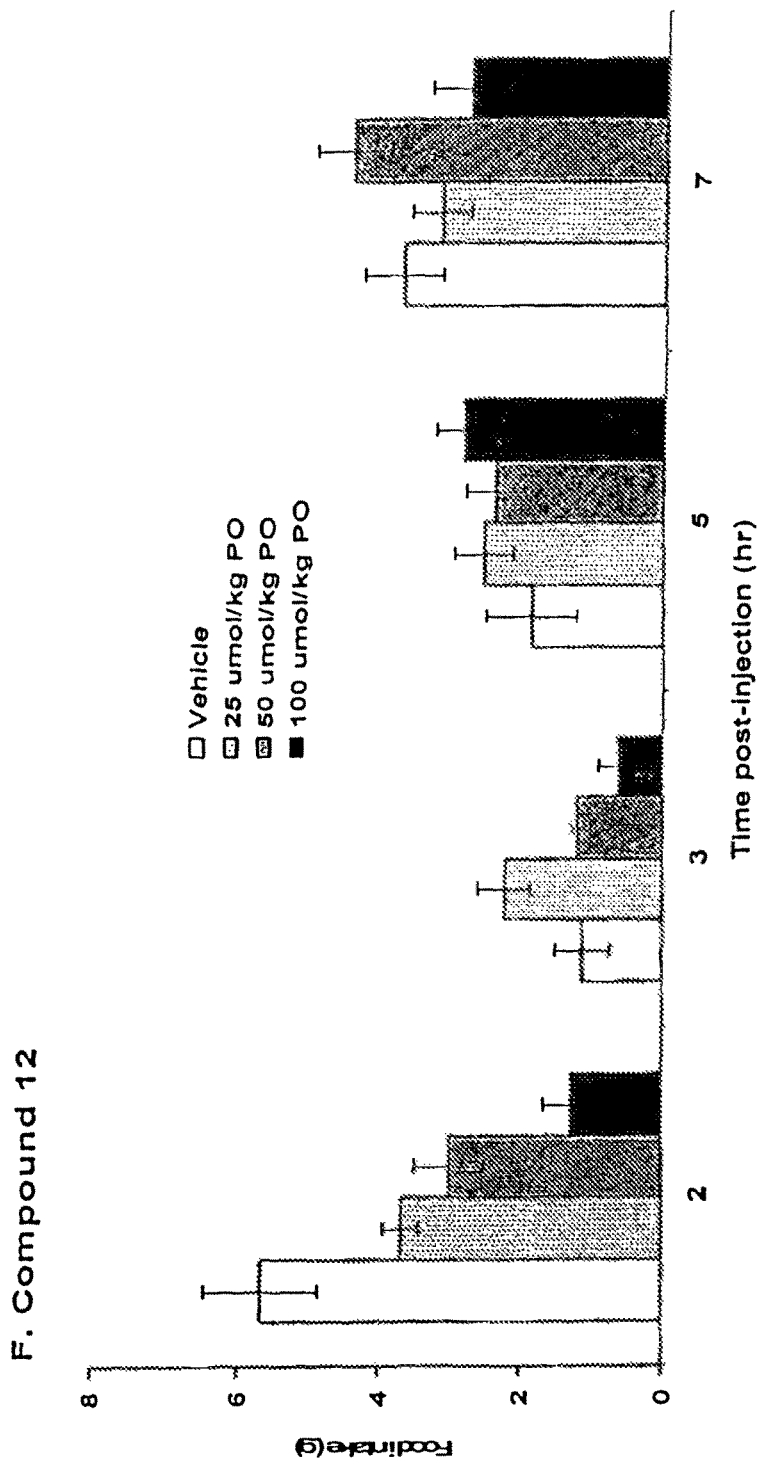
Figure 1G:
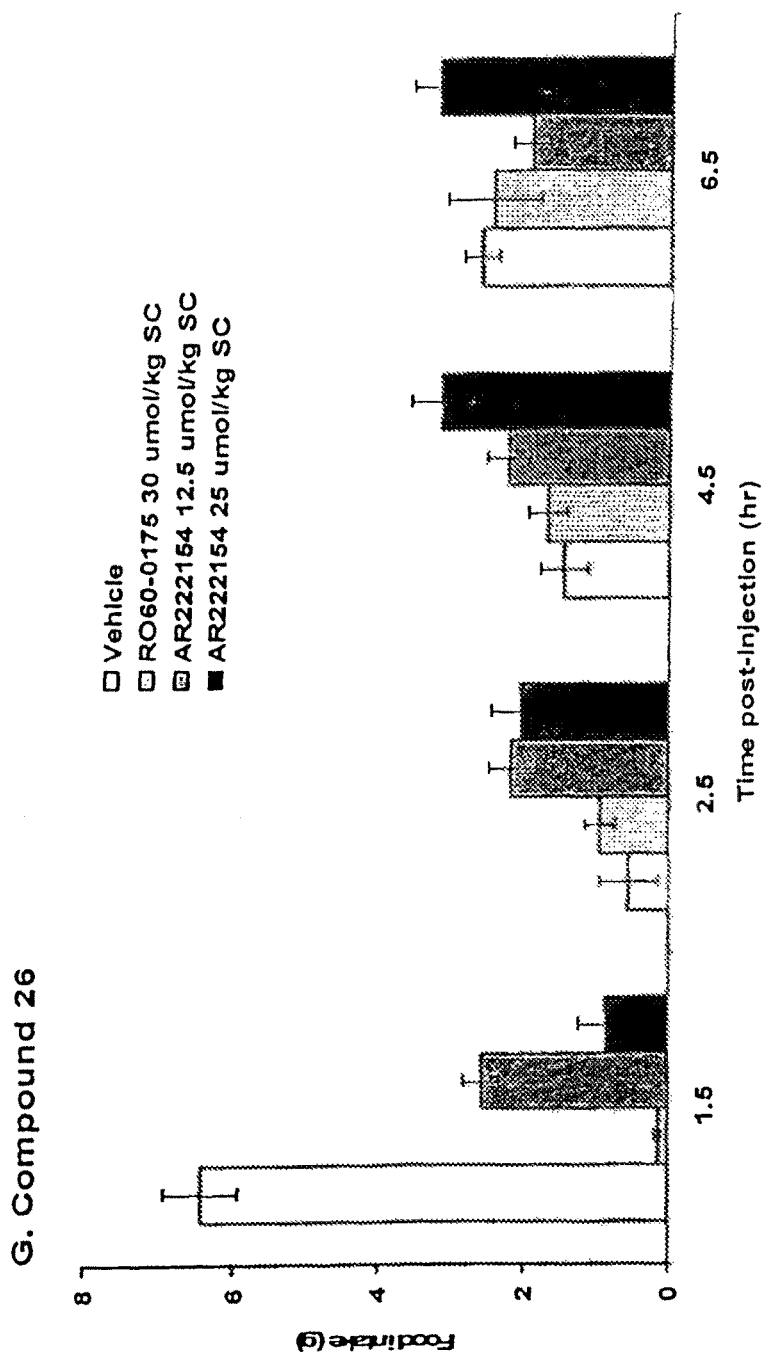

FIGS. 1A-G illustrate the effects of seven different compounds on food intake in food-deprived rats. All compounds inhibited food intake dose-dependently. This effect was consistently most pronounced over the first 1 hr after food presentation. Some compounds (FIGS. 1A, 1C, and 1E) maintained an inhibitory effect on food intake relative to vehicle-treated controls at 6 hr after food presentation. Compounds were also shown to be effective via all routes of administration including p.o.

It is intended that each of the patents, applications, printed publications, and other published documents mentioned or referred to in this specification be herein incorporated by reference in their entirety.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. The compound that is N-trifluoroacetyl-8-chloro-1-methyl-2,3,4,5-tetrahydro-1H-3-benzazepine.

2. The compound that is N-trifluoroacetyl-8-chloro-1-methylene-2,3,4,5-tetrahydro-1H-3-benzazepine.

* * * * *